US012797368B2

(12) United States Patent
Wei et al.

(10) Patent No.: US 12,797,368 B2
(45) Date of Patent: Nov. 17, 2026

(54) INTRANASAL DANTROLENE ADMINISTRATION FOR TREATMENT OF ALZHEIMER'S DISEASE

(71) Applicant: THE TRUSTEES OF THE UNIVERSITY OF PENNSYLVANIA, Philadelphia, PA (US)

(72) Inventors: Huafeng Wei, Cherry Hill, NJ (US); Qing Cheng Meng, Ardmore, PA (US); Ge Liang, Wynnewood, PA (US); Maryellen Fazen Eckenhoff, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1028 days.

(21) Appl. No.: 17/623,246

(22) PCT Filed: Jun. 29, 2020

(86) PCT No.: PCT/US2020/040198
§ 371 (c)(1),
(2) Date: Dec. 28, 2021

(87) PCT Pub. No.: WO2020/264531
PCT Pub. Date: Dec. 30, 2020

(65) Prior Publication Data
US 2022/0354827 A1 Nov. 10, 2022

Related U.S. Application Data

(60) Provisional application No. 62/868,820, filed on Jun. 28, 2019.

(51) Int. Cl.
*A61K 31/4178* (2006.01)
*A61K 9/00* (2006.01)
*A61K 45/06* (2006.01)
*A61P 25/28* (2006.01)

(52) U.S. Cl.
CPC ........ *A61K 31/4178* (2013.01); *A61K 9/0043* (2013.01); *A61K 45/06* (2013.01); *A61P 25/28* (2018.01)

(58) Field of Classification Search
CPC .. A61K 31/4178; A61K 9/0043; A61K 45/06; A61P 25/28; A61P 43/00
See application file for complete search history.

(56) References Cited

U.S. PATENT DOCUMENTS

| | | | |
|---|---|---|---|
| 9,271,964 B2 | 3/2016 | Anderson et al. | |
| 2006/0030548 A1 | 2/2006 | Dong et al. | |
| 2009/0011315 A1 | 1/2009 | Gauckler et al. | |
| 2010/0040575 A1 | 2/2010 | Hoffman et al. | |
| 2010/0311697 A1* | 12/2010 | Went ...................... | A61P 25/00 514/297 |
| 2012/0040970 A1 | 2/2012 | Al-Ghananeem | |

FOREIGN PATENT DOCUMENTS

| | | |
|---|---|---|
| JP | 4853202 B2 | 1/2012 |
| WO | WO 2004/004699 | 1/2005 |
| WO | WO 2009/022934 | 2/2009 |
| WO | WO 2014/016430 | 1/2014 |
| WO | WO 2019/009359 | 1/2019 |
| WO | WO 2019/050293 A1 | 3/2019 |

OTHER PUBLICATIONS

Girard et al., (2014), Onset of hippocampus-dependent memory impairments in 5XFAD transgenic mouse model of Alzheimer's disease. Hippocampus, 24: 762-772. https://doi.org/10.1002/hipo.22267 (Abstract Only) (Year: 2014).*
Lista S, O'Bryant SE, Blennow K, et al. Biomarkers in Sporadic and Familial Alzheimer's Disease. Journal of Alzheimer's Disease. 2015;47(2):291-317. doi:10.3233/JAD-143006 (Year: 2015).*
Joynt RL. Dantrolene sodium: long-term effects in patients with muscle spasticity. Arch Phys Med Rehabil. May 1976;57(5):212-7. PMID: 776122. Abstract Only (Year: 1976).*
Pinder, R.M., Brogden, R.N., Speight, T.M. et al. Dantrolene Sodium. Drugs 13, 3-23 (1977). Journal of Neuromuscular Diseases 10 (2023) 1145-1149 Abstract Only (Year: 1977).*
Silva et al., J Neuromuscul Dis. 2023; 10(6):1145-1149. doi: 10.3233/JND-230007. PMID: 37781817; PMCID: PMC106 (Year: 2023).*
Oo et al., Mol Pharmacol. Jul. 2015;88(1):57-63. doi: 10.1124/mol.115.097691. Epub Apr. 28, 2015. PMID: 25920678; PMCID: PMC4468648. (Year: 2015).*

(Continued)

*Primary Examiner* — James H Alstrum-Acevedo
*Assistant Examiner* — Chantal Adlam
(74) *Attorney, Agent, or Firm* — Mark S. Cohen; PEARL COHEN LLP

(57) ABSTRACT

Methods for inhibiting impaired neurogenesis and/or synaptogenesis in neurons in a subject with or suspected of having Alzheimer's Disease (AD), methods for improving and/or slowing the decline of cognitive function after onset of neuropathology and cognitive dysfunction, which neuropathology and cognitive dysfunction are caused by AD, methods for improving and/or slowing the decline of memory before onset of symptoms of AD, methods for increasing concentration and duration of dantrolene in the brain, and methods for improving and/or slowing the decline of memory after onset of symptoms of AD, the methods comprising intranasally administering to a subject in need thereof an amount of a pharmaceutical composition comprising dantrolene effective to inhibit over-activation of N-methyl-D-aspartate (NMVDA) receptor and/or ryanodine receptor (RyR). Methods further comprise administering a therapeutically effective amount of a glutamate receptor antagonist to the subject.

17 Claims, 32 Drawing Sheets

(56) References Cited

OTHER PUBLICATIONS

Wei et. al., "Mechanisms of Dantrolene Neuroprotection in Alzheimer's Disease" Apr. 11, 2019, retrieved on Nov. 6, 2025 from https://grantome.com/grant/NIH/R01-AG061447-02 (Obtained from IDS) (Year: 2019).*

Peng et al., (2012), Neuroscience Letters 516 (2012) 274-279 (Year: 2012).*

European Search Report from European Patent Application No. EP 20833145.4 dated May 9, 2023.

International Preliminary Report on Patentability from PCT Application No. PCT/US2022/040198 dated Jan. 6, 2025.

Oules et al., "Ryanodine receptor blockade reduces amyloid-β load and memory impairments in Tg2576 mouse model of Alzheimer disease." Journal of Neuroscience 32.34 (2012): 11820-11834.

Singapore Search Report and Written Opinion from Singapore Application No. 11202114347V dated Jul. 3, 2024.

Wang et al. "Calcium Dysregulation in Alzheimer's Disease: A Target for New Drug Development." Journal of Alzheimer's Disease & Parkinsonism. 2017, 7(5), 1-7.

Bissonnette et al., "The controlled generation of functional basal forebrain cholinergic neurons from human embryonic stem cells." Stem cells 29.5 (2011): 802-811.

Bonora, et al. "Subcellular calcium measurements in mammalian cells using jellyfish photoprotein aequorin-based probes." Nature protocols 8.11 (2013): 2105-2118.

Fuchs et al. "Brain penetration of WEB 2086 (Apafant) and dantrolene in Mdr1a (P-glycoprotein) and Bcrp knockout rats." Drug Metabolism and Disposition 42.10 (2014): 1761-1765 (Abstract).

Hillman et al., "No improvement after chronic ibuprofen treatment in the 5XFAD mouse model of Alzheimer's disease." Neurobiology of aging 33.4 (2012): 833-e39 (Abstract).

Hollomon et al. "Knockdown of autophagy-related protein 5, ATG5, decreases oxidative stress and has an opposing effect on camptothecin-induced cytotoxicity in osteosarcoma cells." BMC cancer 13.1 (2013): 1-12.

International Search Report and Written Opinion from PCT Application No. PCT/US2022/040198 dated Jan. 6, 2022.

Lee et al., "Lysosomal proteolysis and autophagy require presenilin 1 and are disrupted by Alzheimer-related PS1 mutations." Cell 141.7 (2010): 1146-1158.

Liu et al., "Medial ganglionic eminence-like cells derived from human embryonic stem cells correct learning and memory deficits." Nature biotechnology 31.5 (2013): 440-447.

Oakley et al., "Intraneuronal β-amyloid aggregates, neurodegeneration, and neuron loss in transgenic mice with five familial Alzheimer's disease mutations: potential factors in amyloid plaque formation." Journal of Neuroscience 26.40 (2006): 10129-10140.

Peng et al., "Dantrolene ameliorates cognitive decline and neuropathology in Alzheimer triple transgenic mice." Neuroscience letters 516.2 (2012): 274-279.

Qiao et al. "Propofol affects neurodegeneration and neurogenesis by regulation of autophagy via effects on intracellular calcium homeostasis." Anesthesiology 127.3 (2017): 490-501.

Ren et al. "General anesthetics regulate autophagy via modulating the inositol 1, 4, 5-trisphosphate receptor: implications for dual effects of cytoprotection and cytotoxicity." Scientific reports 7.1 (2017): 1-12.

Shi et al., "Directed differentiation of human pluripotent stem cells to cerebral cortex neurons and neural networks." Nature protocols 7.10 (2012): 1836-1846.

Wu et al., et al. "Long term Dantrolene treatment reduced intraneuronal amyloid in aged Alzheimer triple transgenic mice." Alzheimer disease and associated disorders 29.3 (2015): 184.

Yang et al. "Simple behavioral assessment of mouse olfaction." Current protocols in neuroscience 48.1 (2009): 8-24.

Zhang et al., "Anesthetics isoflurane and desflurane differently affect mitochondrial function, learning, and memory." Annals of neurology 71.5 (2012): 687-698.

Wei, "Mechanisms of Dantrolene Neuroprotection in Alzheimer's Disease" Apr. 11, 2019 (Apr. 11, 2019, )retrieved on Sep. 11, 2020 from https:IIgrantome.comigrantiNIH/R01-AG061447-01; entire document, especially p. 1 para 1, p. 2 para 1.

Lanner et al., "Ryanodine Receptors: Structure, Expression, Molecular Details, and Function in Calcium Release", (2010), Cold Spring Harb Perspect Bioi 2010; 2:a003996; entire document, especially abstract.

International Search Report and Written Opinion from PCT Application No. PCT/US2022/040198 dated Nov. 3, 2020.

Kaiser et al., "Cerebrospinal fluid concentrations of functionally important amino acids and metabolic compounds in patients with mild cognitive impairment and Alzheimer's disease." Neurodegenerative Diseases 7.4 (2010): 251-259—Abstract.

Madeira, et al. "Elevated Glutamate and Glutamine Levels in the Cerebrospinal Fluid of Patients with Probable Alzheimer's Disease and Depression", Front. Psychiatry 2018, 9, 561 (8 pages).

Pomara, et al. "Glutamate and other CSF amino acids in Alzheimer's Disease", Am. J. Psychiatry 1992, 149, 2, 251-254.

* cited by examiner

INTRANASAL DANTROLENE ADMINISTRATION FOR TREATMENT OF ALZHEIMER'S DISEASE

CROSS-REFERENCE TO RELATED APPLICATIONS

This application is a National Phase Application of PCT International Application No. PCT/US2020/040198, International Filing Date Jun. 29, 2020, claiming the benefit of U.S. Patent Application(s) No(s). 62/868,820, filed Jun. 28, 2019, which is/are hereby incorporated by reference.

GOVERNMENT INTEREST STATEMENT

This invention was made with government support under Grant Numbers GM084979 and AG061447 awarded by the National Institutes of Health. The United States government has certain rights in the invention.

FIELD OF THE INVENTION

This invention relates to methods for treating Alzheimer's disease by intranasal dantrolene administration. This invention also relates to methods of inhibiting impaired neurogenesis and/or synaptogenesis in neurons in a subject with or suspected of having Alzheimer's Disease (AD), methods of improving and/or slowing the decline of cognitive function after onset of neuropathology and cognitive dysfunction, which neuropathology and cognitive dysfunction are caused by AD, methods of improving memory before onset of symptoms of AD, and methods of improving memory after onset of symptoms of AD, the methods comprising intranasally administering to a subject in need thereof an amount effective to inhibit over activation of ryanodine receptor (RyR) and/or N-methyl-D-aspartate (NMDA) receptor of a pharmaceutical composition comprising dantrolene.

BACKGROUND OF THE INVENTION

Alzheimer's disease (AD) is a devastating neurodegenerative disease. The deficit in the development of new drugs targeting the amyloid pathology over the past several decades warrants exploration of alternative pathways or mechanisms that could be the primary cause of AD cognitive dysfunction.

Sporadic AD (SAD) accounts for more than 95% of AD patients, but its pathology is largely unknown. Lack of understanding of the mechanisms and inadequate cell or animal models of SAD limit the development of new effective drugs to treat AD. Although the pathology and mechanisms of familial Alzheimer's Disease (FAD) have been relatively well studied, they have been primarily in cell and animal models, not in patients.

Dantrolene, which reduced mortality of malignant hyperthermia from 85% to below 5%, is the only FDA approved clinically available drug to treat this severe general anesthesia mediated complication. Chronic use of oral dantrolene is also utilized to treat muscle spasm, with relatively tolerable side effects. In light of the inadequacies of current drugs and therapies for AD, there exists a critical need for improved compositions and therapeutically effective methods of treating AD and dysfunctions present in and associated therewith, including but not limited to, impairment in neurogenesis and/or synaptogenesis in neurons of the brain, as well as loss in cognitive functions, both before and after onset of symptoms of AD.

SUMMARY OF THE INVENTION

In one aspect, this invention provides a method for inhibiting impaired neurogenesis and/or synaptogenesis in neurons in a subject with or suspected of having Alzheimer's Disease (AD), which impairment of neurogenesis and/or synaptogenesis is caused, at least in part, by over activation of endoplasmic reticulum (ER) ryanodine receptor (RyR), the method comprising intranasally administering to the subject an amount of a pharmaceutical composition comprising dantrolene effective to decrease release of ER calcium ions ($Ca^{2+}$) in cells derived from AD patients.

In another aspect, this invention provides a method for improving and/or slowing the decline of cognitive function after the onset of neuropathology and cognitive dysfunction, which neuropathology and cognitive dysfunction are caused by Alzheimer's Disease (AD), the method comprising intranasally administering to a subject in need thereof an amount of a pharmaceutical composition comprising dantrolene effective to inhibit over-activation of NMDA receptor and/or ryanodine receptor.

In a further aspect, this invention provides a method for improving memory before onset of symptoms of Alzheimer's Disease (AD), the method comprising intranasally administering to a subject in need thereof an amount of a pharmaceutical composition comprising dantrolene effective to inhibit over-activation of NMDA receptor and/or ryanodine receptor.

In another aspect, this invention provides a method for improving memory loss after onset of symptoms of Alzheimer's Disease (AD), which memory loss is caused by AD, the method comprising intranasally administering to a subject in need thereof an amount of a pharmaceutical composition comprising dantrolene effective to inhibit over-activation of NMDA receptor and/or ryanodine receptor.

In another aspect, this invention provides a method for increasing concentration and duration of dantrolene in the brain, the method comprising intranasally administering to a subject in need thereof an amount of a pharmaceutical composition comprising dantrolene.

In a further aspect, this invention provides a method for inhibiting impaired neurogenesis and/or synaptogenesis in neurons in a subject with or suspected of having Alzheimer's Disease (AD), wherein said impairment of neurogenesis and/or synaptogenesis is caused, at least in part, by over activation of endoplasmic reticulum (ER) ryanodine receptor (RyR), the method comprising: a) intranasally administering to said subject an amount of a pharmaceutical composition comprising dantrolene effective to decrease release of ER calcium ions ($Ca^{2+}$); and b) administering a therapeutically effective amount of a glutamate receptor antagonist to the subject of step (a).

Other features and advantages of this invention will become apparent from the following detailed description, examples and figures. It should be understood, however, that the detailed description and specific examples while indicating certain embodiments of the invention are given by way of illustration only, since various changes and modifications within the spirit and scope of the invention will become apparent to those skilled in the art from this detailed description.

BRIEF DESCRIPTION OF THE DRAWINGS

patients. FIG. 1A shows that treatment of iPSCs with dantrolene (DAN; 30 μM) for 24 h did not affect iPSCs from healthy human subjects (CON), but resulted in a significantly greater cell viability of iPSCs from sporadic Alzheimer's disease (SAD; P=0.006) and familial Alzheimer's disease (FAD; P<0.0001) patients. For cell viability, interaction, treatment and cell type were all significant sources of variation (F[2,40]=92.56, P<0.0001; F[1,40]=110.40, P<0.0001; and F[2,40]=92.81, P<0.0001, respectively). FIG. 1B shows that cell proliferation, measured by the percentage of bromodeoxyuridine (BrdU)-positive cells, was significantly impaired familial Alzheimer's disease cells compared with control healthy subject cells (P=0.022). Compared with vehicle control, dimethyl sulfoxide (DMSO), dantrolene resulted in a greater proliferation in familial Alzheimer's disease cells (P=0.008, familial Alzheimer's disease dantrolene to dimethyl sulfoxide). For proliferation, dantrolene treatment and cell type were significant sources of variation (F[2,30]=5.44, P=0.009; and F[1,30]=9.81, P<0.039, respectively). All data are expressed as the means±SD from five to eight independent experiments (in FIG. 1A, familial Alzheimer's disease, n=7; control, n=8; sporadic Alzheimer's disease, n=8; and in FIG. 1B, control treated with dimethyl sulfoxide, n=7; with dantrolene, n=5; sporadic Alzheimer's disease both DMSO and dantrolene group, n=5; familial Alzheimer's disease dimethyl sulfoxide, n=8; dantrolene, n=6). P<0.01; *P<0.001. Statistical significance was determined using two-way analysis of variance with Sidak's multiple comparisons tests (Sidak's MCT). MTT, 3-(4,5-dimethylthiazol-2-yl)-2,5-diphenyltetrazolium bromide.

FIG. 2A shows representative immunofluorescence images of stained immature neurons by doublecortin (DCX (red), treated with or without dantrolene for 3 days, starting on induction day 0 from induced pluripotent stem cells (iPSCs). Scale bar, 100 m. FIG. 2B shows differentiation of both sporadic Alzheimer's disease cells (P=0.004) and familial Alzheimer's disease cells (P=0.011) was impaired compared with controls (CON). However, the differentiation of both sporadic Alzheimer's disease (P=0.008) and familial Alzheimer's disease (P=0.008) cells was enhanced after treatment with dantrolene. Cell type and treatment were significant sources of variation (F[2,30]=8.749, P=0.001; and F[1,30]=25.08, P<0.0001, respectively) using two-way analysis of variance with Sidak's multiple comparisons tests. The data are represented by the means±SD from six independent experiments (n=6 for all groups). *P<0.05; **P<0.01. DAPI, 4',6-diamidino-2-phenylindole; DMSO, dimethyl sulfoxide.

FIG. 3A shows a differentiation timeline of NPC into mature cortical neurons. FIG. 3B shows representative immunofluorescence images of double-stained neurons with thyroid hormone receptor-b (Trb1, red) and microtubule-associated protein-2 (MAP2, green). Scale bar, 100 μM. FIG. 3C shows the percentage of Trb1 positive cells was significantly less in both human sporadic Alzheimer's disease (SAD; P<0.0001) and familial Alzheimer's disease (FAD) cells (P=0.022) compared with control healthy subjects (CON) cells, but the SAD cells had significantly greater percentage of TrB1 positive cells after treatment with dantrolene (DAN or Dan; P<0.0001). Interaction, cell type, and treatment were significant sources of variation (F[2,24]=14.84, P<0.0001; F[2,24]=15.94, P<0.0001; and F[1,24]=7.53, P=0.011, respectively). FIG. 3D shows a timeline for differentiation of neural progenitor cells (NPC) into mature BFCN neurons. FIG. 3E shows representative immunofluorescence images of double-stained mature neurons by MAP2 (red) and choline acetyltransferase (ChAT or CHAT)-positive cells (green), with or without dantrolene treatment for 3 days starting from the induction of induced pluripotent stem cells (iPSC) differentiation into neurons. Scale bars, 100 μM. FIG. 3F shows the percentage of ChAT-positive cells (basal forebrain cholinergic neurons (BFCN)) significantly decreased in both SAD (P=0.004) and FAD (P=0.017) cells, which was ameliorated by dantrolene treatment for FAD cells (P=0.008) but not SAD cells (P=0.067). Interaction, cell type, and treatment were significant sources of variation (F[2,24]=5.61, P=0.010; F[2,24]=6.27, P=0.006; and F[1,24]=14.78, P=0.001, respectively). Statistical significance was determined using two-way analysis of variance (ANOVA) followed by Sidak's multiple comparisons test. All data are represented as the mean±SD from five independent experiments (n=5 for all groups). *P<0.05; P<0.01; **P<0.0001. DMSO, dimethyl sulfoxide; SHH, Recombinant Human Sonic Hedgehog.

FIG. 4A shows the number of intersections were significantly less in both sporadic Alzheimer's disease (SAD) and familial Alzheimer's disease (FAD) cells, which was inhibited by dantrolene in SAD cells. FIG. 4B shows the mean number of intersections at the distance around 150 μM from soma were less in SAD (p<0.0001) and FAD cells (p<0.0001) compared with controls (CON), but were significantly greater in both SAD (p<0.0001) and FAD cells (P=0.014) with dantrolene treatment. Interaction (F[2,12]=42.18, P<0.0001), cell type (F[2,12]=273.30, P<0.0001), and dantrolene treatment (F[1,12]=78.48, P<0.0001) were significant sources of variation. Statistical significance was determined by two-way analysis of variance and Sidak's multiple comparisons test. FIG. 4C shows synaptic density determined by postsynaptic marker density protein 95 (PSD95; red) and presynaptic marker synapsin-1 (green) double immunostaining. Scale bar, 100 μM. FIG. 4D shows PSD95 density was significantly less in both SAD (P=0.001) and FAD cells (P=0.001) compared with controls but was significantly greater in FAD cells (P<0.0001) with dantrolene treatment. Interaction (F[2,23]=8 0.78, P=0.002), cell type (F[2,23]=25.36, P<0.0001), and dantrolene treatment (F[1,23]=28.60, P<0.0001) were significant sources of variation. FIG. 4E shows synpapsin-1 was also significantly less in SAD (P=0.001) and FAD p<0.0001) cells and was significantly increased by dantrolene in FAD cells (p<0.0001) and was significantly greater in FAD cells treated with dantrolene (P<0.0001). Interaction (F[2,23]=18.12, P<0.0001), cell type (F[2,23]=21.46, P<0.0001), and dantrolene treatment (F[1,23]=7.18, P=0.013) were significant sources of variation. The data are represented by the means±SD from at least four independent experiments: controls and FAD cells (N=5) and SAD cells (N=4). *P<0.05; P<0.01; *P<0.001; ****P<0.0001. Statistical significance was determined by two-way analysis of variance and Sidak's multiple comparisons test. DMSO, dimethyl sulfoxide.

FIGS. 5A-5B show Type 2 ryanodine receptors (RyR, RyR-2, or RYR-2) RyR-2s increased in both SAD and FAD cells, and dramatically more in FAD cells from patients, determined by immunoblotting (Western Blot). FIGS. 5C and 5D similarly show RyR-2 was significantly greater in SAD cells determined by immunofluorescence staining. All data are Mean±SD from four independent experiments (N=4 replicates, FIG. 5B) or 7 independent experiments (N=7 replicates, FIG. 5D). The data in FIG. 5B was nonparametric (D'Agostino-Pearson omnibus normality test) and analyzed by Kruskall-Wallis test (P=0.132) followed by Dunn's multiple comparison test (P=0.158) compared to control healthy subjects (CON) cells. The data in FIG. 5D was also nonparametric and was analyzed by Kruskal-Wallis test (P=0.002) followed by Dunn's multiple comparison test (Dunn's MCT). *P=0.020; P=0.002. Scale bar, m (FIG. 5**C). DAPI, 4',6-diamidino-2-phenylindole.

FIGS. 6A-6D) in sporadic (SAD) and familial (FAD) Alzheimer disease cells (P=0.041 for sporadic Alzheimer's disease, P=0.008 for familial Alzheimer's disease respectively) compared with normal human subjects (CON). Dantrolene (DAN, 30 μM) ameliorated the NMDA-mediated elevation of $[Ca^{2+}]_c$ and AUC in familial Alzheimer's disease cells (P=0.436 for peak, P<0.0001 for AUC, respectively; FIGS. 6B, 6D). All data are expressed as medians [25th, 75th] from three independent experiments (N=3). The data in FIG. 6C were nonparametric and analyzed by the Kruskall-Wallis test (P=0.020) followed by Dunn's multiple comparison test. The data for FIG. 6D were also nonparametric and analyzed using the Kruskal-Wallis test (P<0.001) followed by Dunn's multiple comparison test. *P=0.041, P=0.008, **P<0.0001.

FIGS. 7A, 7E), was a significant source of variation (F[1,35]=14.90, P=0.0005) for the peak cytosolic $Ca^{2+}$ concentrations $[Ca^{2+}]_c$ which were significantly higher in sporadic Alzheimer disease cells (P=0.049) compared with control cells. ATP, in the absence of 1 mM extracellular $Ca^{2+}$ (ATP), resulted in a significantly lower ATP-induced peak $[Ca^{2+}]_c$ in familial Alzheimer's disease cells (P=0.031) compared with familial Alzheimer's disease cells in the presence of 1 mM extracellular $Ca^{2+}$ (ATP+$Ca^{2+}$). (FIGS. 7B, 7E) Furthermore, ATP with extracellular calcium (ATP+$Ca^{2+}$) was a significant source of variation (F[1,35]=71.87, P<0.0001) for the integrated cytosolic $Ca^{2+}$ (area under the curve [AUC]), which was significantly greater for control (P=0.0002), sporadic Alzheimer's disease (P=0.005), and familial Alzheimer's disease (P<0.0001) cells compared with the same cells with ATP alone (ATP; E). Dantrolene (DAN, 30 μM) pretreatment of cells with ATP plus extracellular $Ca^{2+}$ (ATP+$Ca^{2+}$+DAN) was a significant source of variation for Alzheimer's disease cell type (F[2,42]=3.65, P=0.035) for the peak cytosolic [$Ca^{2+}$]C, although no significant differences were detected between the groups (FIGS. 7C, 7F). The addition of dantrolene (ATP+$Ca^{2+}$+DAN) was also a significant source of variation (F[1,40]=30.60, P<0.0001) for Alzheimer's disease cell type for the AUC, which was significantly reduced for the controls (P=0.033) and familial Alzheimer's disease cells (P=0.015) compared with cells with just ATP+$Ca^{2+}$ (FIGS. 7C, 7F). Dantrolene (30 μM) pretreatment of the cells with ATP in the absence of extracellular $Ca^{2+}$ (ATP+DAN; D) was a significant source of variation (F[1,33]=10.01, P=0.003) on the peak cytosolic $[Ca^{2+}]_c$, though no significant differences were found between the groups (FIG. 7G), and the absence of $Ca^{2+}$ was a significant source of variation (F[1,33]=5.95, P=0.020) on the AUC with no differences detected between groups (FIG. 7G). Peak and integrated $Ca^{2+}$ concentrations are shown as percentages of baseline from CON cells from normal human subjects. All data (FIGS. 7E-7G) are expressed as the means±SD from at least five independent experiments (CON, n=6 replicates; sporadic Alzheimer's disease, n=5 replicates; familial Alzheimer's disease, n=8-9 replicates). *P<0.05; P<0.01; *P<0.001. Significance was determined by two-way analysis of variance followed by Sidak's multiple comparisons tests.

FIG. 8A shows colocalization of vacuolar-type H+-ATPase (V-ATPase; red) was measured using immunostaining with specific markers targeting lysosomes (LAMP-2, green), endosomes (EEA, green), and endoplasmic reticulum (Calnexin, green), in induced pluripotent stem cells (iPSC) of healthy human subjects (CON), sporadic (SAD) or familial (FAD) Alzheimer's disease patients. FIG. 8B shows cell acidity was measured by lysotracker-positive acidic vehicles (red) in CON, SAD, and FAD cells (4',6-diamidino-2-phenylindole [DAPI], blue). FIG. 8C shows V-ATPase in lysosomes (LAMP-2) was significantly lower in SAD cells (P=0.001) and FAD cells (P=0.010) than controls. There was significant source of variation for interaction (F[4,23]=4.35, P=0.008) and organelle type (F[2,23]=29.15, P<0.0001). FIG. 8D shows that with the addition of dantrolene (DAN, 30 μM), V-ATPase in lysosomes (LAMP-2) in FAD cells was no longer significantly reduced (P=0.965) but remained significantly lower in SAD cells (P=0.007) compared with controls. In addition, v-ATPase in the endoplasmic reticulum (calnexin) of the controls was significantly reduced compared with SAD (P=0.001) and FAD (P<0.0001) cells. There was significant source of variation for interaction (F[4,27]=8.66, P=0.0001), organelle type (F[2,27]=79.49, P<0.0001), and cell type (F[2,27]=5.96, P=0.007). FIG. 8E shows lysotracker-positive acidic vesicles were significantly lower in sporadic Alzheimer's disease (P<0.0001) and familial Alzheimer's disease (P=0.0004) compared with control cells. Dantrolene also significantly increased tracker-positive acidic vesicles in both sporadic Alzheimer's disease (P=0.025) and familial Alzheimer's disease (P=0.036) cells compared with dimethyl sulfoxide (DMSO). Cell type and dantrolene were significant sources of variation (F[2,19]=29.88, P<0.0001; and F[1,19]=23.16, P=0.0001, respectively). All data are expressed as the means±SD from four independents (n=4 replicates for all groups) and were analyzed by two-way analysis of variance followed by Sidak's multiple comparisons test. *P<0.05; P<0.01; *P<0.001; ****P<0.0001.

FIGS. 9A, 9C show representative immunohistochemical images (FIG. 9A) and representative Western blots (FIG. 9C) of LC3II (red) in lysosomes (LAMP2, green) in induced pluripotent stem cells (iPSC) from sporadic Alzheimer disease (SAD), familial Alzheimer disease (FAD) and healthy human controls (CON) with dimethyl sulfoxide (DMSO), dantrolene (DAN), or dantrolene plus bafilomycins (BAFI). FIG. 9B shows quantitation of the double-labeled immunostained cells showed that dantrolene with bafilomycins significantly increased LC3II in lysosomes (LAMP-2) in SAD (P<0.0001), FAD (P<0.0001), and CON (P<0.0001) cells compared with dimethyl sulfoxide or dantrolene, respectively. There were significant sources of variation in interaction (F[4,35]=8.18, P<0.0001), cell type (F[2,35]=24.08, P<0.0001), and treatment (F[2,35]=177.00, P<0.0001) using two-way analysis of variance and Sidak's multiple comparisons test. FIG. 9D shows that quantitation of Western blots similarly showed that dantrolene with bafilomycins resulted in significantly increased LC3II in lysosomes (LAMP-2) in SAD (P<0.0001), FAD (P<0.0001), and CON (P<0.0001) cells compared with DMSO or DAN alone, respectively. Familial Alzheimer's disease cells treated with dantrolene also had significantly increased LC3II (P=0.0004) compared with familial Alzheimer's disease treated with dimethyl sulfoxide cells. Interaction (F[4,18]=6.92, P=0.002) and treatment (F[2,18]=303.40, P<0.001) were significant sources of variation using two-way analysis of variance and Sidak's multiple comparisons test. FIG. 9E shows representative Western blot of P62 levels in CON, SAD and FAD cells. FIG. 9F shows that quantitation of P62 Western blots found that this marker of cellular stress is significantly increased in FAD cells (P=0.015) compared with CON using the Kruskal-Wallis test (P=0.004) followed by Dunn's multiple comparison test. All data are expressed as the mean±SD from at least three independent experiments (n=3 replicates for all groups). *P<0.05; P<0.01; * P<0.001; ****P<0.0001.

FIG. 10A shows the peak dantrolene plasma concentration ($C_{max}$) occurred at 20 minutes after intranasal administration (5 mg/kg) and at 50 minutes after oral administration (5 mg/kg). *p=0.0000089 compared to oral administration determined with multiple t-tests using the Sidak-Holm method, alpha=0.05%. Intranasal time points, 10, 30, 150, 180 min, n=5; 20 min, n=8; 50-120 min, n=4; oral time points, 10-120 min; n=5. FIG. 10B shows a comparison of integrated dantrolene exposure (areas under the curves of panel A) (left) and Cmax (right) in plasma after intranasal and oral administration of dantrolene, p=0.0079 with the nonparametric unpaired Mann-Whitney test (two-tailed). Nasal Plasma (20 min), n=8; Oral Plasma, (50 min), n=4; FIG. 10C shows the brain concentration of dantrolene after intranasal administration (5 mg/kg) was greater than after oral administration at most time points. The Cmax occurred at 20 minutes after intranasal administration and 50 minutes after oral administration, respectively. *p=0.00000012, p=0.0035 (30 min), p=0.0037 (50 min), p=0.0027 (120 min), compared to contrast group (intranasal vs. oral) and determined with multiple t-tests using the Sidak-Holm method, alpha=0.05%. Intranasal time points, 10, 30, 150, 180 min, n=5; 20 min, n=8; 50-120 min, n=4; oral time points, 10-120 min; n=5. FIG. 10D shows a comparison of integrated dantrolene exposure in brain tissue after intranasal and oral administration of dantrolene (areas under the curves of panel C) (left) and Cmax in brain (right) after intranasal and oral administration of dantrolene, **p=0.0079 with the nonparametric unpaired Mann-Whitney test (two-tailed). Nasal Brain and Oral Brain, n=5; Nasal Brain (20 min), n=8; Oral Brain (50) min, n=5. All data are expressed as Mean±95% CI.

FIG. 12A shows that after 3 weeks of intranasal administration of dantrolene (5 mg/kg, 3 times/wk) or vehicle control, olfaction was measured by the time in seconds (s) necessary for the animal to retrieve the buried food with its front paws. FIG. 12B shows that after 4 months of intranasal administration of dantrolene (5 mg/kg, 3 times/wk), motor function was determined by the length of time to find food (FIG. 12A) and by length of time spent on the rotarod (FIG. 12B). No significant differences were detected in olfaction or motor function. Data are expressed as the Mean±95% CI, analyzed with the nonparametric unpaired Mann-Whitney test, n=10 for all groups.

FIG. 15A shows dantrolene concentrations in plasma 20 and 60 min after subcutaneous (blue) or intranasal (red) administration in B6SJLF1/J mice. A two-way analysis of variance showed a significant source of variation in both time (p=0.015; F(1, 16)=7.427) and administration route (p=0.0004; F(1, 16) 19.75). Dantrolene concentration in the plasma was significantly greater at 20 min for subcutaneous administration (p=0.0014) with Sidak's multiple comparisons. FIG. 15B shows brain dantrolene concentrations after the subcutaneous and intranasal approach. A two-way analysis of variance showed a significant source of variation for the route of administration (p<0.0001; F(1, 16)=27.07) and that dantrolene concentration in the brain was significantly greater at 60 min. for intranasal administration than subcutaneous administration (p=0.0002) with Sidak's multiple comparisons. FIG. 15C shows dantrolene brain/plasma concentration ratio, representing dantrolene's ability to penetrate the brain. A two-way analysis of variance showed a significant source of variation for the route of administration (p<0.0001; F(1, 16)=43.65), and that the brain/plasma ratio was significantly greater at both 20 min (p=0.0032) and 60 min (p<0.0001) for intranasal administration, with Sidak's multiple comparisons. FIG. 15D shows the area under the curve (AUC) of dantrolene concentrations calculated using Linear Trapezoidal Method to reflect the integrated overall dantrolene exposure. All data are presented as Mean with 95% CI, N=5/group for all groups, p<0.01, *p<0.001, ****p<0.0001.

FIG. 16A shows that with the CFC test, at 6 months of age, all ETG 5XFAD mice, including intranasal administration of vehicle (IN-VEH), dantrolene (IN-DAN), and subcutaneous injection of dantrolene (SQ-DAN), showed significantly greater memory compared to untreated 5XFAD controls (CON) (p=0.0004; p=0.0002; p<0.0001, respectively). The memory of 5XFAD mice at 11 months of age in the IN-VEH and IN-DAN ETG 5XFAD mice (p=0.0246, p=0.0228, respectively) was significantly greater than 5XFAD controls. The ETG data were analyzed using two-way analysis of variance with Dunnett's multiple comparison test (MCT). Treatment was found to be a significant source of variation (p<0.0001; F(3,49)=9.536). At 11 months of age, LTG (11M-LTG) IN-DAN and SQ-DAN were compared to 5XFAD control (CON) and the data were analyzed using the Kruskal-Wallis test with Dunn's MCT. The memory of the In-DAN group was significantly improved compared to CON (p=0.0410). The memory of the SQ-DAN trended to be better but was not statistically significant (p=0.1575). FIG. 16B similarly shows that hippocampus-independent memory (FC-cued), at 6 months of age, was significantly improved in the ETG with IN-VEH (p=0.0145), IN-DAN (p=0.0055), and SQ-DAN (p=0.001) compared to controls. At 11 months of age, the memory of the IN-DAN ETG was significantly better (p=0.0011) than the 5XFAD CON group, analyzed using a two-way analysis of variance with Dunnett's multiple comparison test (MCT). Treatment was found to be a significant source of variation (p=0.0013; F (3,49)=6.095). IN-VEH or SQ-DAN in the ETG trended to improve memory but were not statistically different (p=0.0664, p=0.1843, respectively). No significant memory improvement was detected at 11 months in the IN-DAN or SQ-DAN LTGs compared to 5XFAD CON using the Kruskal-Wallis test with Dunn's MCT. All data are presented as Mean with 95% CI, *p<0.05, p<0.01, *p<0.001, ****p<0.0001, compared to 5XFAD CON. Animal numbers, ETG 6M: CON n=13, IN-VEH n=12, IN-DAN n=14, IN-SQ n=14; ETG 11M: CON n=13, IN-VEH n=10, IN-DAN n=11, IN-SQ n=9; LTG 11M: IN-DAN n=13, SQ-DAN n=14, CON=13, same controls as shown for ETG 11M).

FIG. 17A shows motor function, which was measured using the rotarod test for all groups at 9 months of age. No significant differences between the treatment groups and the control group were detected with one-way analysis of variance and Dunnett's multiple comparison test (MCT). (ETG:CON n=13, IN-VEH n=10, IN-DAN n=11, SQ-DAN n=9; LTG: IN-DAN n=13, SQ-DAN n=15.) FIG. 17B shows olfaction, which was measured using the buried food test for all groups at 10 months of age. No significant differences were found with the Kruskall-Wallis test for nonparametric data and Dunn's MCT. (ETG:CON n=13, IN-VEH n=10, IN-DAN n=10, SQ-DAN n=9; LTG: IN-DAN n=13, SQ-DAN n=15.) FIG. 17C shows liver function, which was evaluated by measuring plasma alanine aminotransferase (ALT) activity. ALT was significantly increased after 6-month intranasal treatment in LTG compared to control group (p=0.0364). No significant differences were detected between other treatment groups and the control group with the Kruskall-Wallis test for nonparametric data and Dunn's MCT. (ETG: CON n=9, IN-VEH n=9, IN-DAN n=8, SQ-DAN n=8, LTG: IN-DAN n=9, SQ-DAN n=7). All data are presented as Mean with 95% CI. FIG. 17D shows hepatic pathology, which was examined at 11 months of age in H&E stained sections of the ETG mice. No gross differences were observed between ETG groups (3 sections/animal: CON n=3, IN-VEH n=3, IN-DAN n=3, SQ-DAN n=3, bar=50 μm). FIG. 17E shows mortality after chronic treatment (ETG, LTG) with dantrolene (IN-DAN, SQ-DAN) or vehicle (IN-VEH), which was compared to untreated 5XFAD controls using the Log-rank (Mantel-Cox) test. No significant difference between dantrolene and vehicle treatments was detected (p=0.3636). FIG. 17F shows bodyweight, which was monitored during the treatment. No significant differences were detected in the growth curve for the 5XFAD mice in the ETG groups (p=0.1478) using repeated measures two-way analysis of variance. (ETG: CON n=13, IN-VEH n=10, IN-DAN n=11, SQ-DAN n=9; LTG: IN-DAN n=14, SQ-DAN n=14.) All data are presented as Mean with 95% CI.

FIGS. 18A-18B show representative micrographs of 6E10 immunoreactivity in the hippocampus and cortex of 5XFAD mice in the Early Treatment Group (ETG) and Late Treatment Group (LTG) for (CON), intranasal vehicle (IN-VEH), intranasal dantrolene (IN-DAN), and subcutaneous dantrolene (SQ-DAN) treatments. (Bar=100 μm). FIGS. 18C and 18E show the percent area of the hippocampus and cortex occupied by plaques for each test group. No significant differences were found between the treatment groups and control. FIGS. 18D and 18F similarly show the number of amyloid plaques per area ($mm^2$), calculated in the hippocampus and cortex for each test group. No significant differences were found. All data were analyzed with the Kruskall-Wallis test for nonparametric data and Dunn's MCT. (3 sections/animal; DG and HIP, ETG: CON n=8, IN-VEH n=4, IN-DAN n=6, SQ-DAN n=6; LTG: IN-DAN n=6, SQ-DAN n=7). Data are presented as Mean with 95% CI. FIG. 19A shows for CFC, hippocampal-dependent memory was significantly impaired in 5XFAD (TG) mice compared to wild-type (WT) mice at 6 and 11 months of age (P=0.0015, P=0.0033 respectively), which was analyzed using an unpaired t-test. Genetics (WT versus TG) were found a significant source of variation for impaired memory (P<0.0001, F(1,47)=23.44).

FIG. 20A shows no significant differences in the CFC test at both 6 and 11 months of age, including intranasal administration of vehicle (IN-VEH), dantrolene (IN-DAN) and subcutaneous injection of dantrolene (SQ-DAN), compared to the untreated controls. The ETG data at these 2 ages were analyzed using the two-way analysis of variance with Dunnett's multiple comparison test (MCT). The LTG data at 11 months of age were analyzed using a one-way analysis of variance with Tukey's MCT. FIG. 20B similarly shows no significant differences in all ETG and LTG groups in hippocampal-independent memory (FC-cued) at both ages. The ETG data at these 2 ages were analyzed using two-way analysis of variance with Dunnett's multiple comparison test (MCT). The LTG data at 11 months were analyzed using a one-way analysis of variance with Tukey's MCT. All data are presented as Mean with 95% CI. ETG 6M: CON n=13, IN-VEH n=15, IN-DAN n=18, SQ-DAN n=15; ETG 11M: CON n=12, IN-VEH n=12, IN-DAN n=17, SQ-DAN n=13; LTG 11M: IN-DAN n=13, SQ-DAN n=13.

FIGS. 21A-21B show the latency to locate the platform in all groups did not significantly decrease over 5 consecutive days during the cue trials suggesting that the mice did not have vision impairment or swimming difficulties. FIGS. 21C-21D show the latency to locate the platform in all groups did not significantly decrease over 5 consecutive days during the place trials for determining spatial learning ability. FIG. 21E shows there were no significant differences in the percent time (probe trial) that the mice spent in the target quadrant for all groups compared to controls. FIG. 21F shows there were no significant differences in the number of times the animals crossed the platform for all groups. The data were analyzed using a one-way analysis of variance with Sidak's MCT. All data are presented as Mean with 95% CI. Animal numbers, WT groups: ETG: CON n=14, IN VEH n=8, IN-DAN n=12, SQ-DAN n=13, LTG: IN-DAN n=14, SQ-DAN n=13; TG groups: ETG: CON n=13, IN-VEH n=10, IN-DAN n=10, SQ-DAN n=9, LTG: IN-DAN n=14, SQ-DAN n=14.

FIG. 22A shows motor function measured using the rotarod test for all groups at 10 months of age. No significant differences were detected between the treatment and control groups with the one-way analysis of variance and Dunnett's multiple comparison test (MCT). (ETG: CON n=14, IN-VEH n=12, IN-DAN n=17, SQ-DAN n=14; LTG: IN-DAN n=15, SQ-DAN n=13.) FIG. 22B shows olfaction was measured using the buried food test for all groups at 10 months of age. No significant differences were found with the Kruskall-Wallis test for nonparametric data and Dunn's MCT. (ETG: CON n=14, IN-VEH n=8, IN-DAN n=12, SQ-DAN n=14; LTG: IN-DAN n=15, SQ-DAN n=13.) FIG. 22C shows liver function was evaluated for the ETG and LTG by measuring plasma alanine aminotransferease (ALT) activity. ALT was significantly increased after 6-month subcutaneous treatment in LTG compared with control group using one-way analysis of variance with Dunnett's MCT (p=0.0142). No significant difference was detected in other treatment group compared with control group with one-way analysis of variance with Dunnett's MCT. (ETG: CON n=7, IN-VEH n=8, IN-DAN n=8, SQ-DAN n=9, LTG: IN-DAN n=8, SQ-DAN n=7). All data is presented as Mean with 95% CI. FIG. 22D shows hepatic pathology was examined at 11 months of age in H&E stained sections of the ETG mice. No gross differences were observed between ETG groups (3 sections/animal; CON n=3, IN-VEH n=3, IN-DAN n=3, SQ-DAN n=3, bar=50 m). FIG. 22E shows mortality after chronic treatment of dantrolene (IN-DAN, SQ-DAN) and vehicle (IN-VEH) in ETG and LTG mice compared to wild-type controls (WT CON) using Log-rank (Mantel-Cox) test. No significant differences were found (P=0.2388). FIG. 22F shows body weight was assessed at 12 months of age before the animals were euthanized. No significant difference was detected with the one-way analysis of variance and Dunnett's MCT. (ETG: CON n=13, IN-VEH n=12, IN-DAN n=16, SQ-DAN n=13; LTG: IN-DAN n=13, SQ-DAN n=13.) All data is presented as Mean with 95% CI.

FIGS. 24A-24B show synaptic function, which was determined by expression PSD95 and synapsin1 using Western blot. FIGS. 24C-24D show no significant differences were detected in all groups compared with controls with the one-way analysis of variance and Dunnett's MCT. N=3 in each group. All data is presented as Mean with 95% CI.

DETAILED DESCRIPTION OF THE INVENTION

Figures 1A, 1B:
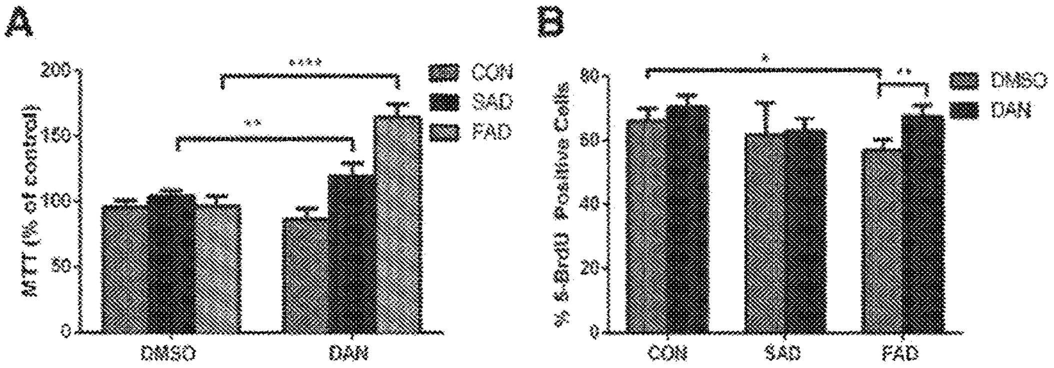
FIGS. 1A-1B show dantrolene promoted cell viability and inhibited impairment of cell proliferation in induced pluripotent stem cells (iPSCs) from Alzheimer's disease (AD)

The present invention may be understood more readily by reference to the following detailed description which forms a part of this disclosure. It is to be understood that this invention is not limited to the specific methods, products, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with this application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In this disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality," as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

In one aspect, this invention provides a method for inhibiting impaired neurogenesis and/or synaptogenesis in neurons in a subject with or suspected of having Alzheimer's Disease (AD), which impairment of neurogenesis and/or synaptogenesis is caused, at least in part, by over activation of endoplasmic reticulum (ER) ryanodine receptor (RyR), the method comprising intranasally administering to the subject an amount effective to decrease release of ER calcium ions ($Ca^{2+}$) of a pharmaceutical composition comprising dantrolene. In an embodiment, the neurogenesis comprises neurogenesis from neuroprogenitor cells (NPCs) into immature neurons, followed by neurogenesis from immature neurons into cortical neurons. In certain embodiments, the synaptogenesis occurs in cortical neurons. In some embodiments, the cortical neurons are cholinergic neurons. In various embodiments, the cortical neurons are basal forebrain cholinergic neurons (BFCN) neurons, prefrontal cortex neurons, hippocampus neurons, or a combination thereof. In an embodiment, the AD is familial Alzheimer's disease (FAD). In another embodiment, the AD is sporadic Alzheimer's disease (SAD). In particular embodiments, the RyR is Type 2 RyR (RyR-2). In particular embodiments, the RyR is Type 1 RyR (RyR-1). In particular embodiments, the RyR is Type 3 RyR (RyR-3). In particular embodiments, the RyR is a combination of RyR subtypes, e.g., RyR-1, RyR-2, RyR-3, including all RyR subtypes. In various embodiments, the over activation of endoplasmic reticulum (ER) ryanodine receptor (RyR) elevates mitochondrial calcium resulting in decrease of ATP. In particular embodiments, the intranasal administration of dantrolene reduces the elevated mitochondrial calcium and increases cytosolic ATP. In some embodiments, the pharmaceutical composition comprising dantrolene is administered daily. In some embodiments, the pharmaceutical composition comprising dantrolene is administered three times per week. In some embodiments, the pharmaceutical composition comprising dantrolene is administered one time per week. In various embodiments, the pharmaceutical composition comprising dantrolene is administered for four months to one year. In some embodiments, the pharmaceutical composition comprising dantrolene is administered for four to six months. In certain embodiments, the pharmaceutical composition comprising dantrolene is administered for up to four months. In various embodiments, the pharmaceutical composition comprising dantrolene is administered for longer than one year. In various embodiments, the pharmaceutical composition comprising dantrolene is administered for up to two years. In various embodiments, the pharmaceutical composition comprising dantrolene is administered for longer than two years. In the various embodiments of the provided methods for inhibiting impaired neurogenesis and/or synaptogenesis in neurons in a subject with or suspected of having AD, the intranasal administration of the pharmaceutical composition comprising dantrolene does not impair olfactory function, motor function, or liver function of the subject.

In another aspect, this invention provides a method for improving and/or slowing the decline of cognitive function after onset of neuropathology and cognitive dysfunction, which neuropathology and cognitive dysfunction are caused by Alzheimer's Disease (AD), the method comprising intranasally administering to a subject in need thereof an amount effective to inhibit over-activation of NMDA receptor and/or ryanodine receptor of a pharmaceutical composition comprising dantrolene. In particular embodiments, the cognitive function is memory, learning, thinking, attention, perception, language use, reasoning, decision making, problem solving or a combination thereof. In some embodiments, the AD is familial Alzheimer's disease (FAD). In various embodiments, the AD is sporadic Alzheimer's disease (SAD). In particular embodiments, the RyR is Type 2 RyR (RyR-2). In particular embodiments, the RyR is Type 1 RyR (RyR-1). In particular embodiments, the RyR is Type 3 RyR (RyR-3). In particular embodiments, the RyR is Type 3 RyR (RyR-3). In particular embodiments, the RyR is a combination of RyR subtypes, e.g., RyR-1, RyR-2, RyR-3, including all RyR subtypes. In some embodiments, the pharmaceutical composition comprising dantrolene is administered daily. In some embodiments, the pharmaceutical composition comprising dantrolene is administered three times per week. In some embodiments, the pharmaceutical composition comprising dantrolene is administered one time per week. In various embodiments, the pharmaceutical composition comprising dantrolene is administered for four months to one year. In some embodiments, the pharmaceutical composition comprising dantrolene is administered for four to six months. In certain embodiments, the pharmaceutical composition comprising dantrolene is administered for up to four months. In various embodiments, the pharmaceutical composition comprising dantrolene is administered for longer than one year. In various embodiments, the pharmaceutical composition comprising dantrolene is administered for up to two years. In various embodiments, the pharmaceutical composition comprising dantrolene is administered for longer than two years. In the various embodiments of the provided methods for improving and/or slowing the decline of cognitive function after onset of neuropathology and cognitive dysfunction, which neuropathology and cognitive dysfunction are caused by AD, intranasal administration of the pharmaceutical composition comprising dantrolene does not impair olfactory function, motor function, or liver function of the subject.

In certain embodiments, cognitive dysfunction is short-term or long-term memory loss, learning difficulty, thinking difficulty, attention/concentration difficulty, perception difficulty, difficulty in language use, reasoning difficulty, difficulty in making decisions/impaired judgment, problem solving difficulty, confusion, poor motor coordination, or a combination thereof. In particular embodiments, the memory loss is hippocampal-dependent and hippocampal-independent memory loss. In various embodiments, the neuropathology is amyloid accumulation between brain neurons.

In some embodiments of the method for improving and/or slowing the decline of cognitive function after onset of neuropathology and cognitive dysfunction, which neuropathology and cognitive dysfunction are caused by AD, the method further comprises administering a therapeutically effective amount of a glutamate receptor antagonist to the subject. In some embodiments of the method, the method further comprises (a) obtaining cerebrospinal fluid (CSF) from the subject before intranasally administering to the subject the pharmaceutical composition comprising dantrolene; and (b) determining a level of glutamate in the CSF, wherein a determined level of glutamate in step (b) that is higher than a level of glutamate in CSF obtained from a control subject is indicative of suitability of the subject for treatment with dantrolene. In some embodiments, the intranasal administration of the pharmaceutical composition comprising dantrolene does not impair olfactory function, motor function, or liver function of the subject.

In some embodiments, the method further comprises obtaining CSF from the subject before administering the therapeutically effective amount of the glutamate receptor antagonist; and determining a level of glutamate in the CSF, wherein a determined level of glutamate that is higher than a level of glutamate in CSF obtained from a control subject is indicative of suitability of the subject for treatment with a glutamate receptor antagonist.

In particular embodiments, the glutamate receptor antagonist is an agent that blocks the NMDA receptor by competitive antagonism at a glutamate-binding site or is an agent that blocks the NMDA receptor by noncompetitive antagonism at a glycine, phencyclidine and/or magnesium binding site. In some embodiments, the agent that blocks the NMDA receptor by competitive antagonism at a glutamate-binding site is selfotel (CGS 19755) aptiganel (CNS 1102), CGP 37849, APV or AP-5 (R-2-amino-5-phosphonopentanoate), 2-amino-7-phosphono-heptanoic acid (AP-7), 3-[(R)-2-carboxypiperazin-4-yl]-prop-2-enyl-1-phosphonic acid (CP-Pene) and/or aspartame. In some embodiments, the agent that blocks the NMDA receptor by noncompetitive antagonism at a phencyclidine (PCP), magnesium, and/or MK-801 (dizocilpine) binding site is memantine, ketamine, phencyclidine, 3-MEO-PCP, 8A-PDHQ, amantadine, atomoxetine, AZD6765, agmatine, delucemine, delucemine, dextrallorphan, dextromethorphan, dextrorphan, diphenidne, ethanol, eticylidine, gacyclidine, methoxetamine (MXE), minocycline, nitromemantine, nitrous oxide, PD-137889, rolicyclidine, tenocyclidine, nethoxydine, tiletamine, neramexane, eliprodil, etoxadrol, dexoxadrol, WMS-2539. NEFA, remacemide, magnesium sulfate, aptiganel, HU-211, huperzine A, Dipeptide D-Phe-L-Tyr, Ibogaine, Apocynaceae, Remacemide, Rhynchophylline, gabapentin, or dizocilpine (MK-801). In some embodiments, the agent that blocks the NMDA receptor by noncompetitive antagonism at a glycine binding site is (GLYX-13), NRX-1074, 7-Chlorokynurenic acid, 4-Chlorokynurenine (AV-101), 5,7-Dichlorokynurenic acid, Kynurenic acid, TK-40 (competitive antagonist at the GluN1 glycine binding site), 1-aminocyclo-propanecarboxylic acid (ACPC), L-Phenylalanine, or Xenon.

In another aspect, this invention provides a method for improving memory before onset of symptoms of Alzheimer's Disease (AD), the method comprising intranasally administering to a subject in need thereof an amount effective to inhibit over-activation of NMDA receptor and/or ryanodine receptor of a pharmaceutical composition comprising dantrolene. In some embodiments of the provided methods for improving memory before onset of symptoms of AD, the intranasal administration of the pharmaceutical composition comprising dantrolene does not impair olfactory function, motor function, or liver function of the subject. In particular embodiments, the symptoms of AD are neuropathology, cognitive dysfunction or a combination thereof. In various embodiments, the cognitive dysfunction is short-term or long-term memory loss, learning difficulty, thinking difficulty, attention/concentration difficulty, perception difficulty, difficulty in language use, reasoning difficulty, difficulty in making decisions/impaired judgment, problem solving difficulty, confusion, poor motor coordination, or a combination thereof. In an embodiment, the memory loss is hippocampal-dependent and hippocampal-independent memory loss. In some embodiments, the neuropathology is amyloid accumulation between brain neurons. In some embodiments, the AD is familial AD (FAD). In certain embodiments, the AD is sporadic AD (SAD). In particular embodiments, the RyR is Type 2 RyR (RyR-2). In particular embodiments, the RyR is Type 1 RyR (RyR-1). In particular embodiments, the RyR is Type 3 RyR (RyR-3). In particular embodiments, the RyR is a combination of RyR subtypes, e.g., RyR-1, RyR-2 and RyR-3, including all RyR subtypes. In some embodiments, the pharmaceutical composition comprising dantrolene is administered daily. In some embodiments, the pharmaceutical composition comprising dantrolene is administered three times per week. In some embodiments, the pharmaceutical composition comprising dantrolene is administered one time per week. In various embodiments, the pharmaceutical composition comprising dantrolene is administered for four months to one year. In some embodiments, the pharmaceutical composition comprising dantrolene is administered for four to six months. In certain embodiments, the pharmaceutical composition comprising dantrolene is administered for up to four months. In various embodiments, the pharmaceutical composition comprising dantrolene is administered for longer than one year. In various embodiments, the pharmaceutical composition comprising dantrolene is administered for up to two years. In various embodiments, the pharmaceutical composition comprising dantrolene is administered for longer than two years.

In some embodiments of the method for improving memory before onset of symptoms of AD, the method further comprises administering a therapeutically effective amount of a glutamate receptor antagonist to the subject. In some embodiments of the method, the method further comprises (a) obtaining cerebrospinal fluid (CSF) from the subject before intranasally administering to the subject the pharmaceutical composition comprising dantrolene; and (b) determining a level of glutamate in the CSF, wherein a determined level of glutamate in step (b) that is higher than a level of glutamate in CSF obtained from a control subject is indicative of suitability of the subject for treatment with dantrolene. In some embodiments, the method further comprises obtaining CSF from the subject before administering the therapeutically effective amount of the glutamate receptor antagonist; and determining a level of glutamate in the CSF, wherein a determined level of glutamate that is higher than a level of glutamate in CSF obtained from a control subject is indicative of suitability of the subject for treatment with a glutamate receptor antagonist. In particular embodiments, the glutamate receptor antagonist is an agent that blocks the NMDA receptor by competitive antagonism at a glutamate-binding site or is an agent that blocks the NMDA receptor by noncompetitive antagonism at a glycine, phencyclidine and/or magnesium binding site. In some embodiments, the agent that blocks the NMDA receptor by competitive antagonism at a glutamate-binding site is selfotel (CGS 19755) aptiganel (CNS 1102), CGP 37849, APV or AP-5 (R-2-amino-5-phosphonopentanoate), 2-amino-7-phosphono-heptanoic acid (AP-7), 3-[(R)-2-carboxypiperazin-4-yl]-prop-2-enyl-1-phosphonic acid (CPPene) and/or aspartame. In some embodiments, the agent that blocks the NMDA receptor by noncompetitive antagonism at a phencyclidine (PCP), magnesium, and/or MK-801 (dizocilpine) binding site is memantine, ketamine, phencyclidine, 3-MEO-PCP, 8A-PDHQ, amantadine, atomoxetine, AZD6765, agmatine, delucemine, delucemine, dextrallorphan, dextromethorphan, dextrorphan, diphenidne, ethanol, eticylidine, gacyclidine, methoxetamine (MXE), minocycline, nitromemantine, nitrous oxide, PD-137889, rolicyclidine, tenocyclidine, methoxydine, tiletamine, neramexane, eliprodil, etoxadrol, dexoxadrol, WMS-2539, NEFA, rermacemide, magnesium sulfate, aptiganel, HU-211, huperzine A, Dipeptide D-Phe-L-Tyr, Ibogaine, Apocynaceae, Remacemide, Rhynchophylline, gabapentin, or dizocilpine (MK-801). In some embodiments, the agent that blocks the NMDA receptor by noncompetitive antagonism at a glycine binding site is (GLYX-13), NRX-1074, 7-Chlorokynurenic acid, 4-Chlorokynurenine (AV-101), 5,7-Dichlorokynurenic acid, Kynurenic acid, TK-40 (competitive antagonist at the GluN1 glycine binding site), 1-aminocyclo-propanecarboxylic acid (ACPC), L-Phenylalanine, or Xenon.

In another aspect, this invention provides a method for improving memory loss after onset of symptoms of Alzheimer's Disease (AD), wherein said memory loss is caused by AD, the method comprising intranasally administering to a subject in need thereof an amount of a pharmaceutical composition comprising dantrolene effective to inhibit over-activation of NMDA receptor and/or ryanodine receptor (RyR). In some embodiments, the intranasal administration of the pharmaceutical composition comprising dantrolene does not impair olfactory function, motor function, or liver function of the subject. In particular embodiments, the symptoms of AD are neuropathology, cognitive dysfunction or a combination thereof. In various embodiments, the cognitive dysfunction is short-term or long-term memory loss, learning difficulty, thinking difficulty, attention/concentration difficulty, perception difficulty, difficulty in language use, reasoning difficulty, difficulty in making decisions/impaired judgment, problem solving difficulty, confusion, poor motor coordination, or a combination thereof. In an embodiment, the memory loss is hippocampal-dependent and hippocampal-independent memory loss. In some embodiments, the neuropathology is amyloid accumulation between brain neurons. In some embodiments, the AD is familial AD (FAD). In certain embodiments, the AD is sporadic AD (SAD). In particular embodiments, the RyR is Type 2 RyR (RyR-2). In particular embodiments, the RyR is Type 1 RyR (RyR-1). In some embodiments, the RyR is Type 3 RyR (RyR-3). In particular embodiments, the RyR is a combination of RyR subtypes, e.g., RyR-1, RyR-2 and RyR-3, including all RyR subtypes. In some embodiments of the provided methods, the pharmaceutical composition comprising dantrolene is administered daily. In some embodiments, the pharmaceutical composition comprising dantrolene is administered three times per week. In some embodiments, the pharmaceutical composition comprising dantrolene is administered one time per week. In various embodiments, the pharmaceutical composition comprising dantrolene is administered for four months to one year. In some embodiments, the pharmaceutical composition comprising dantrolene is administered for four to six months. In certain embodiments, the pharmaceutical composition comprising dantrolene is administered for up to four months. In various embodiments, the pharmaceutical composition comprising dantrolene is administered for longer than one year. In various embodiments, the pharmaceutical composition comprising dantrolene is administered for up to two years. In various embodiments, the pharmaceutical composition comprising dantrolene is administered for longer than two years.

In some embodiments of the method for improving memory after onset of symptoms of AD, the method further comprises administering a therapeutically effective amount of a glutamate receptor antagonist to the subject. In some embodiments of the method, the method further comprises (a) obtaining cerebrospinal fluid (CSF) from the subject before intranasally administering to the subject the pharmaceutical composition comprising dantrolene; and (b) determining a level of glutamate in the CSF, wherein a determined level of glutamate in step (b) that is higher than a level of glutamate in CSF obtained from a control subject is indicative of suitability of the subject for treatment with dantrolene. In some embodiments, the method further comprises obtaining CSF from the subject before administering the therapeutically effective amount of the glutamate receptor antagonist; and determining a level of glutamate in the CSF, wherein a determined level of glutamate that is higher than a level of glutamate in CSF obtained from a control subject is indicative of suitability of the subject for treatment with a glutamate receptor antagonist. In particular embodiments, the glutamate receptor antagonist is an agent that blocks the NMDA receptor by competitive antagonism at a glutamate-binding site or is an agent that blocks the NMDA receptor by noncompetitive antagonism at a glycine, phencyclidine and/or magnesium binding site. In some embodiments, the agent that blocks the NMDA receptor by competitive antagonism at a glutamate-binding site is selfotel (CGS 19755) aptiganel (CNS 1102), CGP 37849, APV or AP-5 (R-2-amino-5-phosphonopentanoate), 2-amino-7-phosphono-heptanoic acid (AP-7), 3-[(R)-2-carboxypiperazin-4-yl]-prop-2-enyl-1-phosphonic acid (CPPene) and/or aspartame. In some embodiments, the agent that blocks the NMDA receptor by noncompetitive antagonism at a phencyclidine (PCP), magnesium, and/or MK-801 (dizocilpine) binding site is memantine, ketamine, phencyclidine, 3-MEO-PCP, 8A-PD-HQ, amantadine, atomoxetine. AZD6765, agmatine, delucemine, delucemine, dextrallorphan, dextromethorphan, dextrorphan, diphenidne, ethanol, eticylidine, gacyclidine, methoxetamine (MXE), minocycline, nitromemantine, nitrous oxide, PD-137889, rolicyclidine, tenocyclidine, methoxydine, tiletamine, neramexane, eliprodil, etoxadrol, WMS-2539, NFA, remacernide, magnesium sulfate, aptiganel, HU-211, huperzine A, Dipeptide D-Phe-L-Tyr, Ibogaine, Apocynaceae, Remacemide, Rhynchophylline, gabapentin, or dizocilpine (MK-801). In some embodiments, the agent that blocks the NMDA receptor by noncompetitive antagonism at a glycine binding site is (GLYX-13), NRX-1074, 7-Chlorokynurenic acid, 4-Chlorokynurenine (AV-101), 5,7-Dichlorokynurenic acid, Kynurenic acid, TK-40 (competitive antagonist at the GluN1 glycine binding site), 1-aminocyclo-propanecarboxylic acid (ACPC), L-Phenylalanine, or Xenon.

In another aspect, this invention provides a method for increasing concentration and duration of dantrolene in the brain of a subject, the method comprising intranasally administering to a subject in need thereof an amount of a pharmaceutical composition comprising dantrolene.

In a further aspect, this invention provides a method for inhibiting impaired neurogenesis and/or synaptogenesis in neurons in a subject with or suspected of having Alzheimer's Disease (AD), wherein said impairment of neurogenesis and/or synaptogenesis is caused, at least in part, by over activation of endoplasmic reticulum (ER) ryanodine receptor (RyR), the method comprising: (a) intranasally administering to said subject an amount of a pharmaceutical composition comprising dantrolene effective to decrease release of ER calcium ions ($Ca^{2+}$); and (b) administering a therapeutically effective amount of a glutamate receptor antagonist to the subject of step (a). In some embodiments, the intranasal administration of the pharmaceutical composition comprising dantrolene does not impair olfactory function, motor function, or liver function of the subject. In some embodiments, the method further comprises: c) obtaining cerebrospinal fluid (CSF) from the subject before step (a); and d) determining a level of glutamate in the CSF, wherein a determined level of glutamate in step (d) that is higher than a level of glutamate in CSF obtained from a control subject is indicative of suitability of the subject for treatment with dantrolene. In various embodiments, the method further comprises obtaining CSF from the subject before step (b); and determining a level of glutamate in the CSF, wherein a determined level of glutamate that is higher than a level of glutamate in CSF obtained from a control subject is indicative of suitability of the subject for treatment with a glutamate receptor antagonist. In some embodiments, the glutamate receptor antagonist is an agent that blocks the NMDA receptor by competitive antagonism at a glutamate-binding site or is an agent that blocks the NMDA receptor by noncompetitive antagonism at a glycine, phencyclidine and/or magnesium binding site. In various embodiments, the agent that blocks the NMDA receptor by competitive antagonism at a glutamate-binding site is selfotel (CGS 19755) aptiganel (CNS 1102), CGP 37849, APV or AP-5 (R-2-amino-5-phosphonopentanoate), 2-amino-7-phosphono-heptanoic acid (AP-7), 3-[(R)-2-carboxypiperazin-4-yl]-prop-2-enyl-1-phosphonic acid (CPPene) and/or aspartame. In some embodiments, the agent that blocks the NMDA receptor by noncompetitive antagonism at a phencyclidine (PCP), magnesium, and/or MK-801 (dizocilpine) binding site is memantine, ketamine, phencyclidine, 3-MEO-PCP. 8A-PDHQ, amantadine, atomoxetine, AZD6765, agnatine, delucenine, delucemine, dextrallorphan, dextromethorphan, dextrorphan, diphenidne, ethanol, eticylidine, gacyclidine, methoxetamine (MXE), minocycline, nitromemantine, nitrous oxide, PD-137889, rolicyclidine, tenocyclidine, methoxydine, tiletamine, neramexane, eliprodil, etoxadrol, dexoxadrol, WMS-2539, NEFA, remacemide, magnesium sulfate, aptiganel, HU-211, huperzine A, Dipeptide D-Phe-L-Tyr, Ibogaine, Apocynaceae, Remacemide, Rhynchophylline, gabapentin, or dizocilpine (MK-801). In various embodiments, the agent that blocks the NMDA receptor by noncompetitive antagonism at a glycine binding site is (GLYX-13), NRX-1074, 7-Chlorokynurenic acid, 4-Chlorokynurenine (AV-101), 5,7-Dichlorokynurenic acid, Kynurenic acid, TK-40 (competitive antagonist at the GluN1 glycine binding site), 1-aminocyclo-propanecarboxylic acid (ACPC), L-Phenylalanine, or Xenon. In some embodiments of the methods for inhibiting impaired neurogenesis and/or synaptogenesis in neurons in a subject with or suspected of having AD, the neurogenesis comprises neurogenesis from neuroprogenitor cells (NPCs) into immature neurons, followed by neurogenesis from immature neurons into cortical neurons. In various embodiments, the synaptogenesis occurs in cortical neurons. In some embodiments, the cortical neurons are cholinergic neurons. In certain embodiments, the cortical neurons are basal forebrain cholinergic neurons (BFCN) neurons, prefrontal cortex neurons, hippocampus neurons, or a combination thereof. In particular embodiments, the AD is familial Alzheimer's disease (FAD) or sporadic Alzheimer's disease (SAD). In some embodiments, the RyR is Type 2 RyR (RyR-2). In particular embodiments, the RyR is Type 1 RyR (RyR-1). In some embodiments, the RyR is Type 3 RyR (RyR-3). In particular embodiments, the RyR is a combination of RyR subtypes, e.g., RyR-1, RyR-2 and RyR-3, including all RyR subtypes. In certain embodiments, the over activation of endoplasmic reticulum (ER) ryanodine receptor (RyR) elevates mitochondrial calcium, resulting in decrease of ATP. In some embodiments, the intranasal administration of dantrolene reduces the elevated mitochondrial calcium and increases cytosolic ATP. In some embodiments of the provided methods, the pharmaceutical composition comprising dantrolene is administered daily. In some embodiments, the pharmaceutical composition comprising dantrolene is administered three times per week. In some embodiments, the pharmaceutical composition comprising dantrolene is administered one time per week. In various embodiments, the pharmaceutical composition comprising dantrolene is administered for four months to one year. In some embodiments, the pharmaceutical composition comprising dantrolene is administered for four to six months. In certain embodiments, the pharmaceutical composition comprising dantrolene is administered for up to four months. In various embodiments, the pharmaceutical composition comprising dantrolene is administered for longer than one year. In various embodiments, the pharmaceutical composition comprising dantrolene is administered for up to two years. In various embodiments, the pharmaceutical composition comprising dantrolene is administered for longer than two years.

All scientific publications cited herein are hereby incorporated by reference in their entireties.

The following examples are presented in order to illustrate certain embodiments of the invention more fully. The examples should in no way be construed, however, as limiting the broad scope of the invention.

EXAMPLES

Example 1

Dantrolene Inhibits Impaired Neurogenesis and Synaptogenesis in Induced Pluripotent Stem Cells from Alzheimer's Disease Patients While not wishing to be bound to any particular theory, it is believed that dantrolene inhibits impaired neurogenesis and synaptogenesis by correction of calcium dysregulation due to over-activation of ryanodine receptors and associated impairment of lysosome and autophagy function. In this study and with the use of iPSC from both SAD and FAD patients and their derived neuroprogenitor cell (NPC) and basal forebrain cholinergic neurons (BFCN), the effects and mechanisms of dantrolene on neurogenesis and synaptogenesis were studied. Dantrolene significantly ameliorated the impairment of neurogenesis and synaptogenesis, which was associated with its correction of RyR over-activation, intracellular $Ca^{2+}$ dysregulation and disruption of autophagy.

Materials & Methods

Cell Culture

Human control (AG02261) and sporadic Alzheimer's disease (AG11414) iPSCs were obtained from John A. Kessler's lab. Familial Alzheimer's disease (GM24675) iPSCs were purchased from Coriell Institute. Each type of iPSC was generated from skin fibroblasts of one heathy human subject or one patient diagnosed of either SAD or FAD. The human pluripotent stem cells were maintained on Matrigel coated plates (BD Biosciences) in mTeSR™1 medium (Catalog #05850, Stem cell Technologies) and were cultured in a 5% $CO_2$ humidified atmosphere at 37° C. The culture medium was changed every day.

Cell Viability

The cell viability on different wells in 96-well plates was determined using the MTT (3-(4,5-dimethylthiazol-2-yl)-2,5-diphenyltetrazolium bromide, Sigma-Aldrich, St. Louis, MO) reduction assay at 24 h as previously described by Qiao H, et al., Anesthesiology 2017; 127:490; Ren G, et al., Sci Rep 2017; 7:12378, each of which is incorporated by reference in its entirety. After being washed with PBS, the samples were incubated with fresh culture medium containing MTT (0.5 mg/mL in the medium) at 37° C. for 4 h in the dark. The medium was then removed and formazan was solubilized with dimethyl sulfoxide (DMSO). The absorbance was measured at 540 nm with plate reader (Synergy™ H1 microplate reader, BioTek, Winooski, VT).

Cell Proliferation Assays

The iPSCs were plated onto cover glasses coated with Matrigel in mTeSR™1 medium. 5-Bromodeoxyuridine (BrdU, Invitrogen, Eugene, OR) was added to the mTeSR™1 medium 4 h before the end of treatment with a final concentration of 30 μM. The cells were then fixed in 4% paraformaldehyde and permeabilized with 0.1% Triton X-100. For BrdU detection, acid treatment (1N HCL 10 min on ice followed by 2N HCL 10 min at room temperature) separated DNA into single strands so that the primary antibody could access the incorporated BrdU. After being incubated with blocking solution (5% normal goat serum in PBS containing 0.1% Triton X-100), cells were incubated with rat monoclonal anti-BrdU primary antibody (1:100; Santa Cruz Biotechnology, Dallas, TX) overnight at 4° C. After subsequent wash with PBS containing 0.1% Triton X-100, cells were incubated with fluorescently labeled secondary antibody conjugated with anti-rat IgG (1:1,000; Invitrogen, Eugene, OR) for 2 h at room temperature. Cell nuclei were counterstained with 4', 6-diamidino-2-phenylindole (DAPI, Invitrogen, Eugene, OR) for 5 min at room temperature. The immunostained cells were covered and then mounted on an Olympus BX41TF fluorescence microscope (200×; Olympus USA, Center Valley, PA). Images were acquired using iVision 10.10.5 software (Biovision Technologies, Exton, PA). Five sets of images were acquired at random locations on the cover glass and were subsequently merged using ImageJ 1.49v software (National Institutes of Health, Bethesda, MD). The percentage of 5-BrdU-positive cells over the total number of cells was calculated and compared across different groups from at least three different cultures.

Differentiation of iPSCs

The protocol for differentiation into cortical neurons and BFCNs from iPSCs was adapted from previously described protocols, as described by Shi Y, et al., Nat Protoc 2012; 7:1836; Bissonnette C J, et al., Stem Cells 2011; 29:802, each of which is incorporated by reference in its entirety. Briefly, feeder-free cultured iPSC cells were induced to form neural progenitors via Dual-SMAD inhibition. The cells were cultured in chemical defined condition with SB431542 2 uM and DMH1 2 uM (both from Tocris, Minneapolis, MN) for 7 days.

For cortical neurons, the medium was changed on Day 12 to neural maintenance medium (i.e., is a 1:1 mixture of N-2 and B-27-containing media, where the N-2 medium consists of DMEM/F-12 GlutaMAX, 1×N-2, 5 g/mL insulin, 1 mM L-glutamine, 100 m nonessential amino acids, 100 μM 2-mercaptoethanol, 50 U/mL penicillin and 50 mg/mL streptomycin and the B-27 medium consists of Neurobasal, 1×B-27, 200 mM L-glutamine, 50 U/mL penicillins and 50 mg/mL streptomycin.) and continued from Day 12. Cells were checked daily. Neural rosette structures were obvious when cultures were viewed with an inverted microscope around day 24-29. From this point, the medium was changed every other day.

For BFCN differentiation, the iPSC-derived primitive neural stem cells were developed under SHH (500 ng/mL; 1845-SH; R&D System, MN, USA) and then treated with NGF (50-100 ng/mL; R&D) from day 24. At day 28 the neural progenitors adhered to laminin substrate that were previously plated on the laminin at a density of 5,000 cells/cm$^2$. The plated cells were preferably grown in a neuronal differentiation medium consisting of neurobasal medium, N2 supplement (Invitrogen) in the presence of NGF (50-100 ng/mL; R&D), cAMP (1 μM; Sigma), BDNF, GDNF (10 ng/mL; R&D), SHH (50 ng/mL; R&D), as described by Liu Y, et al., Nat Biotechnol 2013; 31:440, which is incorporated by reference in its entirety.

$Ca^{2+}$ Measurements

The changes of cytosolic $Ca^{2+}$ concentration ($[Ca^{2+}]_c$) of iPSCs after ATP exposure were measured using jellyfish photoprotein aequorin-based probe. 7.5-1.2×10$^4$ cells were plated on 12 mm coverslips in 24 well plate, grow to 50-60% confluence then transfected with the cyt-Aeq plasmid using Lipofectamine 3000 Transfection Reagent (Thermo Fisher Scientific) according to the manufacturer's instruction. The next day, the transfected cells were incubated with 5 μM coelenterazine for 1 h in modified Krebs-Ringer buffer (in mM: 140 NaCl, 2.8 KCl, 2 $MgCl_2$, 10 Hepes, 11 glucoses, pH 7.4) supplemented with 1 mM $CaCl_2$ and then were transferred to the perfusion chamber. All aequorin measurements were carried out in KRB, anesthetics were added to the same medium as specified. The experiments were performed in a custom-built aequorin recording system. For extracellular $Ca^{2+}$ free experiments, $Ca^{2+}$ free buffer was used (KRB without $Ca^{2+}$ with 5 mM EGTA). The experiments were terminated by lysing the cells with 100 μM digitonin in a hypotonic $Ca^{2+}$-rich solution (10 mM $CaCl_2$ in $H_2O$), thus discharging the remaining aequorin pool. The light signal was collected and calibrated into $[Ca^{2+}]_c$ values by an algorithm based on the $Ca^{2+}$ response curve of aequorin at physiological conditions of pH, [$Mg^{2+}$], and ionic strength, as previously described by Filadi R, et al., PNAS 2015; 201504880; Bonora M, et al., Nat Protoc 2013; 8:2105, each of which is incorporated by reference in its entirety.

The changes of cytosolic $Ca^{2+}$ concentration ($[Ca^{2+}]_c$) of iPSCs after exposure to NMDA was measured by Fura-2/AM fluorescence (Molecular probe, Eugene, OR) using methods described before. Assays were carried out on an Olympus IX70 inverted microscope (Olympus America Inc, Center Valley, PA) and IPLab v3.71 software (Scanalytics, Milwaukee WI). In brief, the iPSCs were plated onto a 35 mm culture dish.

After the cells were washed three times in $Ca^{2+}$-free Dulbecco's modified eagle medium (DMEM, Gibco, Grand Island, NY) and loaded with 2.5 m Fura-2/AM in the same buffer for 30 min at 37° C., the cells were then washed twice and incubated with $Ca^{2+}$-free DMEM for another 30 min at 37° C. Fura-2AM was measured by recording alternate at 340 and 380 nm excitation, and emission at 510 nm was detected for up to 10 min for each treatment. The evoked changes were recorded in response to treatment of 500 μM NMDA with or without dantrolene 30 M (Dan). The results were presented as a ratio of F340/F380 nm and averaged from at least three separate experiments.

Western Blotting

Western blotting was performed according to the standard procedure. Total protein extracts from iPSCs cells were obtained by lysing the cells in ice-cold lysis buffer (50 mM Tris-HCl, 150 mM NaCl and 1% Triton X-100) in the presence of a cocktail of protease inhibitors, as described by Hollomon, M G, et al., BMC Cancer 2013; 13:500, which is incorporated by reference in its entirety. After centrifugation, the supernatant was collected, and the total protein was quantified using a bicinchoninic acid (BCA) protein assay kit (Thermo Scientific, Rockford, IL). Equal amounts of protein for each lane were loaded and separated on 15% sodium dodecyl sulfate-polyacrylamide gel electrophoresis (SDSPAGE).

After electrophoresis, proteins were transferred onto a polyvinylidene fluoride (PVDF) membrane. The membranes were blocked with 5% fat-free milk dissolved in PBS-T for 1 h at room temperature, and then stained with primary antibody at 4° C. overnight. After the wash with PBS-T, the membranes were incubated with secondary antibodies (HRP conjugated anti-rabbit and anti-mouse IgG) at 1:1,000 dilutions, and β-actin served as a loading control. Signals were detected with an enhanced chemiluminescence detection system (Millipore, Billerica, MA) and quantified by scanning densitometry.

Immunocytochemistry

The cells were fixed in 4% paraformaldehyde for 15 minutes followed by three 1×PBS washes. They were then blocked by 5% normal goat serum in PBS containing 0.1% Triton X-100 at room temperature for 1 hour. Primary antibodies were applied for overnight at 4° C. in 1×PBS containing 1% BSA and 0.3% Triton-X-100. Following three washes with PBS, alexa fluor conjugated secondary antibodies (1:1000, Invitrogen) together with DAPI (1:2000) were added for 1 hour. After three more washes, coverslips were mounted with Prolong Gold antifade reagent (Invitrogen) and imaged.

Primary antibodies used were: Oct4 (1:500, Cell Signaling Technology), Sox2 (1:500, Millipore), PAX6 (1:500, BioLegend), Tbr 1 (1:500, Abcam), ChAT (1:100, Millipore), Map2 (1:500, Sigma), PSD95 (1:500, BioLegend), Synapsin-1(1:500, BioLegend), EEA1 (1:100, Cell Signaling Technology), LAMP-2 (1:100, Santa Cruz), Calnexin (1:100, Cell Signaling Technology) and LC3 (1:200, Cell Signaling Technology).

Lysosome Acidity Measurements

As described previously by Ren G, et al., Sci Rep 2017; 7:12378, which is incorporated by reference in its entirety, LysoTracker® Red DND-99 (Molecular Probe, Eugene, OR) probe stock solution was diluted to a working concentration of 50 nM in HBSS+. IPSCs cells were plated on coverslips coated with Matrigel (BD Biosciences) in mTeSR™1 (Catalog #05850). After being washed three times with HBSS+, the cells were loaded with pre-warmed (37° C.) probe containing HBSS+ and incubated for 1 h at 37° C. Fresh medium was added to replace the labeling solution. The cells were observed by a fluorescent microscope fitted with the correct filter set for the probe used, to determine if the cells were sufficiently fluorescent. LysoTracker Red used an emission maximum of ~590 nm and an excitation maximum of ~577 nm.

Data Analysis and Statistics

All data were tested for normal distribution by Kolmogorov-Smirnov (KS) normality test and Brown-Forsythe test to determine if parametric or nonparametric tests are used for statistical analysis. Parametric variables were expressed as Means±SD and analyzed using Student's unpaired two-tailed t test, one-way or two-way ANOVA followed by Sidak's post hoc analysis. Non-parametic variables were analyzed using Kruskal-Wallis test followed by Dunn's multiple comparison test. GraphPad Prism software (GraphPad Software, Inc., USA) was used for statistical analyses and graphs creation. P values less than 0.05 were considered statistically significant.

Results

Dantrolene Promoted Cell Viability and Inhibited Impairment of Cell Proliferation in iPSCs from AD Patients iPSC, NPCs and neurons from healthy human subjects or SAD/FAD patients were cultured and characterized by specific antibodies targeting particular types of cells. There was no significant difference in cell viability determined by MTT reduction assay of iPSC among healthy human subjects or SAD/FAD patients. However, dantrolene significantly increased MTT in iPSC SAD by 15.1% (N=8, P<0.01) and FAD by 67.6% (N=7 P<0.0001, FIG. 1A). Compared to healthy human subjects, iPSC from SAD/FAD patients tended to have impaired proliferation ability as determined by 5-BrdU incorporation, more significantly in FAD iPSC, which was inhibited by dantrolene (FIG. 1B). Compared to control, dantrolene had no significant effects on iPSC differentiation into NPCs.

Figures 2A, 2B:
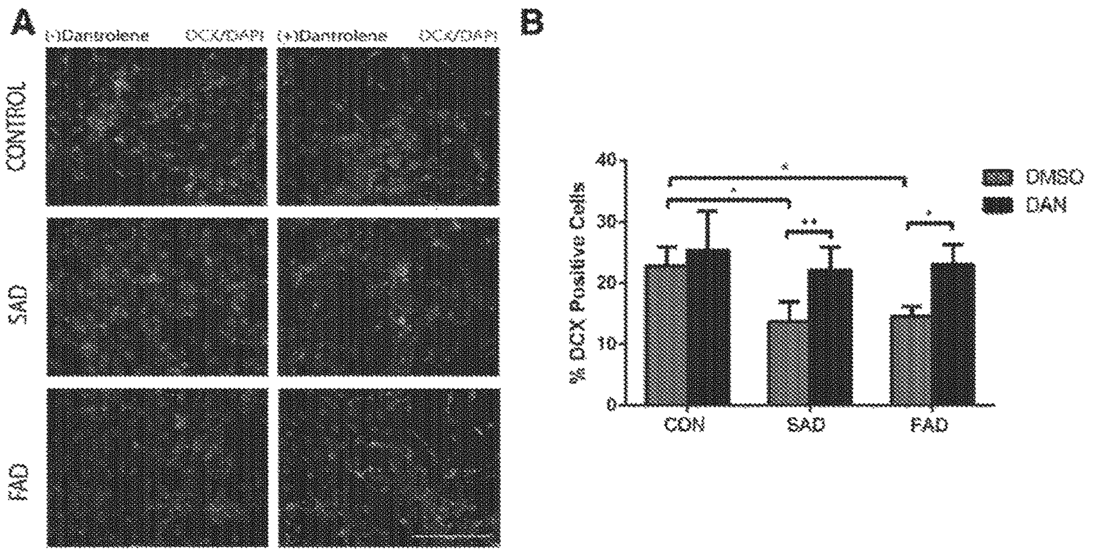
FIGS. 2A-2B show dantrolene ameliorated impairment of neuroprogenitor cells differentiation into immature neurons in cells derived from Alzheimer's disease (AD) patients. Differentiation of neural progenitor cells (NPCs) into immature neurons (differentiation day 23) was significantly impaired in both sporadic Alzheimer's disease (SAD) and familial Alzheimer's disease (FAD), which was inhibited by dantrolene (DAN).
Figures 3A, 3B, 3C, 3D, 3E, 3F:
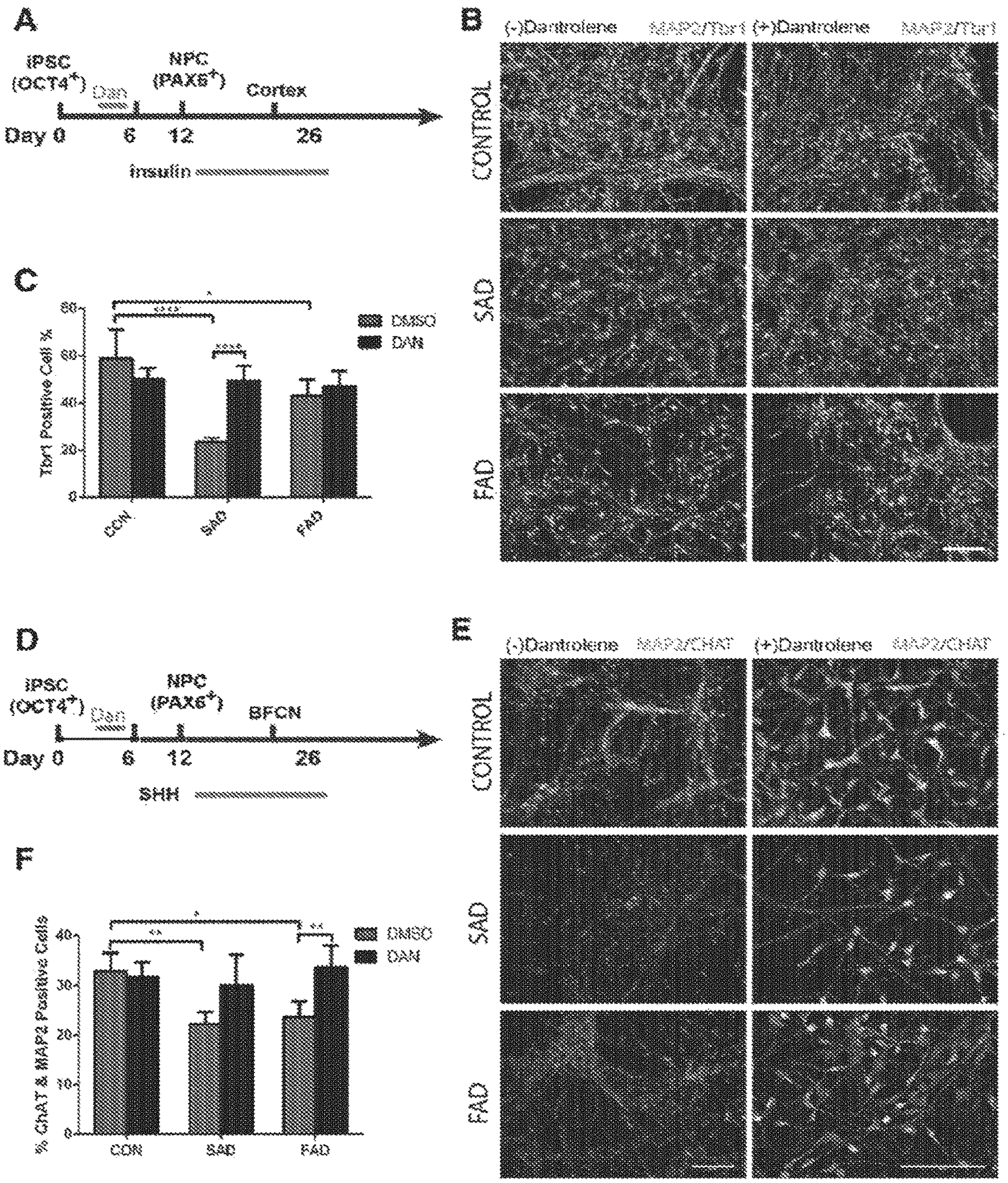
FIGS. 3A-3F show that dantrolene inhibited differentiation of neural progenitor cells (NPC) into cortical neurons and basal forebrain cholinergic neurons (BFCN) in Alzheimer's disease patient cells.

Dantrolene Ameliorated the Impairment of NPC Differentiation into Immature Neurons, Cortical Neurons and BFCN in Both SAD/FAD Cells Based on a pilot study to exert adequate dantrolene neuroprotection on neurogenesis, iPSC was treated with dantrolene (30 μM) for 3 continuous days, beginning at the induction of iPSC differentiation into NPCs (FIGS. 2A-2B and 3A-3F). Differentiation of NPC derived from SAD/FAD iPSC into immature neurons at differentiation day 23 decreased by 9.1% (N=6, P<0.05) and 8.18% (N=6, P<0.05) respectively compared to control, which was abolished by dantrolene (FIGS. 2A-2B). Compared to the control, mature cortical neurons (FIG. 3B, Trb1 positive cells, Red) in SAD and FAD patients decreased by 35.2% (N=5, P<0.0001) and 15.7% (N=5, P<0.05) respectively compared to control, an effect which was abolished by dantrolene (FIG. 3C). Using sonic hedgehog (SHH, FIG. 3D), the generation of BFCN (ChAT positive neurons, green) from iPSC was further examined. Compared to the control, differentiation into particular BFCN (FIG. 3E) decreased by 10.7% (N=5, P<0.01) and 9.2% (N=5, P<0.05) in SAD/FAD iPSC respectively, (FIG. 3F), and was also abolished by dantrolene.

Figures 4A, 4B, 4C, 4D, 4E:
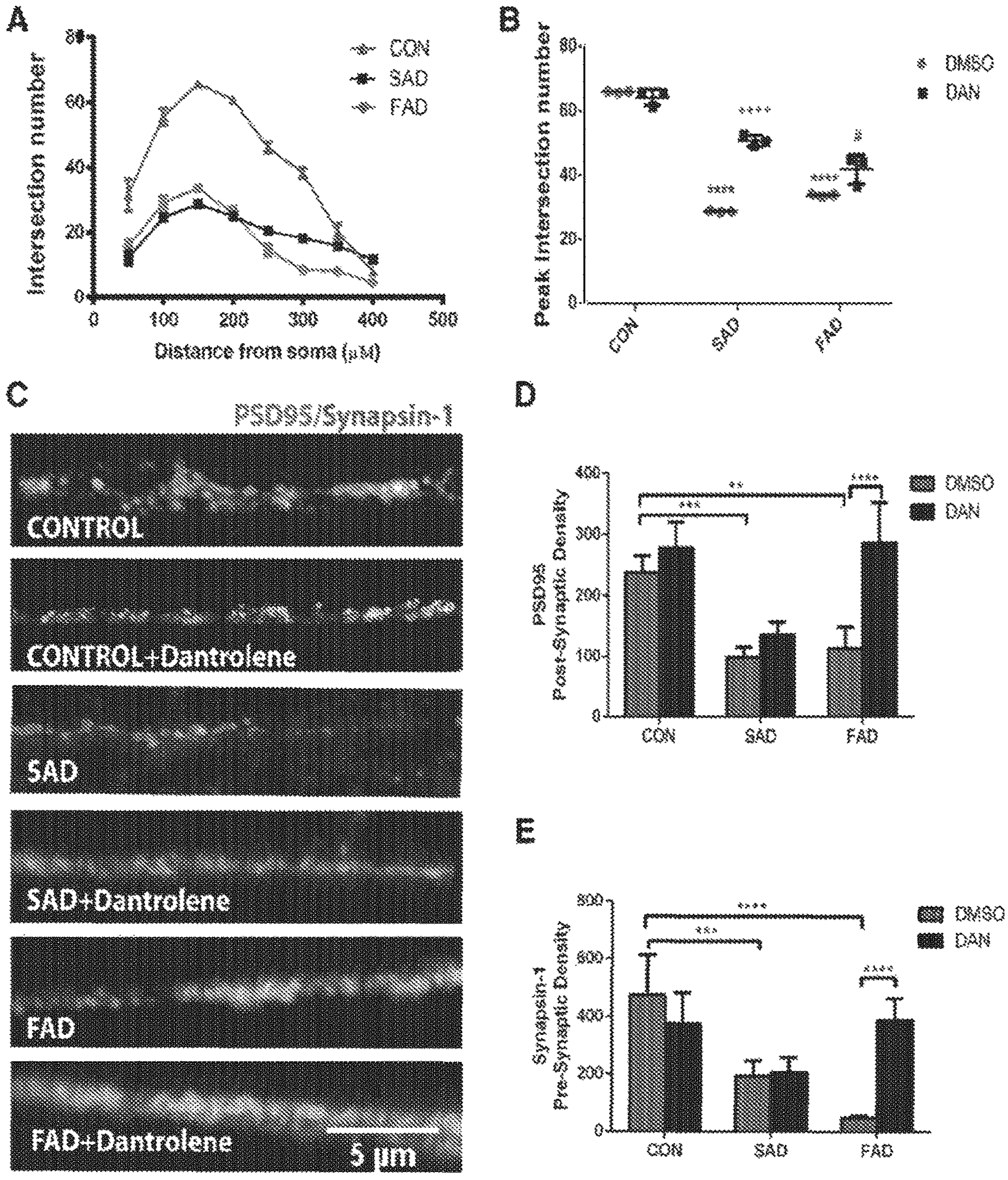
FIGS. 4A-4E show dantrolene inhibited impairment of dendrite intersection and synaptic density of neurons in Alzheimer's disease cells. NPCs were differentiated into mature cortical neurons with insulin and dantrolene (DAN) treatment was for 3 days starting from the induction of iPSC differentiation. The mean number of intersections between dendrites and concentric circles around the cortical neurons are shown as a function of the circle distance (m) from the soma.

Dantrolene Rescued the Synaptogenesis Impairment of Neurons Generated from the iPSC of SAD/FAD Patients To determine the effects of dantrolene applied during the first three days of iPSC induction period on synaptogenesis of iPSC originated neurons, the numbers of intersections between dendrites and concentric circles of the cortical neurons, shown as the distance (m) of the circles from the soma were quantified (FIG. 4A). Compared to the control neurons, the number of intersections (equivalent to synaptogenesis) were significantly decreased in cortical neurons generated from both SAD and FAD patient iPSCs, and most dramatically by 76.3% (N=3, P<0.0001) and 23.7% respectively (N=3, P<0.05) at the distance around 150 μM from soma (FIG. 4A), which was inhibited by dantrolene, especially in SAD cells (FIG. 4B). The effects of dantrolene on synaptic density were examined by determining presynaptic marker synapsin-1 (green) and postsynaptic marker PSD95 (red), using a double immunostaining technique (FIG. 4C). Synapse density determined by either PSD95 (FIG. 4D) or synapsin-1 (FIG. 4E) was significantly decreased in cortical neurons generated from either SAD by 58.2% (N=4-5, P<0.001) or FAD by 52.3% in PSD95 (N=5, P<0.01) and SAD by 59.1% (N=4-5, P<0.01) or FAD by 89.8% in synapsin-1 (N=5, P<0.0001) and both were inhibited by dantrolene in FAD iPSC.

Type 2 RyR (RyR-2) was Abnormally Increased in iPSCs from AD Patients.

Figures 5A, 5B, 5C, 5D:
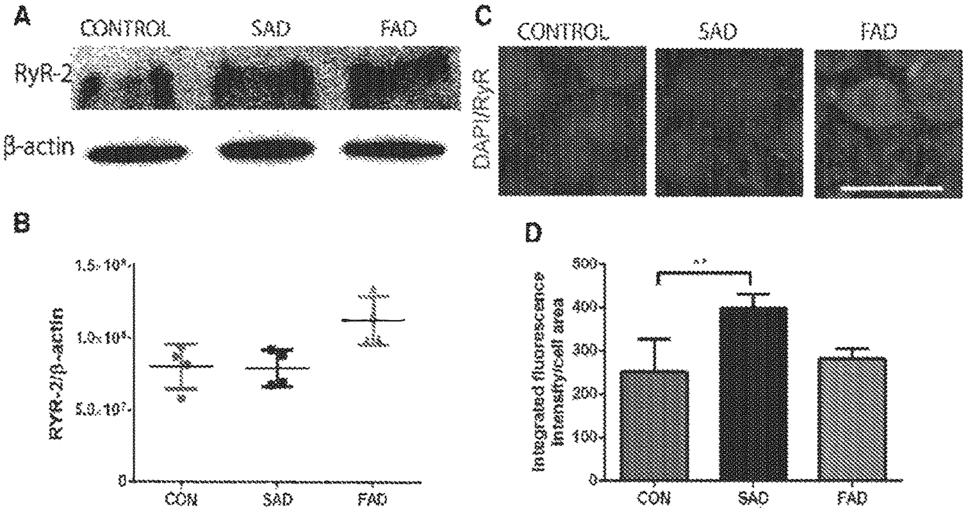
FIGS. 5A-5D show increased type 2 ryanodine receptors (RyR-2) in iPSC derived from SAD or FAD patients.

For mechanisms studies, the expression of RyR-2 was first determined using both immunoblotting (FIGS. 5A, 5B) and immunostaining (FIGS. 5C, 5D). Compared to that of healthy human subjects, RyR-2 levels in SAD/FAD patient iPSC increased by 39.5% (N=4, P=0.0558) in FAD (FIG. 5B) and mean rank different by 11.1 (N=7, P<0.01) in SAD (FIG. 5D).

Dantrolene Significantly Inhibited NMDA or ATP Mediated Abnormal Elevation of Cytosolic $Ca^{2+}$ Concentrations ($[Ca^{2+}]_c$) in iPSC from Both SAD and FAD Patients.

Figures 6A, 6B, 6C, 6D:
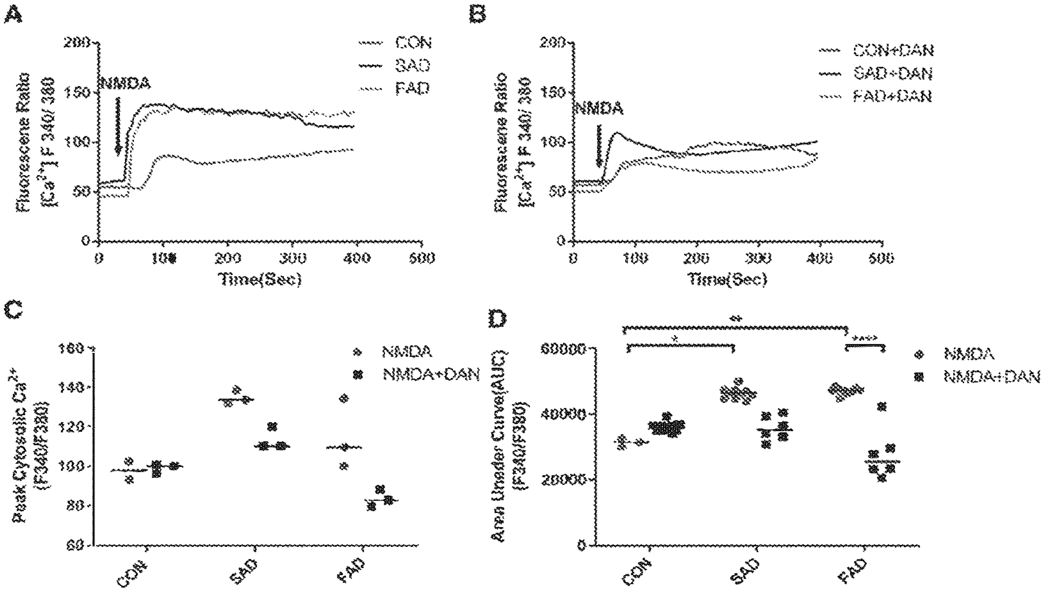
FIGS. 6A-6D show dantrolene significantly inhibited N-methyl-d-aspartate (NMDA) mediated elevation of cytosolic $Ca^{2+}$ concentrations ([$Ca^{2+}$ ]c) in induced pluripotent stem cells (iPSC) from Alzheimer's disease (AD) patients. NMDA (500 μM) induced greater overall exposure of the integrated cytosolic $Ca^{2+}$ represented by the area under curve (AUC.
Figures 7A, 7B, 7C, 7D:
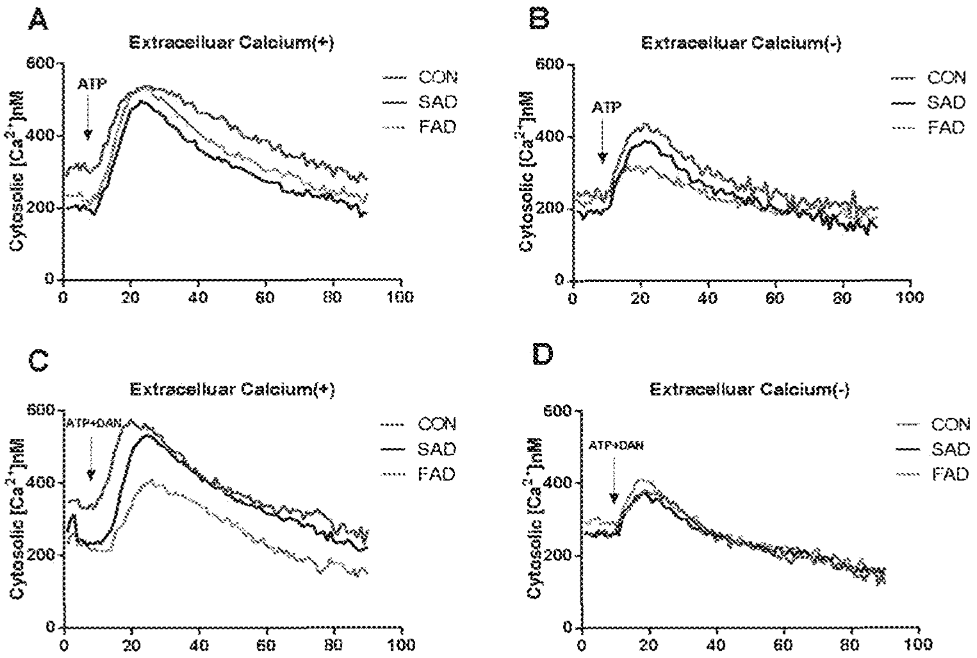
FIGS. 7A-7G show the effect of dantrolene on the adenosine triphosphate (ATP)-mediated elevation of cytosolic calcium ($Ca^{2+}$) concentrations ([$Ca^{2+}$]C) in basal forebrain cholinergic neurons from Alzheimer's disease patients. Changes of cytosolic $Ca^{2+}$ concentrations (FIGS. 7A-7D) and corresponding statistical analysis (FIGS. 7E-7G) are provided. A two-way analysis of variance was conducted comparing treatment (ATP, ATP+$Ca^{2+}$) and cell type: control (CON), sporadic Alzheimer's disease (SAD), familial Alzheimer's disease (FAD). ATP (30 μM), in the presence of 1 mM extracellular calcium (ATP+$Ca^{2+}$.
Figure 7E:
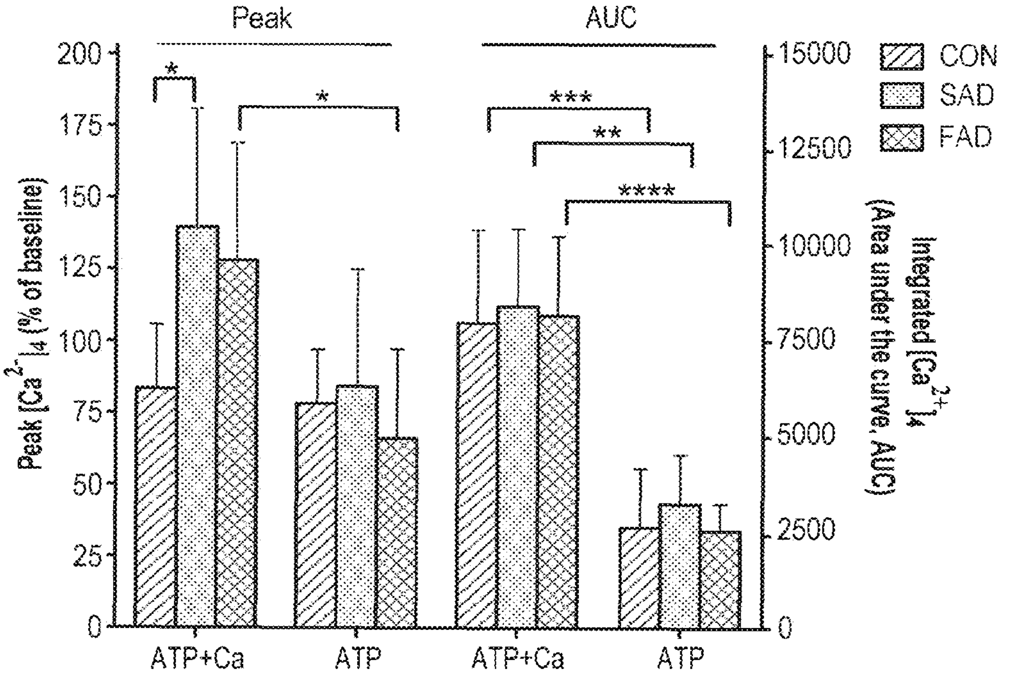
Figure 7F:
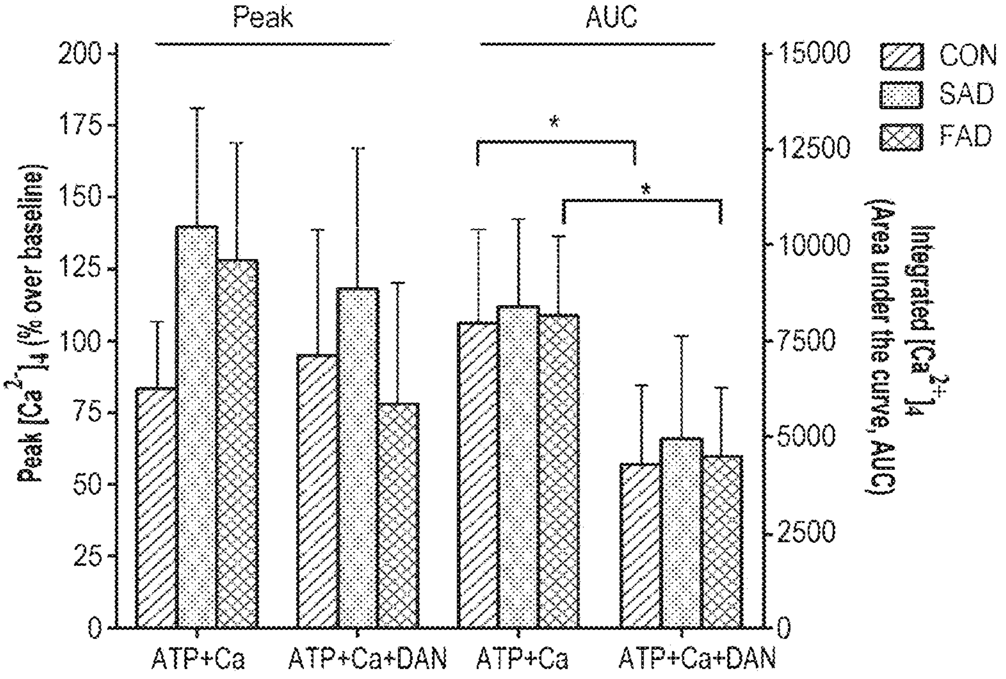
Figure 7G:
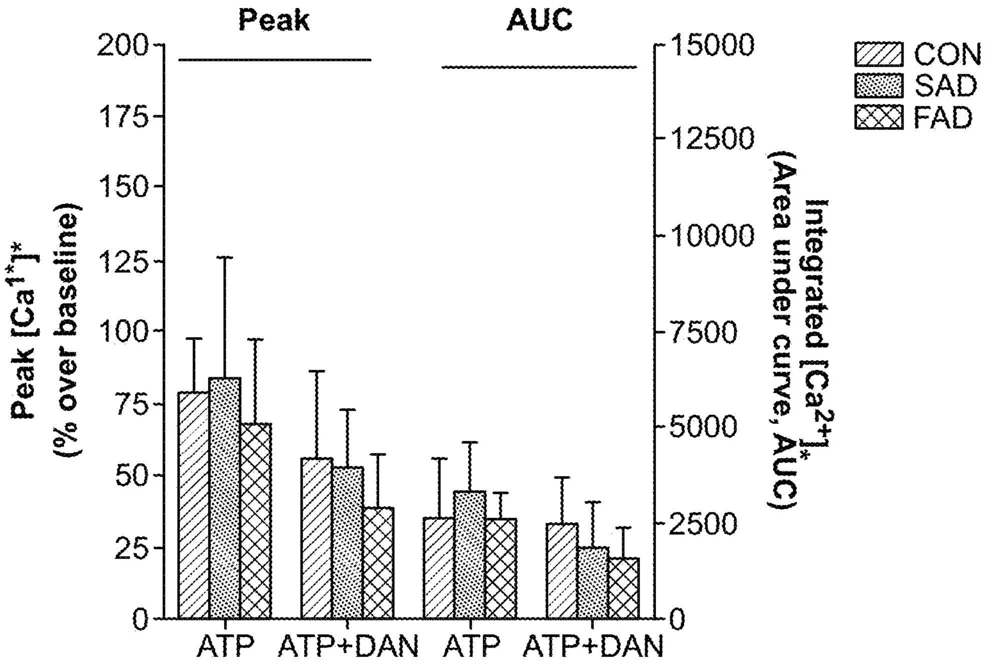

Further investigated was the possible mechanisms by which neurogenesis and synaptogenesis were impaired in SAD/FAD iPSC and were ameliorated by dantrolene. Consistent with this elevated RyR-2 in AD iPSC, the NMDA mediated elevation of peak $[Ca^{2+}]_c$ (FIGS. 6A, 6C) and integrated exposure (FIGS. 6A, 6D) were significantly higher in FAD and SAD iPSC than in the normal control, which could be inhibited by dantrolene (FIGS. 6B-6D). When three types of cells are examined for the $Ca^{2+}$ release from intracellular $Ca^{2+}$ store by treating them with ATP (30 μM), SAD/FAD iPSC showed significantly higher peak elevation of $[Ca^{2+}]_c$, (140.4%, P<0.05 or 128.3% P=0.2055 respectively vs control 84.1%, N=5-9.) which was abolished by removal of extracellular $Ca^{2+}$ and associated $Ca^{2+}$ influx form extracellular space (FIGS. 7A, 7B, 7E) and pretreatment by dantrolene (30 μM) for 1 hour (FIGS. 7C, 7F). Without $Ca^{2+}$ influx from extracellular space, ATP caused significantly lower overall elevation of $[Ca^{2+}]_c$ in all three cell types (FIG. 7E). In the absence of extracellular $Ca^{2+}$ influx, dantrolene only trended to inhibit ATP-mediated peak or overall elevation of $[Ca^{2+}]_c$ but not statistically significant in SAD/FAD cells (FIG. 7D or 7G).

Dantrolene Inhibited the Decrease of Lysosomal vATPase and Acidity in iPSC from AD Patients.

Figure 8A:
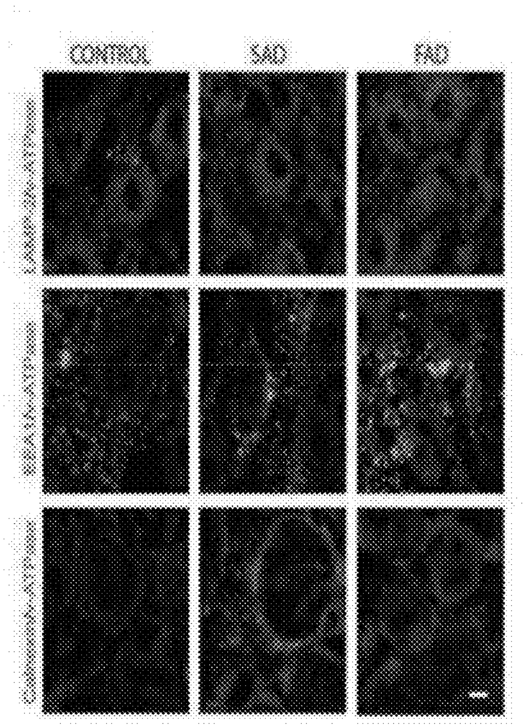
FIGS. 8A-8E show lysosomal ATPase and acidity in neurons derived from Alzheimer's disease patients were less than in control cells.
Figure 8B:
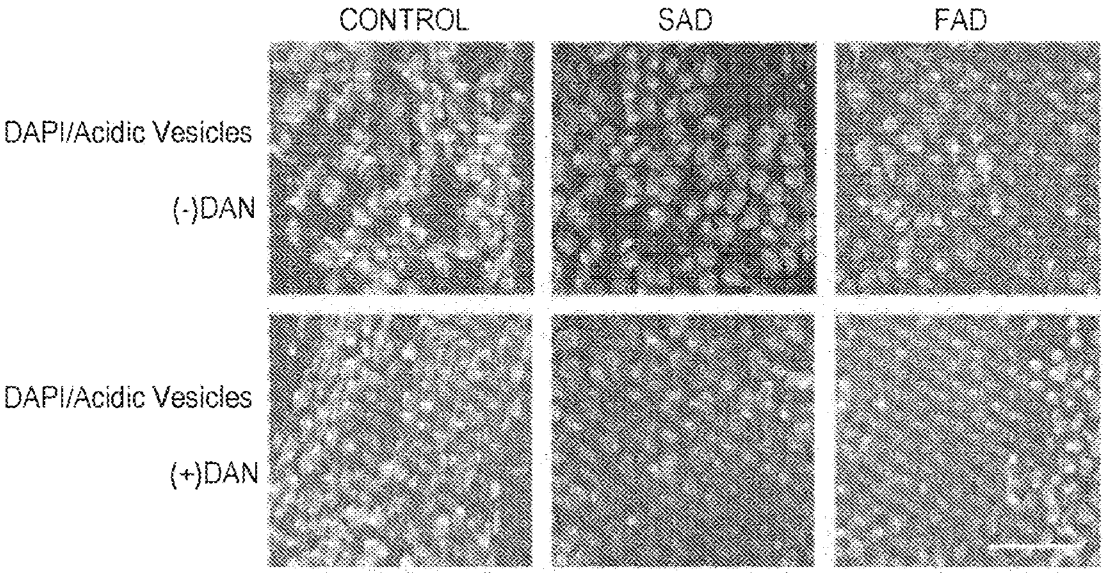
Figure 8C:
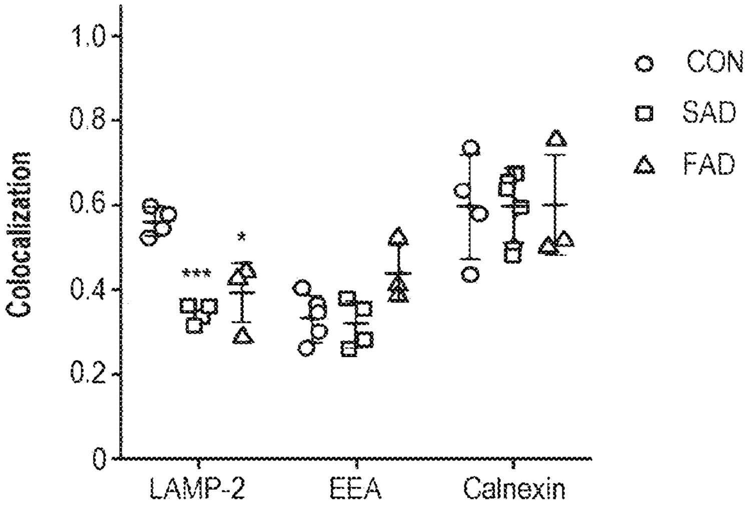
Figure 8D:
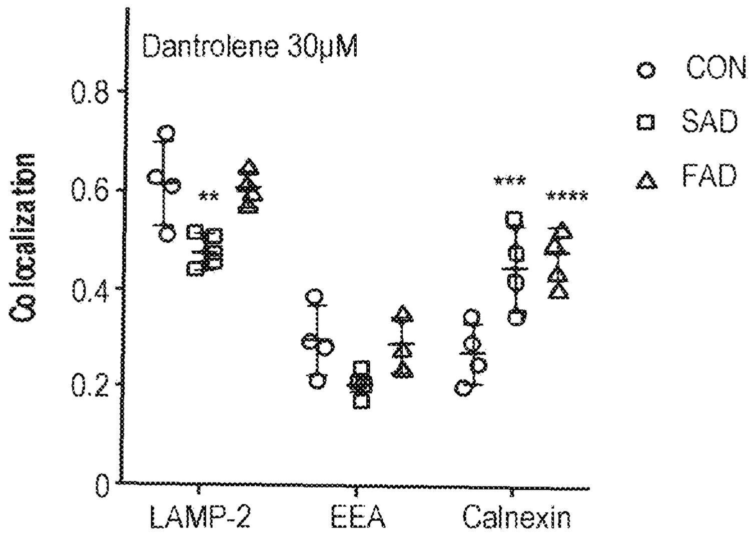
Figure 8E:
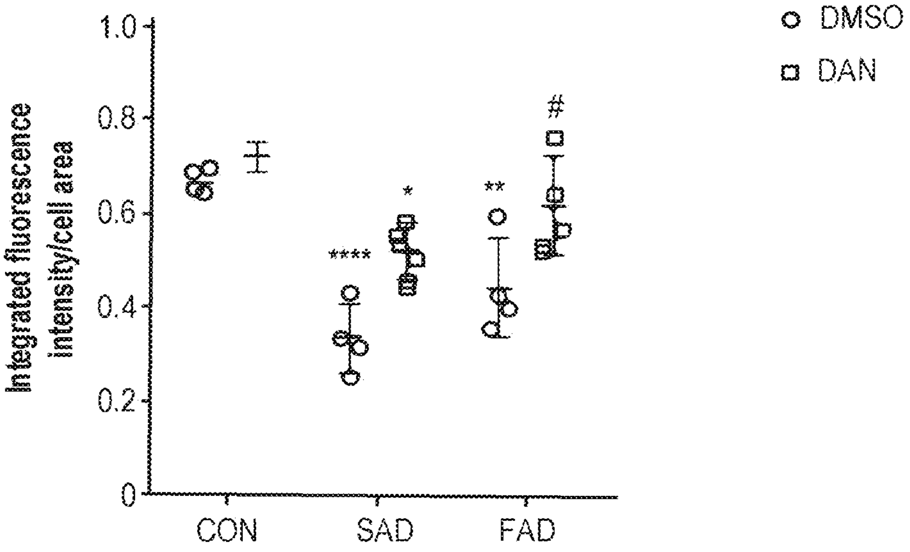

Decreased ER calcium concentrations in AD presenilin 1 mutation due to over activation of RyR impaired synthesis and secretion of vATPase from the ER into the lysosome, and subsequently decreased lysosome acidity and function, as described by Lee J H, et al., Cell 2010; 141:1146, which is incorporated by reference in its entirety. The inventors have determined the changes of lysosome vs. ER vATPase, as well as the lysosome acidity in various types of iPSCs. The location of vATPase was determined by double immunostaining and colocalization targeting lysosome (LAMP-2), ER (Calnexin) and endosome (EEA) (FIG. 8A), and the cellular acidity vehicle were determined by the lysotracker (FIG. 8B). The amount of lysosome vATPase was significantly decreased in iPSCs from SAD by 39.7% (N=4, P<0.001 and FAD by 29.9% (N=4, P<0.05) (FIG. 8C *Compared with CON), which could be inhibited by dantrolene, especially in FAD iPSC (FIG. 8D *Compared with CON). Consistently, the cellular acidity vehicle was significantly decreased by 50% (N=4, P<0.0001) and 33.9% (N=4, P<0.01) respectively in both SAD and FAD iPSC compared to that of the normal control, which were also significantly inhibited by dantrolene (FIG. 8E *Compared with CON, +Compared with SAD, #Compared with FAD.).

Dantrolene Promoted Autophagy Activity in iPSC from AD Patients.

Figure 9A:
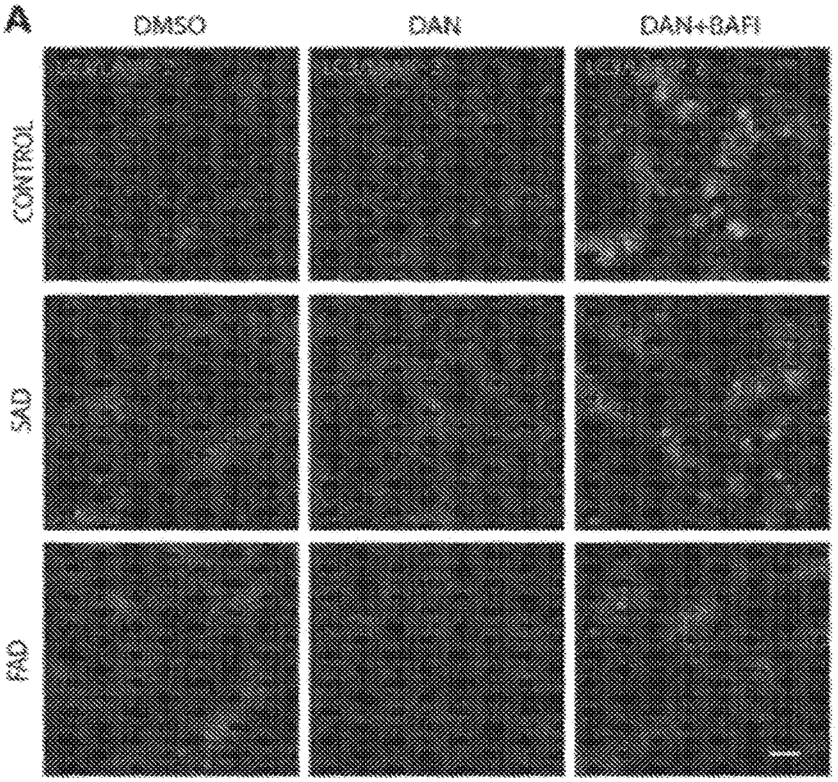
FIGS. 9A-9F show dantrolene increased LC3II levels in iPSCs from AD patients.
Figure 9B:
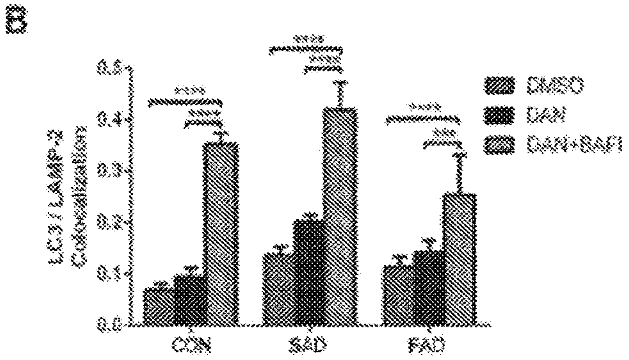
Figure 9C:
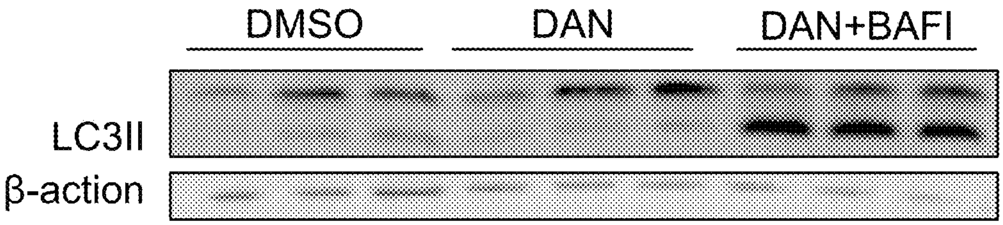
Figure 9D:
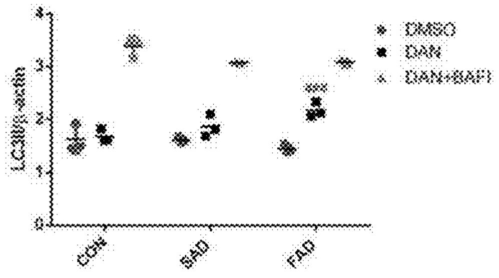
Figure 9E:
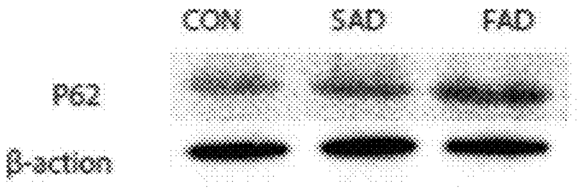
Figure 9F:
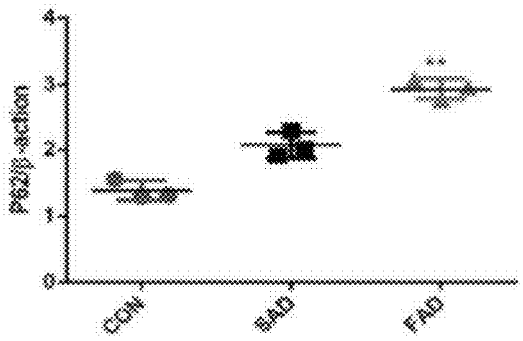

The effects of dantrolene on autophagy were further determined. The overall activity indicated by overall cellular level of autophagy biomarker LC3II was not significantly different among the three types of iPSC (FIGS. 9A-9C). However, dantrolene treatment increased LC3II level by 47.3% (N=5, P=0.3483) in SAD (FIG. 9B) and by 49.4% (N=3 P<0.001) in FAD (FIG. 9C #Compared with FAD) iPSCs respectively, which could be further elevated by the co-treatment with bafilomycin, an agent that impaired autophagy flux (FIGS. 9B, 9C). This suggests that dantrolene increased autophagy induction, rather than impairing autophagy flux. The impaired autophagy flux in SAD/FAD iPSCs was further supported by the significantly elevated p62 by 48.9% (N=3, P=0.3594) in SAD and by 110.9% (N=3, P<0.05) in FAD iPSC respectively (FIG. 9D *Compared with CON.).

This study indicates that neurogenesis from NPCs to common cortical and AD-specific deficient BFCN was significantly impaired in SAD/FAD patients, compared to in healthy human subjects, which could be inhibited by dantrolene. Also, dantrolene significantly inhibited synaptogenesis impairment in cortical neurons derived from iPSC of SAD/FAD patients. The RyR-2 numbers in SAD/FAD iPSC were abnormally increased, which contributed to the significant abnormal elevation of [$Ca^{2+}$ ]C triggered by NMDA receptor activation and the associated dysfunctional lysosome acidity and autophagy function. Consistently, dantrolene significantly inhibited NMDA-mediated disruption of intracellular $Ca^{2+}$ homeostasis and lysosome dysfunction, while also promoting autophagy activity in SAD/FAD cells.

The results from this study indicate that abnormally elevated RyR-2 (FIG. 5A-5D) and resultant $Ca^{2+}$ dysregulation (FIGS. 6A-6D, 7A-7G) in iPSC from AD patients were associated with the impaired lysosome acidity and function (FIGS. 8A-8E). Autophagy flux was consistently impaired in AD cells, but dantrolene seemed to primarily promote autophagy activity, although it also ameliorated impaired lysosome acidity and function. (FIGS. 8A-8E, 9A-9F). Dantrolene mediated inhibition of impaired neurogenesis/synaptogenesis in neurons derived from iPSCs from AD patients is associated with its ability to promote overall autophagy activity and to ameliorate the impaired lysosome function.

Example 2

Intranasal Administration of Dantrolene Increased its Concentrations and Durations in the Brain Intranasal dantrolene administration is proposed as a new therapeutic approach to maximize the potential neuroprotective effects of dantrolene in various neurodegenerative diseases, in particular AD, while minimizing its toxicity and side effects. As described herein, this study demonstrates that intranasal dantrolene administration in mice significantly increased the concentration and duration of dantrolene in the brain, compared to the commonly used oral administration.

Materials and Methods

Animals

All procedures were carried out in accordance with protocols approved by the Institutional Animal Care and Use Committee (IACUC) at the University of Pennsylvania. Male and female C57BL/6 mice, 2-4 months old, weighing 25-35 g, were used in all experiments. Mice were kept at 21-22° C. with a 12-hour light-dark cycle with food and water ad libitum. All efforts were made to minimize the suffering and number of mice.

Drug Administration

For the pharmacokinetic studies, mice were randomly divided into two experimental groups; intranasal dantrolene (N=4-13/group, N=13 for 20 minutes after intranasal administration; the experiments were repeated at this time point to confirm the repeatability and reliability.) and oral dantrolene (N=5) delivery. The vehicle is the same as that reported for RYANODEX® (Eagle Pharmaceuticals, Inc.), and consisted of 125 mg mannitol, 25 mg polysorbate 80, 4 mg povidone K12 in 20 mL of $ddH_2O$ and pH adjusted to 10.3. Dantrolene (Sigma, St Louis, MO) was diluted in the vehicle to a concentration of 5 mg/mL. For intranasal administration, the mice were held and fixed on the palm. 1 μL of drug formulation or vehicle per gram of body weight were delivered using a pipette. Several key steps were performed to assist with intranasal delivery: 1) the mouse's head was held so it was parallel to the floor; 2) the mouse was held so that it was not able to move its head or neck; 3) small droplets were ejected from the pipette; 4) 2-3 seconds were left for the mouse to inhale the solution before the next droplet was delivered; 5) the mouse was held for 10-15 seconds after the delivery was finished. This procedure took about 10 min/mouse. Oral administration was performed as previously described by Wu, Z., et al., Alzheimer Dis Assoc Disord 2015; 29:184, which is incorporated by reference in its entirety. The mice were placed in the same way, and 5 μL of drug per gram of body weight were delivered using a gavage attached to a microliter syringe.

Reducing dantrolene clearance from the brain was examined by intranasal administration of the inhibitors nimodipine (n=5) or elacridar (n=6) for primary protein (P-gp/BCRP) that pump dantrolene out of brains, as described by Fuchs, H., et al., Drug Metab Dispos 2014; 42:1761, which is incorporated by reference in its entirety. Nimodipine (Sigma, St Louis, MO) and elacridar (Sigma, St Louis, MO) were diluted in the vehicle, 2 mg/mL and 10 mg/mL, respectively. Intranasal nimodipine or elacridar or vehicle 1 μL/g of body weight was delivered 30 minutes before intranasal administration of 5 mg/mL dantrolene (1 μL/g of body weight). Tissue concentration of dantrolene was examined 20 min after intranasal dantrolene administration.

For the drug safety studies, the potential adverse effects of chronic administration of dantrolene were examined. Separate cohorts of mice were randomly divided into groups which received intranasal dantrolene (5 mg/kg) or intranasal vehicle, 3 times/week, for either 3 weeks or 4 months, as described above.

Sample Collection

Animals were anesthetized with 2-4% isoflurane and blood samples (0.2 mL) obtained by cardiac puncture after 10, 20, 30, 50, 70, 120, 150 and 180 minutes of dantrolene administration. The animals were then euthanized by intracardiac perfusion and exsanguination with PBS to ensure that dantrolene was completely washed out of the cerebrovascular system before the brains were harvested. Anticoagulated blood samples were centrifuged at 3000 rpm at 4° C. for 10 minutes and the supernatant collected. All procedures were performed in the cold room (4° C.). Both the plasma and brain samples were stored at −80° C. and protected from light until assayed. Separate cohorts of mice were euthanized as above after 3 weeks of chronic dantrolene administration and the smell or motor function tests.

High Performance Liquid Chromatography (HPLC)

An Aiglent Hewlett Packard Model 1100 Series, high performance liquid chromatography (HPLC) system (Aiglent Technologies), equipped with a refractive index monitor, was used for quantitation of dantrolene concentrations in the blood and brain. Acetonitrile was used as component A of the mobile phase, and potassium phosphate buffer solution (pH 7.0) as component B. The mobile phase had a flow rate of 1.0 mL/min with a proportion 12% to 88% for components A and B of the mobile phase, respectively. Detection was performed with the UV detector at 254 nm.

Behavioral Assays for Examination of Adverse Side Effects

Buried Food Test

Mouse olfaction was assessed in a separate cohort after 3 weeks of intranasal dantrolene (5 mg/kg, n=10) or vehicle (equivalent volume, n=10), using the buried food test, as described by Yang, M. and J. N. Crawley, Current protocols in neuroscience, 2009: p. 8.24. 1-8.24. 12, which is incorporated by reference in its entirety. Mice were randomly divided into two experimental groups (n=10/group). Dantrolene or vehicle was administrated once a day, three times a week (every other day during weekdays). After 3 weeks of chronic administration, animals were subjected to the buried food test. On day 1, cookies (1 cookie for 2 mice) were placed into the cages and left overnight. Cages were observed on the second day to make sure the cookies were consumed. On day 2 at about 4 μm, food was removed from the cages and the testing mice were fasted overnight, water available. On day 3 at about 11 am, mice were brought to the testing room and placed there for 1 hour for acclimation. Mice were then individually placed into a clean cage with 3 cm deep of bedding. The cookie was buried 1 cm beneath the bedding at the corner. The time the mouse took to retrieve the food and hold it with the front paw was recorded for a maximum of 900 seconds.

Rotarod Test

Motor coordination was examined with a rotarod, as described by Peng, J., et al., Neurosci Lett 2012; 516:274, which is incorporated by reference in its entirety, in a separate cohort of mice that were given either intranasal dantrolene (5 mg/kg, n=10) or vehicle (equivalent dose, n=10), once a day, 3 times/week, for 4 months. The animals received two 60 s training trials on the rotarod (IITC Series 8, Life Sciences, Woodland Hills, CA) at 9 rpm with a 30-minute interval between trials. The mice then underwent three test trials for a maximum of 120 s at variable speed, 4-40 rpm, with a 60 min interval between trials. The time spent on the rotarod was recorded for each mouse.

Statistical Analysis

Dantrolene concentrations were measured and reported as Mean±SEM and were analyzed with Student's t-test (two tailed) or one-way ANOVA followed by Tukey post hoc analysis. The significance level for all of this study's analyses was set at 95% ($P<0.05$). GraphPad Prism software (GraphPad Software Inc.) was used for all statistical analyses.

Results

Figures 10A, 10B, 10C, 10D:
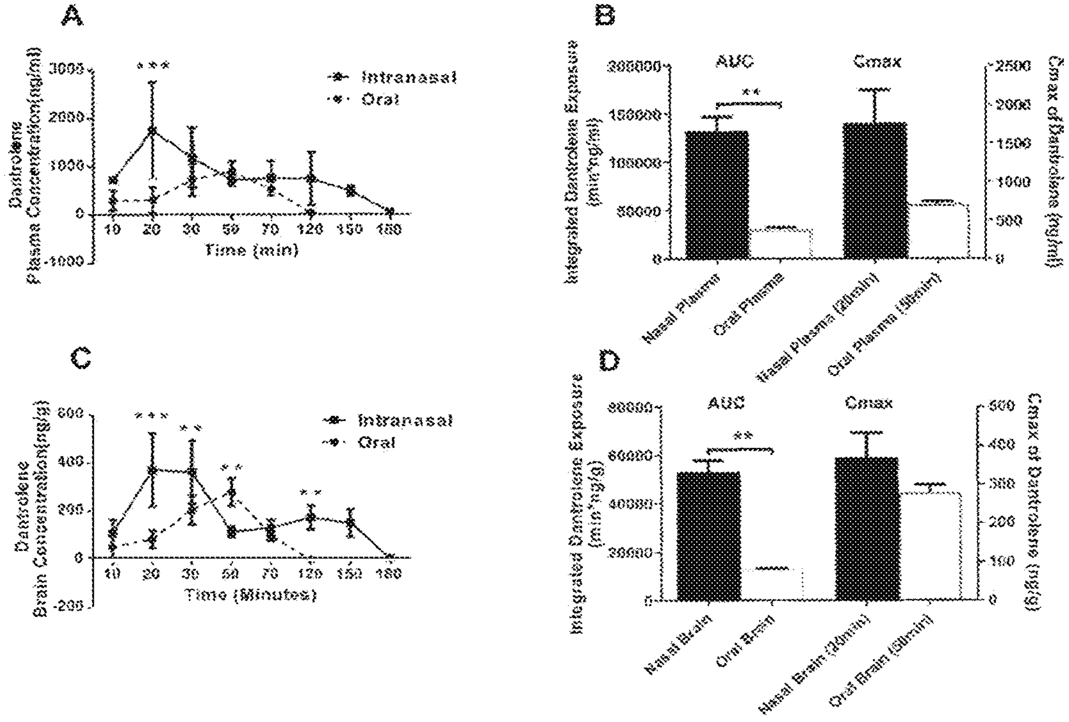
FIGS. 10A-10D show pharmacokinetic analysis of dantrolene in plasma and brain of mice after oral and intranasal administration.

Intranasal Dantrolene Administration Increased its Peak Concentrations and Durations in Brains Dantrolene pharmacokinetics were compared both in plasma and brain after oral and intranasal administration. Systemic absorption of dantrolene from the nasal route was slightly faster than from oral (FIGS. 10A, 10C). Peak dantrolene concentrations in both the plasma and brains after intranasal administration were significantly higher than those after the oral route (FIGS. 10A, 10C). The plasma dantrolene concentrations significantly decreased at about ~70 minutes after oral administration but maintained relatively high after intranasal administration (FIG. 10A). Similarly, the dantrolene concentration in the brain remained at a relatively high level for a significantly longer duration after intranasal administration (FIG. 10C, 180 minutes), than oral administration (FIG. 10C, ~70 minutes). Accordingly, the integrated dantrolene exposure in both plasma and brain were significantly higher after intranasal than after oral administration (FIGS. 10B, 10D).

Intranasal Dantrolene Time-Dependently Affects its Passage Across Blood Brain Barrier (BBB)

Figure 11:
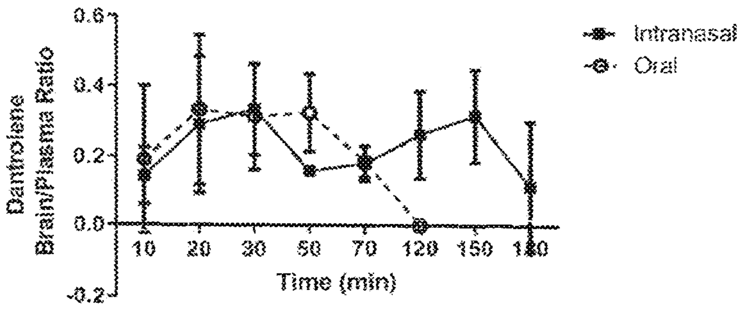
FIG. 11 shows the dantrolene concentrations in the brain over time after intranasal vs oral administration. Generally, there were no significant differences in the dantrolene brain/plasma ratios between intranasal and oral administration. At 50 minutes, the oral dantrolene brain plasma ratio was greater than intranasal dantrolene. The oral brain/plasma ratio fell to zero while the intranasal dantrolene brain/plasma ratio was sustained through 180 min. Data are expressed as Mean±95% CI, significance determined by multiple t-tests using the Holm-Sidak method with alpha=5.00%. %. Intranasal time points, 10, 30, 150, 180 min, n=5; 20 min, n=8; 50-120 min, n=4; oral time points, 10-120 min; n=5.

To examine whether intranasal dantrolene actually increased the passage of dantrolene across the BBB, the brain/plasma dantrolene concentration ratio was compared. Because the dantrolene plasma concentration is close to zero at 70 minutes after oral administration, only the dantrolene brain/plasma concentrations ratio at the time points before 120 minutes after administration were examined and compared because both plasma and brain dantrolene concentrations reached zero at 120 minutes after administration (FIGS. 10A, 10C). The dantrolene brain/plasma ratio after oral administration is relatively same as after intranasal approach at most time points (FIG. 11). However, the brain dantrolene after intranasal administration remained relatively high after 120 minutes after intranasal administration, because both plasma and brain dantrolene concentrations reached zero at 120 minutes after oral administration, but still maintained at certain level at 150 minutes after intranasal administration (FIGS. 10A, 10C).

Chronic Use of Intranasal Dantrolene Did not Impair the Smell Function

Figures 12A, 12B:
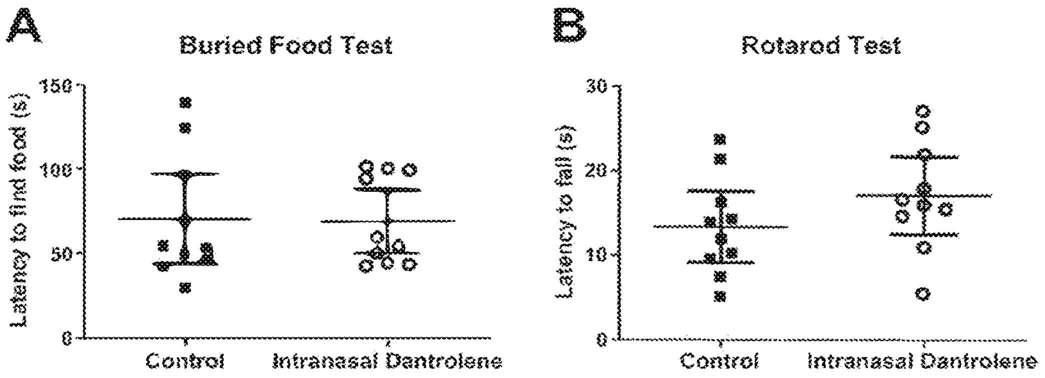
FIGS. 12A-12B show long-term intranasal administration of dantrolene did not affect olfaction or motor function.

To examine the possible nose membrane damage and dysfunction of smell by chronic intranasal administration of dantrolene, smell function tests were performed in mice after 3 weeks or 4 months of intranasal administration at 5 mg/kg, three times a week. Intranasal dantrolene did not affect smell function, indicating that dantrolene did not have significant side effects on smell function after chronic nasal administration (FIG. 12).

P-gp/BCRP Inhibition Did not Increase Dantrolene Concentrations in the Brain

Figure 13:
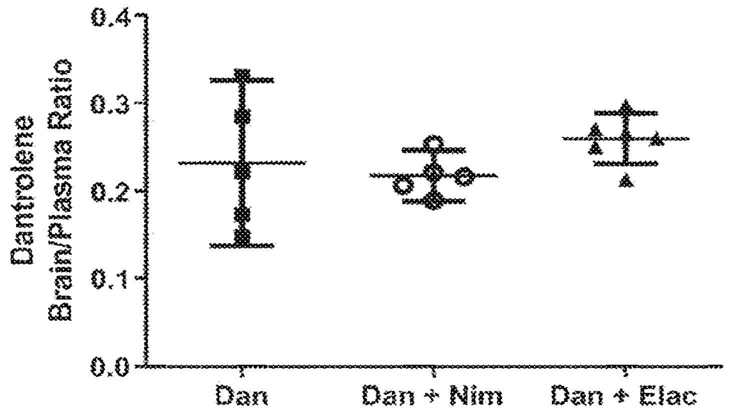
FIG. 13 shows blood brain barrier (BBB) inhibitors, nimodipine and elacridar, had no effect on dantrolene passage. After 20 minutes of intranasal administration of dantrolene (5 mg/kg), in the presence or absence of BBB pump inhibitors (P-gp/BCRP), nimodipine (Nim, 2 mg/kg) or elacridar (Elac, 10 mg/kg), all dissolved in the same vehicle as Ryanodex, the dantrolene brain/plasma ratios were determined as a measure of dantrolene passage across the BBB. No significant differences were detected with either inhibitor compared to dantrolene alone. The data are expressed as the Mean±95% CI, n=5 (Dan, Dan+Nim), n=6 (Dan+Elac, and analyzed with the Kruskall-Wallis non-parametric ANOVA with Dunn's multiple comparison test.

Whether the P-gp/BCRP inhibitor nimodipine or elacridar would increase dantrolene brain concentrations was examined. Neither nimodipine nor elacridar significantly increased dantrolene brain/dantrolene plasma concentration ratios (FIG. 13).

This study shows that intranasal dantrolene administration, when compared with oral administration, using a RYANODEX® (Eagle Pharmaceuticals, Inc.) formula significantly increased its concentrations and duration in the brain, without obvious side effects on smell, liver or motor function. Intranasal dantrolene did not increase its passage across BBB during the first 70 minutes after administration as there was no significant difference in the ratio of brain concentration to plasma concentration over this time period. Inhibitors of P-gp/BCRP pumps did not play a role in the varying dantrolene brain concentrations. Chronic use of dantrolene to treat patients with various neurodegenerative diseases including AD is thus both feasible and tolerable. Intranasal dantrolene significantly increases the peak brain concentrations, compared to commonly used oral approaches, providing a new method of making dantrolene reach the minimum therapeutic concentrations to treat various neurodegenerative diseases, including AD. Furthermore, the duration of dantrolene in the brain lasted much longer after intranasal administration than after oral administration, making the overall exposure in the brain significantly increased. Overall greater brain dantrolene exposure will significantly increase the chance of successful dantrolene neuroprotection in various neurodegenerative diseases, including stroke and AD, with potentially reduced side effects. The results of this study demonstrate that brain concentrations with intranasal administration were 479 nM (150.53 ng/g) (FIG. 10C) at 150 min, compared to 0 nM with the oral approach. A relatively lower dose of intranasal dantrolene as compared to oral administration to reach minimally required brain concentrations for neuroprotection is thus possible while minimizing significant peripheral side effects. Intranasal dantrolene administration is associated with a lower plasma dantrolene concentration than is associated with oral dantrolene administration. The intranasal approach also avoids liver first pass metabolism, unlike oral administration. This is an important new method for treatment of and neuroprotection in various neurodegenerative diseases, including AD.

Intranasal dantrolene in this study did not increase its passage across the BBB when compared to the oral approach during the first 70 minutes. However, because of the longer duration of dantrolene concentrations in the brain, the dantrolene plasma/brain concentration ratio between 120 and 150 minutes after intranasal administration can were still be calculated but not after the oral approach when both plasma and brain dantrolene concentration reached zero. This study herein indicates that intranasal administration of dantrolene for three weeks did not affect smell function, nor did it affect motor function or cause obvious side effects after up to four months of nasal treatment. These results indicate that chronic administration of dantrolene is relatively safe, making its long-term use for treatment of AD feasible. This new method that can maintain dantrolene brain concentration and duration, but reduce plasma concentration, will make its chronic use more tolerable and practicable.

In summary, intranasal dantrolene administration using the RYANODEX® formula significantly increased brain peak concentrations and duration, without any obvious significant side effects even after chronic use, providing a new potential approach for augmenting dantrolene neuroprotection in various neurodegenerative diseases, including to treat AD and the cognitive impairments manifested therein.

Example 3

Intranasal Dantrolene as a Disease-Modifying Drug in Alzheimer's 5XFAD Mice

This study investigated the plasma and brain concentrations and the therapeutic effects of intranasal dantrolene in 5XFAD mice and associated side effects, not only as a symptom-relieving but also as a disease-modifying drug, and compared to the subcutaneous approach as done in a different FAD animal model, as described by Peng J, et al., Neurosci Lett 2012; 516:274, which is incorporated by reference in its entirety.

Materials and Methods

Animals

All the procedures were approved by the Institutional Animal Care and Use Committee (IACUC) at the University of Pennsylvania. Two pairs of 5XFAD mice (B6SJL-Tg (APPSwFIL on, PSEN1*M146L*LV286V) 6799Vas/Mmjax) and wild type mice (B6SJLF1/J) mice were purchased from the Jackson Laboratory (Bar Harbor, ME) and bred. These 5XFAD transgenic mice overexpress mutant human APP with the Swedish (K670N, M671L), Florida (1716V), and London (V717I) familial Alzheimer's Disease (FAD) mutations along with human PS1 harboring two FAD mutations, M146L and L286V, as described by Oakley H, et al., J Neurosci. 2006; 26:10129, which is incorporated by reference in its entirety. The 5XFAD mouse model is an aggressive AD animal model with intracellular amyloid first appearing at 2 months of age, and cognitive dysfunction beginning at 6 months of age, which is suitable to test drug efficacy, as described by Hillmann A, et al., Neurobiol Aging 2012; 33 833, which is incorporated by reference in its entirety. Animals were housed in the animal facility of the University of Pennsylvania, under a 12-h light cycle and controlled room temperature. Food and water were available in the cage. All mice were weaned no later than one month old and genetically identified by polymerase chain reaction (PCR) analysis before weaning. At this time, mice were divided into different cages according to age and gender, with no more than 5 mice per cage. Both male and female mice were used in this study.

Intranasal Vs Subcutaneous Dantrolene Administration and Drug Concentration Measurements Dantrolene Administration WT mice at two months old were randomly divided into intranasal (N=5) or subcutaneous (N=5) groups, receiving dantrolene dissolved in the same vehicle as for RYANODEX® (dantrolene sodium, Eagle Pharmaceuticals, Inc., New Jersey), consisted of 125 mg mannitol, 25 mg polysorbate 80, 4 mg povidone K12 in 5 mL of sterile water for injection and pH adjusted to 10.3. Dantrolene (Sigma, St Louis, MO) was diluted in the vehicle to a concentration of 5 mg/mL and 1 mg/mL for intranasal or subcutaneous administration, respectively. For intranasal administration, the mice were held by the scruff of their necks with one hand and with the other hand a total of 1 μL/gram of body weight of dantrolene solution or vehicle per gram of body weight was delivered using a pipette. For example, a mouse weighing 20 g would have been given 20 μl solution. The solution was slowly delivered directly into the mouse's nose, as described previously by Med Lett Drugs Ther. 2015; 57:100, which is incorporated by reference in its entirety. Care was taken to make sure that mice were minimally stressed, and that the respective solution stayed in the nasal cavity and did not enter the stomach or lungs. Subcutaneous dantrolene administration was performed, as previously described, by Peng J, et al., Neurosci Lett. 2012; 516:274, which is incorporated by reference in its entirety, with a total subcutaneous injection of 5 μl per gram of body weight.

Measurements of Dantrolene Concentrations

Wild type mice at 2 months of age were given subcutaneous or intranasal dantrolene at the dose of 5 mg/kg for one time. Plasma or brain tissues were obtained at 20 or 60 minutes after drug administration, as described by Peng J, et al., supra. Plasma or brain dantrolene concentrations were determined by High Performance Liquid Chromatography (HPLC) using an Agilent Hewlett Packard Model 1100 Series and the methods, as described by Peng J, et al., supra. Briefly, the frozen brain tissue was placed into 200 μl of mixture solution (acetonitrile:$H_2O$, 2:1) and homogenized, the suspensions were then centrifuged at 4.161 Cat 20,000×g for 20 min, 50 μl of supernatant was injected into HPLC for analysis. Acetonitrile was used as component A of the mobile phase, and potassium phosphate buffer solution (pH 7.0) as component B. The mobile phase had a flow rate of 1.0 mL/min with a proportion of 12% to 88% for components A and B of the mobile phase, respectively. Detection was performed with the UV detector at 254 nm. Protein was not precipitated from the brain or plasma.

Dantrolene Treatment and Experimental Groups

Figure 14:
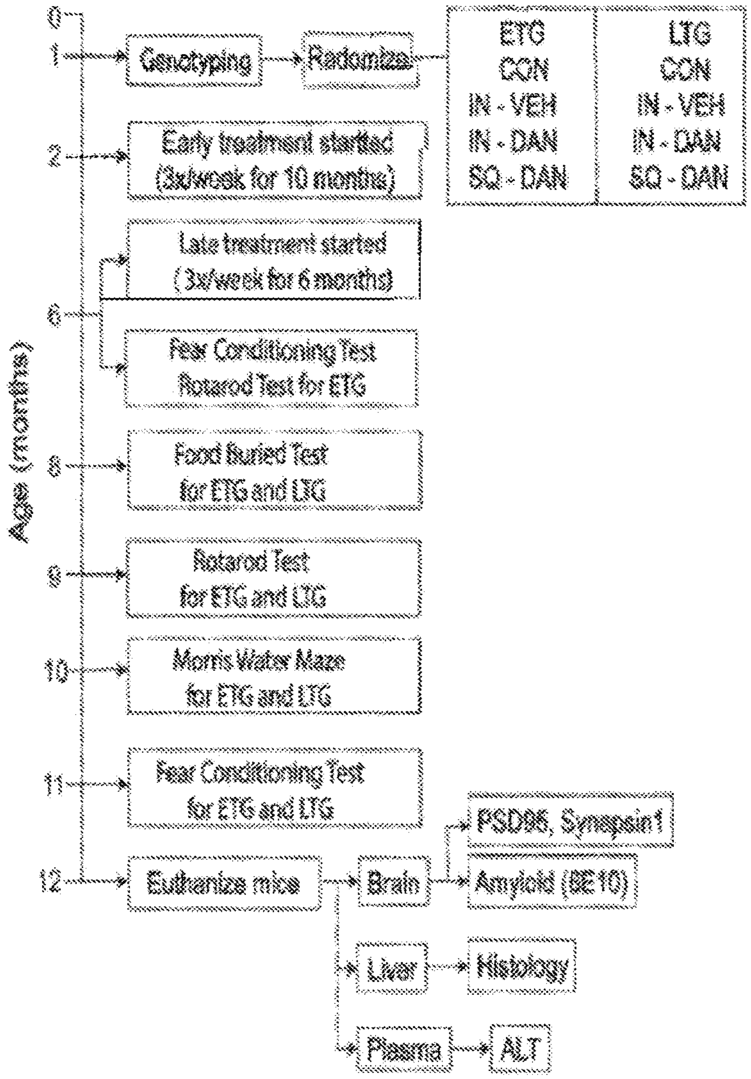
FIG. 14 shows the experimental design of Example 3: Timeline for treatments, behavioral tests and euthanasia. Twelve experimental groups were designed based on the genotype (5XFAD, WT), the age when the treatment started (Early Treatment (ETG), Late Treatment (LTG) groups) and the administration route of the treatment (Intranasal, Subcutaneous).

Both age-matched male and female mice were used in this study. All the mice were randomly divided into 12 groups when they were genotyped around 1 month old. The first 8 groups were named as Early Treatment Group (ETG, see FIG. 14), since treatments for these groups started when the animals were 2 months old, before onset of primary amyloid pathology and appearance of cognitive dysfunction. The next 4 groups were named Late Treatment Group (LTG, see FIG. 14), since dantrolene treatments started when the animals were 6 months old, well after onset of amyloid pathology and cognitive dysfunction, to determine dantrolene as a disease modifying drug. Animals in different treatment groups received intranasal dantrolene (IN-DAN), subcutaneous dantrolene (SQ-DAN), intranasal control vehicle (IN-VEH) or no treatment (CON, negative control). Animals in the ETG were treated (Monday, Wednesday, and Friday) beginning at 2 months of age, before the onset of intracellular amyloid pathology and any cognitive dysfunction. The Late Treatment Groups (LTG), intranasal dantrolene (IN-DAN) and subcutaneous dantrolene (SQ-DAN), began the same treatment at 6 months of age, well after the onset of extracellular amyloid plaques accumulation and cognitive dysfunction. Control vehicle was made fresh and contained all inactive ingredients in Ryanodex, Med Lett Drugs Ther. 2015; 57:100. Fresh dantrolene at 5 mg/mL or 1 mg/mL dose level were used for, respectively. Fresh dantrolene solutions were made every time before administration with the vehicle for intranasal (5 mg/ml) and subcutaneous (1 mg/ml) administration. All mice continued to receive treatment until they were euthanized at 12 months of age.

Buried Food Test

Smell function was assessed in all groups at 8 months of age using a 3-day protocol for the buried food test, as described by Yang M, et al., Curr Protoc Neurosci. 2009; 48:8.24, which is incorporated by reference in its entirety.

On the first day, the mice were kept in their housing cage under the general situation; cookies (Galletas La Moderna, S. A. de C. V.; 1 cookie for every 2 mice) were buried beneath the cage bedding for 24 hours, and then the number of cookies were consumed were recorded. The mice were fasted beginning on the second day at 4 μm and ending on the third day at 9 am. Water was freely available during this time.

The buried food test was conducted on the third day at approximately 9-11 am. They were acclimated to the testing room for at least 1 hour before the test. Mice were individually placed into a clean cage containing clean bedding with one cookie buried beneath the bedding in a corner. The latency for the animal to find the cookie (identified as catching the cookie with its front paws) was recorded manually. If the animal failed to find the cookie within 15 minutes, it would be placed back into its home cage. A clean cage and bedding were used for each animal and investigators were blinded to the experimental conditions.

Rotarod Test

Motor function was examined for detecting muscle weakness, a common side-effect of dantrolene as a muscle relaxant. The amount of time spent on the accelerating rotarod (IITC Series 8, Life Sciences, Woodland Hills, CA) was assessed for mice in the ETG at 6 months of age (data not shown) and for all groups at 9 months of age, as described by Peng J, et al., supra. Briefly, animals were acclimated to the testing room at least 1 h before the test. Two 60 s training trials at a constant speed (9 rpm) were performed with a 30 min interval. Then, three 120 s test trials were conducted at a gradually increasing speed (4-40 rpm) with a 60 min interval between trials. The latency to fall from the rotarod was recorded automatically and analyzed.

Fear Conditioning Test

Memory and learning was assessed at 6 and 11 months of age for the ETGs, but only at 11 months of age for LTGs. Both hippocampal-dependent and -independent memory were assessed using the fear conditioning test, as described by Zhang Y, et al., Ann Neurol 2012; 71:687, which is incorporated by reference in its entirety. Animals were brought to the testing room at least 1 hour before the test in order to get acclimated to the testing room. On the first testing day, each mouse was placed in the test chamber and went through three condition-stimulation parings with a 60-second interval between each cycle. A 30-second tone of 2000 Hz and 85 dB was used as the tone stimulation, and a 2-second electrical foot shock of 0.7 mA was used as the shock stimulation. The mice were removed from the chamber 30 seconds after the last stimulus. On the second day, the contextual fear conditioning test was first performed to measure the hippocampal-dependent memory. The mouse was placed in the same chamber for 6 minutes with no tone or shock, and then removed from the chamber. Two hours later, the cued fear conditioning test was performed to measure the hippocampal-independent memory. The mouse was placed in another chamber that was different in size and smell using different cleaning solutions. There was no tone or shock during the first 3 minutes. Later the mouse went through 3 cycles of the same tone with a 60-second interval between each cycle with freezing time recorded. Animals were then removed from the chamber 60 seconds after the last tone. The ANY-maze controlled Fear Conditioning System consisted of a sound-attenuating chamber (Model: 46000-590, UGO Basile, Gemonio Italy) equipped with a video camera and ANY-maze software (V.4.99 Stoelting Co. Wood Dale, IL) which recorded the freezing time. The chamber was thoroughly cleaned between trials with a 75% alcohol solution on the first day in the training trials and on the second day in the contextual-fear conditioning test, and with water on the second day in the cued-fear conditioning test. The investigator was blinded to the treatment groups.

Morris Water Maze

Learning and memory were also measured for all groups at 11 months of age using the Morris water maze (MWM). Briefly, a 1.5 m diameter pool filled with water and a 15 cm platform were used throughout the whole test. The water was opacified with titanium dioxide and the temperature was controlled at 21-24° C. During the first 5 days (day 1 to day 5), the mice went through 4 days of cued trials. The pool was surrounded by a white curtain and the platform was submerged 1-1.5 cm under the water with a flag on the top as a cue for the mice. The location of the platform and the starting points were random during the cued trials. When the mouse escaped from the pool onto the platform, it was allowed to stay there for 15 s. If the mouse failed to find the platform, the experimenter would gently guide it onto the platform. The latency for each mouse to find the platform was recorded. During the next 5 days (day 6 to day 10), the animals went through 4 place trials every day. The curtain and platform were removed. There were several visual cues on the wall. The location of the platform was fixed, and the starting points were random. The situation of the testing room was kept consistent from then on. Similar to the cued trials, the mouse remained on the platform for 15 s before it was removed from the pool, or the mouse was guided to the platform if it failed to find the platform within 60 s. The latency for each mouse to find the platform was recorded. The mouse went through a probe trial the next day (day 11) in which the platform was removed. The starting point was fixed in the opposite quadrant from where the platform was located. The time each mouse spent in each quadrant was recorded. The ratio of the time each mouse spent in the target quadrant compared to the opposite quadrant was calculated.

Tissue Preparation

Mice were sacrificed at 11-12 months old after all the behavior tests were finished. As described previously, animals were anesthetized with 2-4% isoflurane delivered through a nose cone, and the concentrations was adjusted according to the animals' response. Blood was harvested from the heart using a syringe equipped with a 30G needle. The blood was centrifuged at 3000 rpm at 4° C. for 10 minutes, the supernatant collected and frozen at −80° C. The plasma samples were protected from light if used for the concentration study. Transcardial perfusion with cold phosphate buffered saline (PBS) was performed before the liver and brain were removed. The whole brain was dissected for the brain concentration study, which was protected from light and frozen at −80° C. For the dantrolene treatment groups, the liver and brain were dissected. The liver and the left half of the brain were post-fixed in 4% paraformaldehyde overnight at 4° C. and paraffin-embedded for sectioning. Several animals from each group were randomly selected to be sectioned for the immunohistochemical and histological and studies, and the exact numbers of animals for each assessment are presented in each figure legend. The right half of the brain was frozen at −80° C. for biochemical assays.

Immunohistochemistry Staining

Paraffin-embedded coronal brain sections (10 μm) were made for immunohistochemistry staining, as described by Peng, J., et al., 2012. supra. Briefly, sections were deparaffinized and hydrated. Antigen retrieval was performed in Antigen Unmasking Solution in the pressure cooker. Then the sections were incubated in 10% normal goat serum (NGS) for 30 minutes, in M.O.M Mouse Ig Blocking Reagent (PK-2200, Vector Lab) for 1 hour and in M.O.M diluent for 5 minutes, successively. Slides were incubated with primary antibody, anti-6E10 (1:500, 803001, Bio Legend, San Diego, CA), at 4° C. overnight, followed by incubation with M.O.M Biotinylated Anti-Mouse IgG reagent (PK-2200, Vector Lab) for 10 minutes and with VECTASTAIN ABC Reagent for 5 minutes, respectively. Then the sections were dehydrated and cover-slipped with Permount. All images were taken on an Olympus (BX51W1) microscope equipped with a Q Imaging Retiga 2000R digital camera and i Vision imaging software (Bio Vision Technologies, Exton, PA). Cell numbers per area were quantified using Image J software by investigators who were blinded to the groups. The number of plaques per area and the percent area occupied by plaques in the entire hippocampus and dentate gyrus were calculated.

Western Blot

The synaptic density was assessed by the expression of particular proteins by western blot analysis, as described by Peng, J., et al., 2012. supra. Briefly, the samples were lysed in ice-cold RIPA containing protein inhibitor. The concentration of protein was measured using Bicinchoninic Acid (BCA) Kit (23227, Thermo Fisher Scientific, Waltham, MA). A mixture of each protein with 4× loading buffer and $ddH_2O$ was produced respectively to reach the same volume of the mixture and same amount of the protein. Equal sample amounts were loaded on SDS-polyacrylamide gel electrophoresis and transferred to nitrocellulose membrane. The membrane was incubated with 5% non-fat milk at room temperature for 1 hour, followed by incubation with primary antibody PSD95 (1:500, 810401, Bio Legend, San Diego, CA), synapsin1 (1:500, 515200, Fisher Scientific, Pittsburgh, PA) and β-actin (1:2000, A5441, Sigma, St. Louis, MO) respectively, at 4° C. overnight. The membrane was incubated with relevant secondary antibody at room temperature for 1 hour. Blots were detected using an enhanced chemiluminescence detection system (Millipore, Billerica, MA). Density of target protein normalized to β-actin was calculated using image J software. (National Institutes of Health, Bethesda, MD).

Plasma ALT Activity Assessment

Plasma ALT activity, an indicator of liver function, was measured using an Alanine Aminotransferase (ALT) Activity Colorimetric Assay Kit (K752, Biovision (Milpitas, CA, USA) according to the manufacturer's instructions. The plasma ALT activity for the ETGs and LGTs which were treated with dantrolene for the longest time (11 months) was measured. Briefly, 10 μL plasma was diluted in a total 100 μL reaction mix, including 86 μl ALT Assay Buffer, 2 μl OxiRed Probe, 2 μl ALT Enzyme Mix, and 10 μl ALT Substrate, to analyze the pyruvate transformed from a-ketoglutarate with alanine. A pyruvate standard curve was generated at the same time, using pyruvate concentrations of 0, 2, 4, 6, 8, 10 nmol/well. The optical density (OD) at 570 nm was measured at 10 min (A1) then again at 60 min (A2) after incubating the reaction at 37° C. The pyruvate concentration was measured in a linear range of the standard curve. ALT activity was calculated using the formula: ALT activity=(A2-A1)/50*10 mU/mL.

Liver Pathological Assessment

Liver sections (5 μm) were imaged for pathological assessment. Three animals from each ETG, with three sections per animal, were selected randomly for pathology assessment and the slides were blinded to the investigators. The sections were stained with hematoxylin and eosin (H&E) and then imaged on an Olympus BX51W1 microscope. Sections were evaluated for hepatic injuries, such as acute or chronic hepatitis, inflammation, fibrosis, necrosis, cirrhosis, bile stasis, and unspecific hepatocyte abnormities.

Statistical Analysis

The number of animals in each group was determined, as described previously by Peng, et al., Alzheimers Dement 7:e67, and are listed in each figure legend. Statistical analyses were performed by Graph Pad Prism 8.0 and are described in each figure legend. Repeated measures by ANOVA were not always possible due to mortality. Data are expressed as means with 95% CI. It was accepted as a statistically significant difference when p values were less than or equal to 0.05. (P<0.05).

Intranasal Dantrolene Increased Blood Brain Barrier (BBB) Passage and Brain Concentration Compared to Subcutaneous Administration.

Figure 15B:
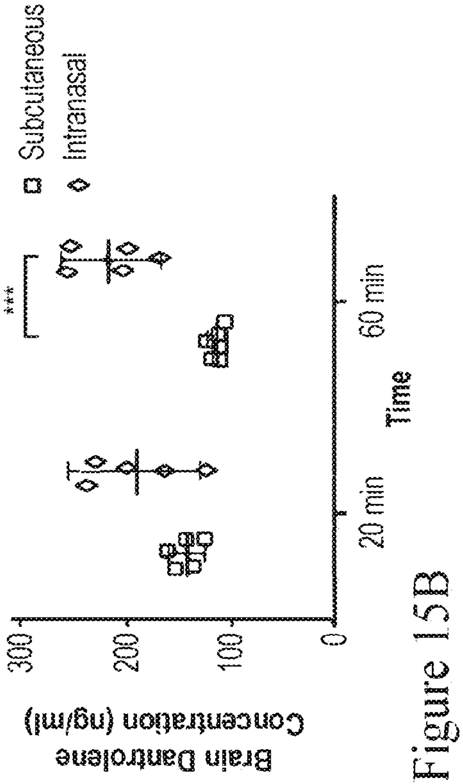
FIGS. 15A-15D show intranasal dantrolene provided greater drug penetration into the brain and higher brain concentrations than subcutaneous dantrolene.
Figure 15A:
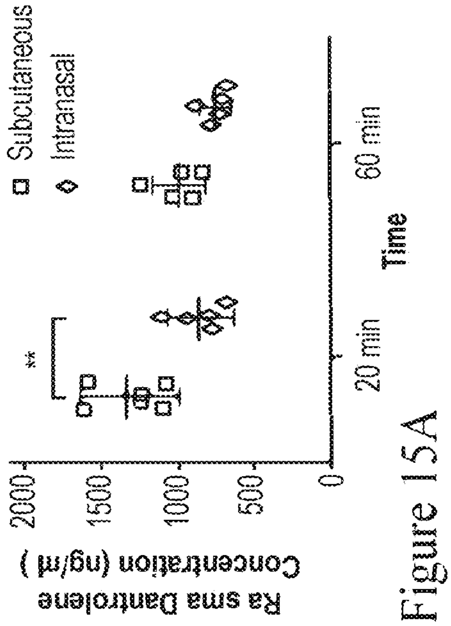
Figure 15D:
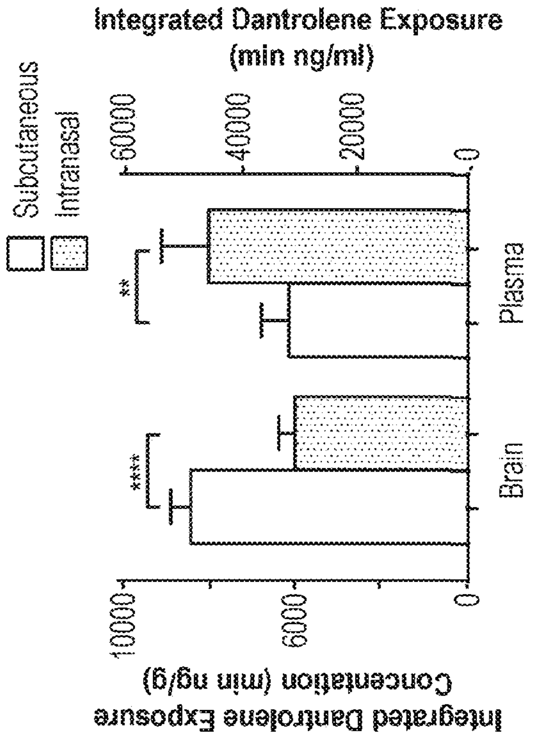
Figure 15C:
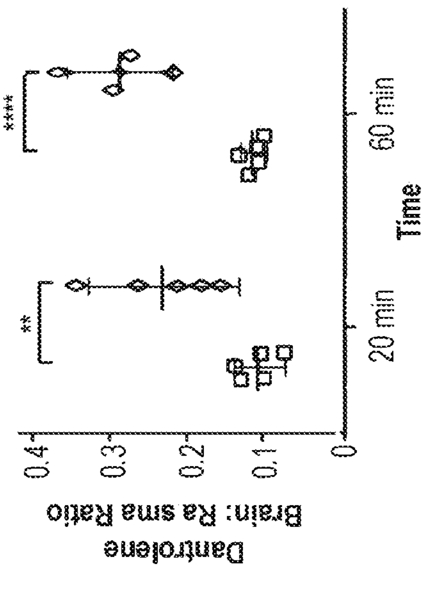

The limited BBB permeability of dantrolene observed after systemic administration has restricted the use and potential effectiveness of the drug. The intranasal dantrolene administration in this study resulted in lower plasma concentrations, determined at 20 minutes after administration, compared to the subcutaneous approach (see FIG. 15A). In contrast, the intranasal dantrolene administration resulted in brain concentrations substantially higher than subcutaneous administration at 60 minutes after dosing (see FIG. 15B). In combination, the brain/plasma dantrolene concentration ratio (see FIG. 15C), a variable often used to indicate drug penetration across BBB, was significantly higher at both time points after intranasal administration compared to the subcutaneous approach. The integrated overall dantrolene exposure in the brain was significantly higher after intranasal than subcutaneous administration (FIG. 15D, left panels). In contrast, the integrated overall dantrolene exposure in plasma was significantly lower after intranasal than subcutaneous administration (FIG. 15D, right panels).

Early Intranasal or Subcutaneous Dantrolene Treatment Ameliorated Memory Loss in 5XFAD Mice.

Figure 16B:
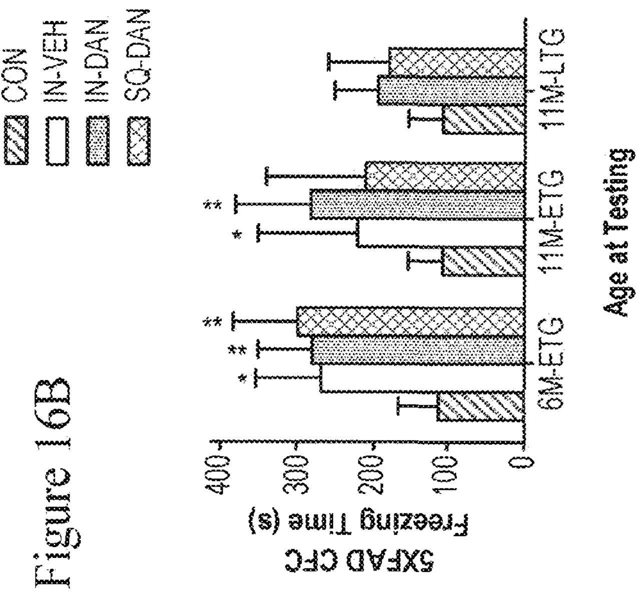
FIGS. 16A-16B shows intranasal administration of dantrolene had better therapeutic effects on memory in AD mice. Memory was assessed with both contextual fear conditioning (CFC; hippocampus-dependent) and cued fear conditioning (FC-cued; hippocampus-independent) tests. The test was performed after 4 and 9 months of treatment, at 6 (6M) and 11 (11M) months of age, respectively, for the Early Treatment Group (ETG) and after 5 months of treatment at 11 months of age for the Late Treatment group (LTG).
Figure 16A:
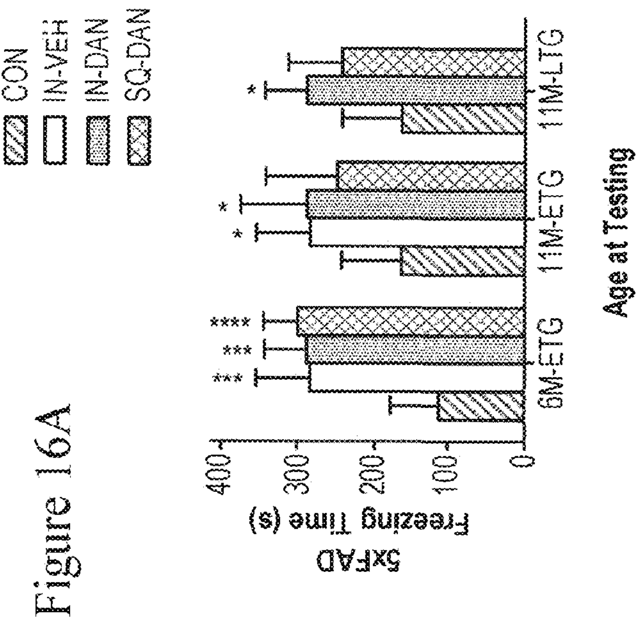
Figures 19A, 19B:
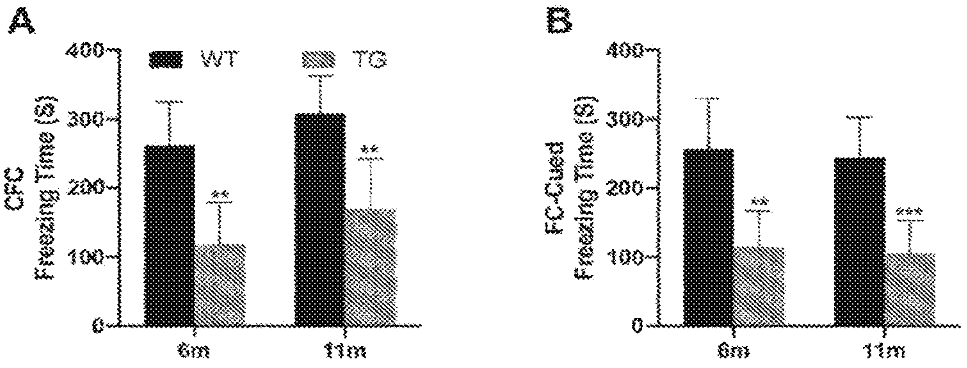
FIGS. 19A-19A show memory impairment in untreated wild-type and 5XFAD mice. Both contextual fear conditioning (CFC, hippocampal-dependent) and cued fear conditioning (FC-cued, hippocampal-independent) memory were assessed with fear conditioning tests (FC).
FIG. 19B similarly shows that hippocampal-independent memory was significantly impaired in the 5XFAD-CON mice compared to WT-CON mice at 6 and 11 months of age (P=0.0019, P=0.0004, respectively), analyzed using unpaired t-test. Genetics (WT versus TG) were found to be a significant source of variation for impaired memory (P<0.0001, F(1,47)=27.94). Data are presented as Mean with 95% CI. (WT: 6M n=13, 11M n=12; TG: 6M n=13, 11M n=13).
Figure 20A:
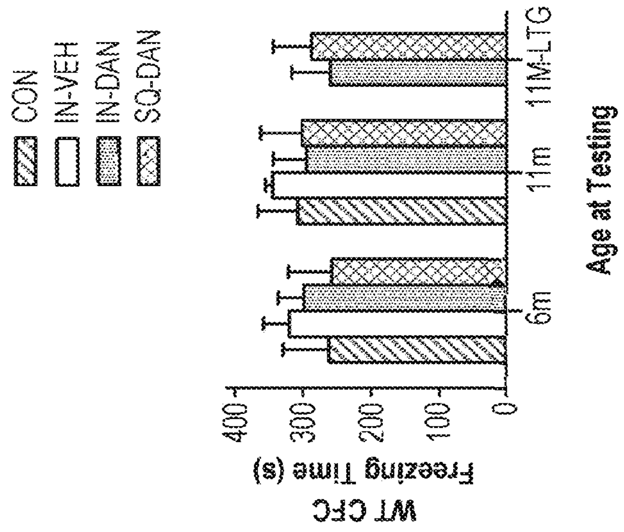
FIGS. 20A-20B show memory in wild-type (WT) mice. Memory was assessed using both contextual fear conditioning (CFC; hippocampal-dependent) and cued fear conditioning (FC-cued; hippocampal-independent) tests. The test was performed after 4 and 9 37 months of treatment, at 6 (6M) and 11 (11M) months of age, respectively, for the Early Treatment Group (ETG) and after 5 months of treatment at 11 months of age for the Late Treatment Group (LTG).
Figure 20B:
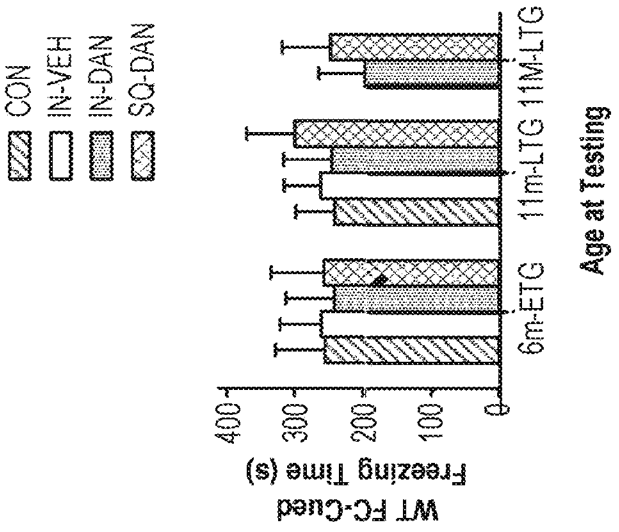

Both hippocampal-dependent and hippocampal-independent memory were assessed at 6 months and 11 months old, respectively, which was after 4 and 9 months of dantrolene treatment in the ETG (See FIGS. 16A-16D) and after 5 months of treatment in the LTG at 11 months of age. Both measures of cognition were significantly impaired in the 5XFAD controls compared to the WT controls (FIGS. 19A-19B) which confirms the aggressive AD phenotype in the 5XFAD model. In 5XFAD mice, intranasal dantrolene treatment significantly improved hippocampal-dependent (see FIG. 16A) and hippocampal-independent (see FIG. 16B) memory at both 6 and 11 months of age for the ETG group compared to 5XFAD controls without any treatment (FIGS. 16A-16B) Intranasal dantrolene also significantly ameliorated hippocampal-dependent memory loss at 11 months of age for the LTG and tended to improve hippocampus-independent memory (FIGS. 16A-16B). Interestingly, the intranasal vehicle also ameliorated hippocampal-dependent memory loss at both 6 and 11 months of age, though it only improved hippocampal-independent memory at 6 months of age in the 5XFAD ETG. Subcutaneous dantrolene ameliorated both types of memory loss at 6 but not 11 months of age in the ETG, and it did not have beneficial effects at 11 months of age in the LTG (FIG. 16A-16B). Dantrolene administration, by either route, had no effect on memory in wild type mice (FIGS. 20A-20B). The freezing times for the dantrolene treated 5XFAD mice are comparable to the WT freezing times (FIGS. 20A-20B), further supporting the improved memory in the transgenic mice.

Figures 21A, 21B, 21C, 21D, 21E, 21F:
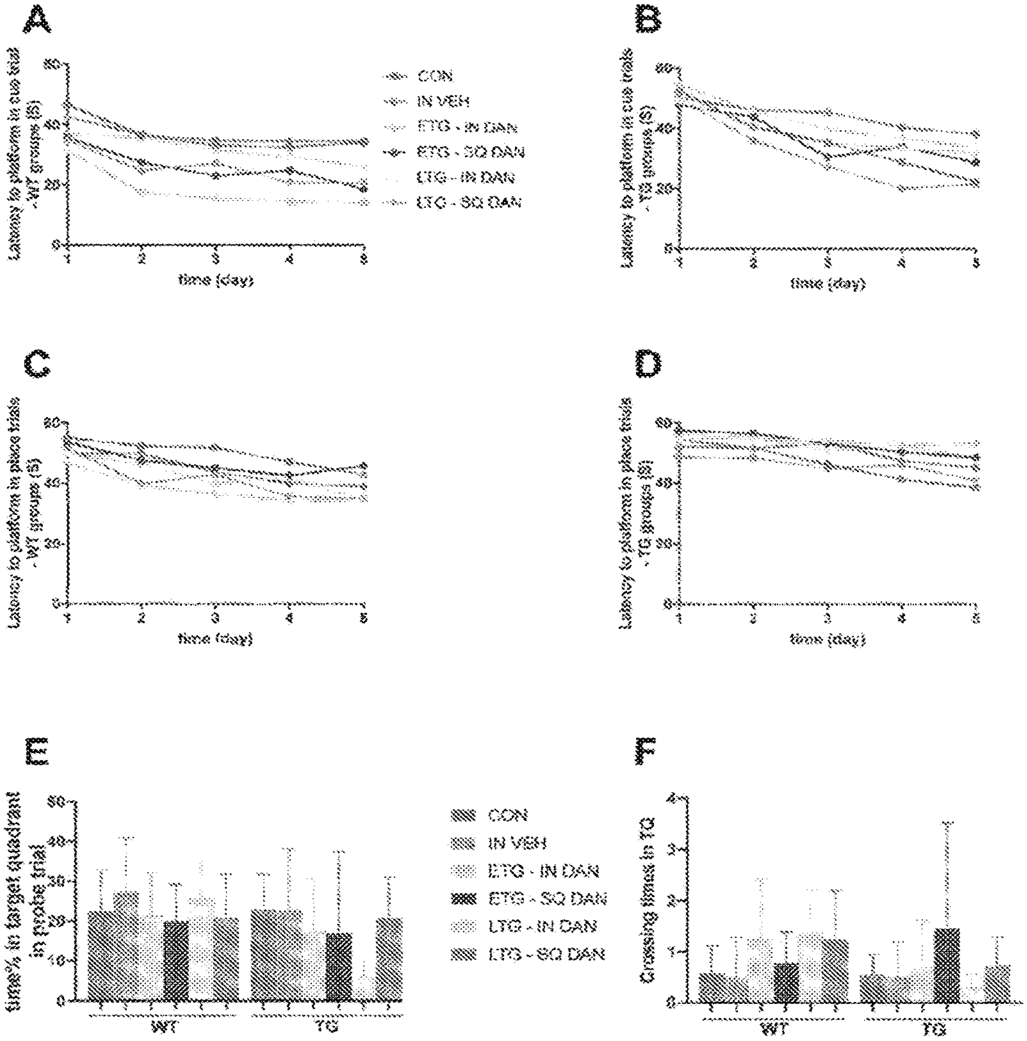
FIGS. 21A-21F show learning and memory determined by Morris Water Maze (MWM) test. Learning and memory were determined by MWM at age of 10 months for both wild type (WT) and 5XFAD (TG) groups.

Hippocampal-dependent learning and memory were examined using the MWM at age 10 months of age for both genotypes. No significant differences were found for the cued trials for all treatment groups compared to either untreated wild-type (WT) or 5XFAD (TG) controls over time (FIGS. 21A-21B). In the place trials, there were no significant differences in the escape latency for all the groups compared to controls, no matter the genotype or the treatment (FIGS. 21C-21D). The animals learned the task over time but there were no differences between the treatment groups nor between the genotypes. There were no significant differences found among all the groups compared to controls in the data for the time spent in the target quadrant (FIG. 21E) and the number times the mice crossed the platform (FIG. 21F).

Intranasal but not Subcutaneous Dantrolene Treatment Ameliorated Memory Loss in 5XFAD as a Disease-Modifying Drug.

Both hippocampus-dependent and hippocampus-independent memory were assessed using FCT for LTGs at 10 months old, with intranasal or subcutaneous dantrolene treatment started at 6 months old when both AD pathology and symptoms have emerged. In 5XFAD mice, intranasal (see FIG. 17A) but not subcutaneous (see FIG. 17B) dantrolene treatment significantly inhibited hippocampus-dependent memory impairment (see FIG. 17A, contextual) and trended to ameliorate the hippocampus-independent memory loss (see FIG. 17B, tone). In fact, intranasal dantrolene treatment restored hippocampus-dependent memory to the same level as in the WT controls.

Chronic Intranasal or Subcutaneous Dantrolene Treatment was Well Tolerated

Figure 17A:
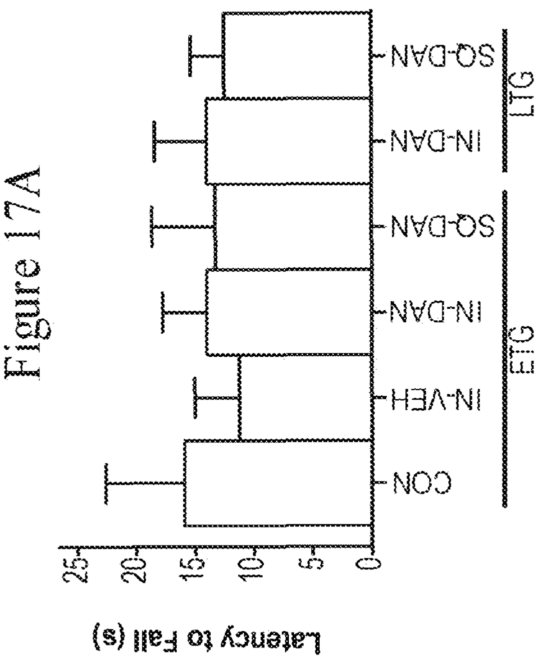
FIGS. 17A-17F show assessment of side effects of long-term dantrolene treatment. Intranasal administration of dantrolene (IN-DAN) or vehicle (IN-VEH) and subcutaneous administration of dantrolene (SQ-DAN) were administered 3×/week starting at 2 months of age for the early treatment group (ETG) and at 6 months of age for the late treatment group (LTG).
Figure 17B:
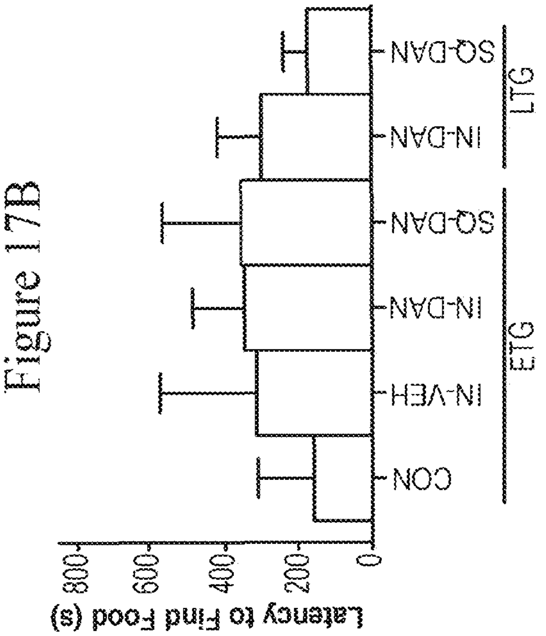
Figure 17C:
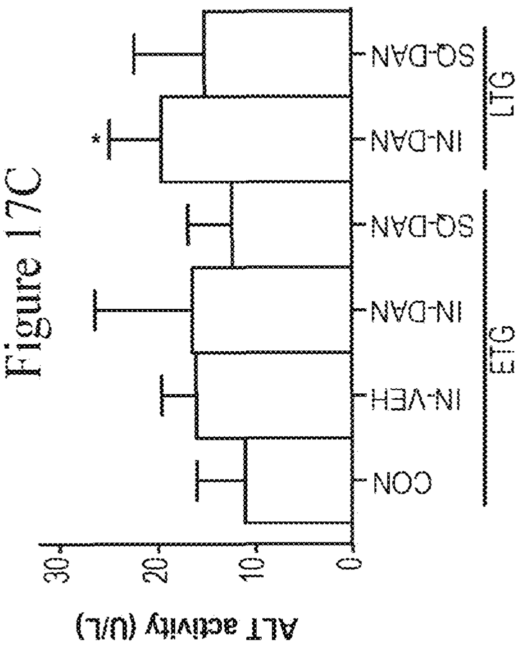
Figure 17D:
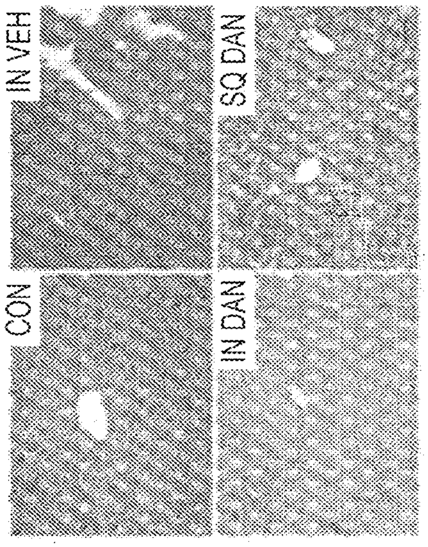
Figure 17E:
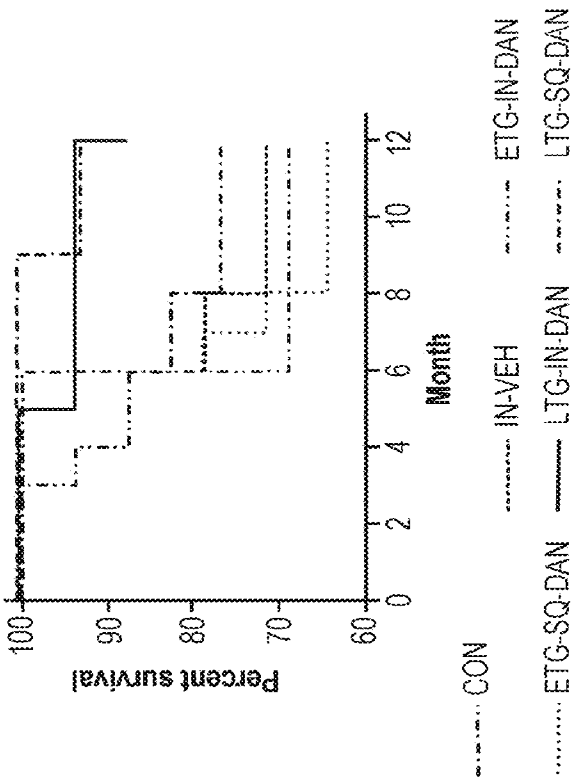
Figure 17F:
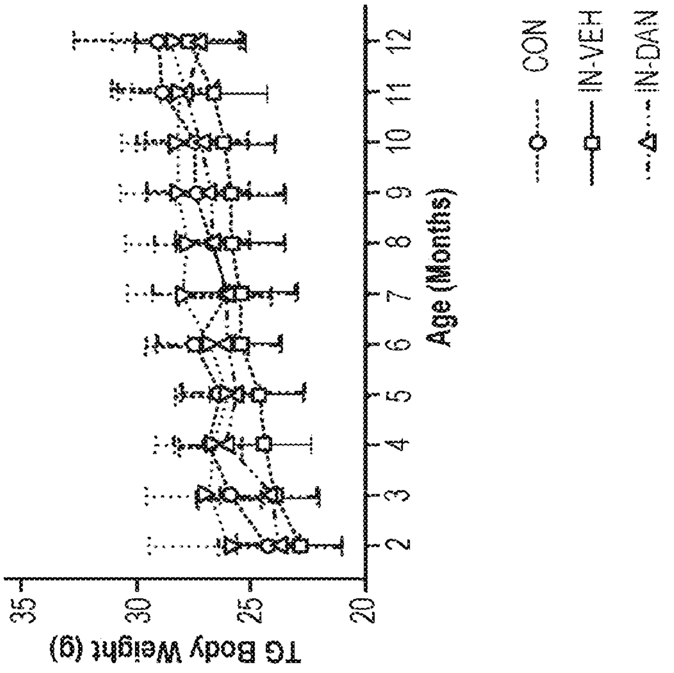
Figure 18A:
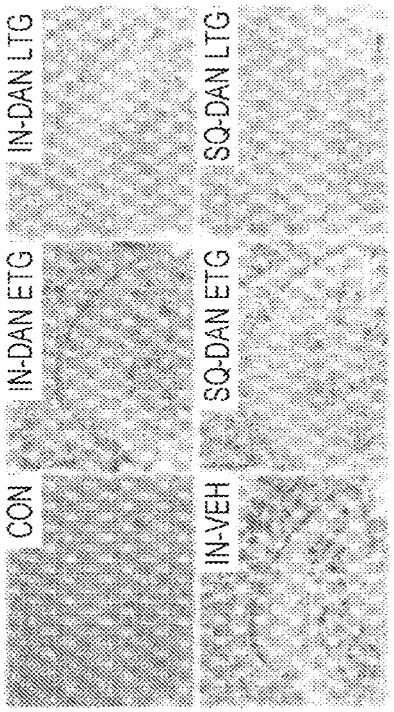
FIGS. 18A-18F show dantrolene had no significant effects on amyloid plaque levels in the dentate gyrus and hippocampus of 5XFAD mice.
Figure 18B:
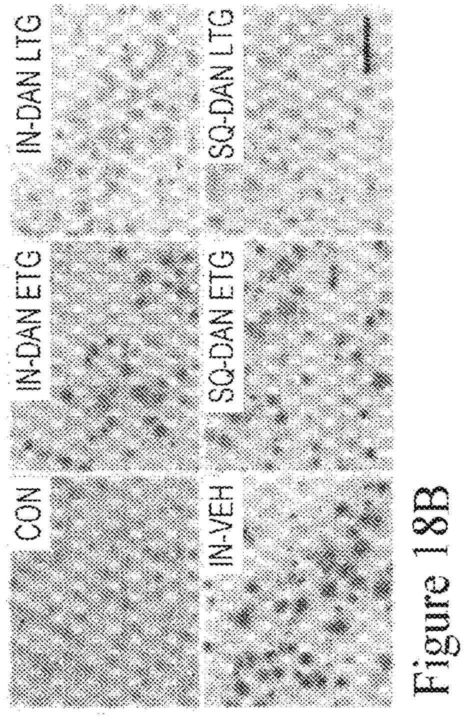
Figure 18C:
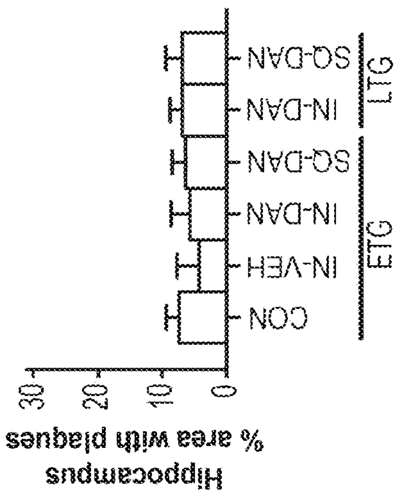
Figure 18D:
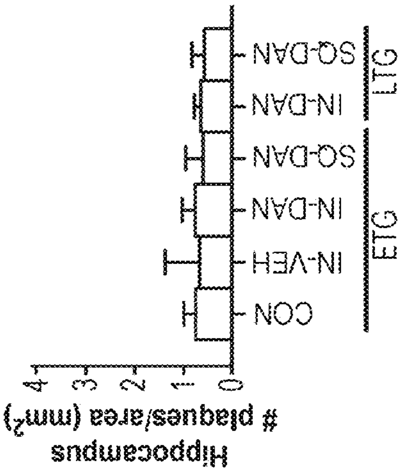
Figure 18E:
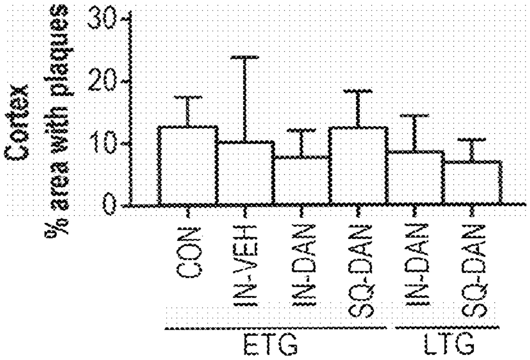
Figure 18F:
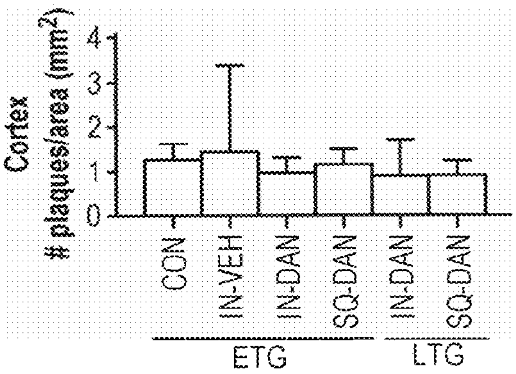
Figures 22A, 22B, 22C, 22D, 22E, 22F:
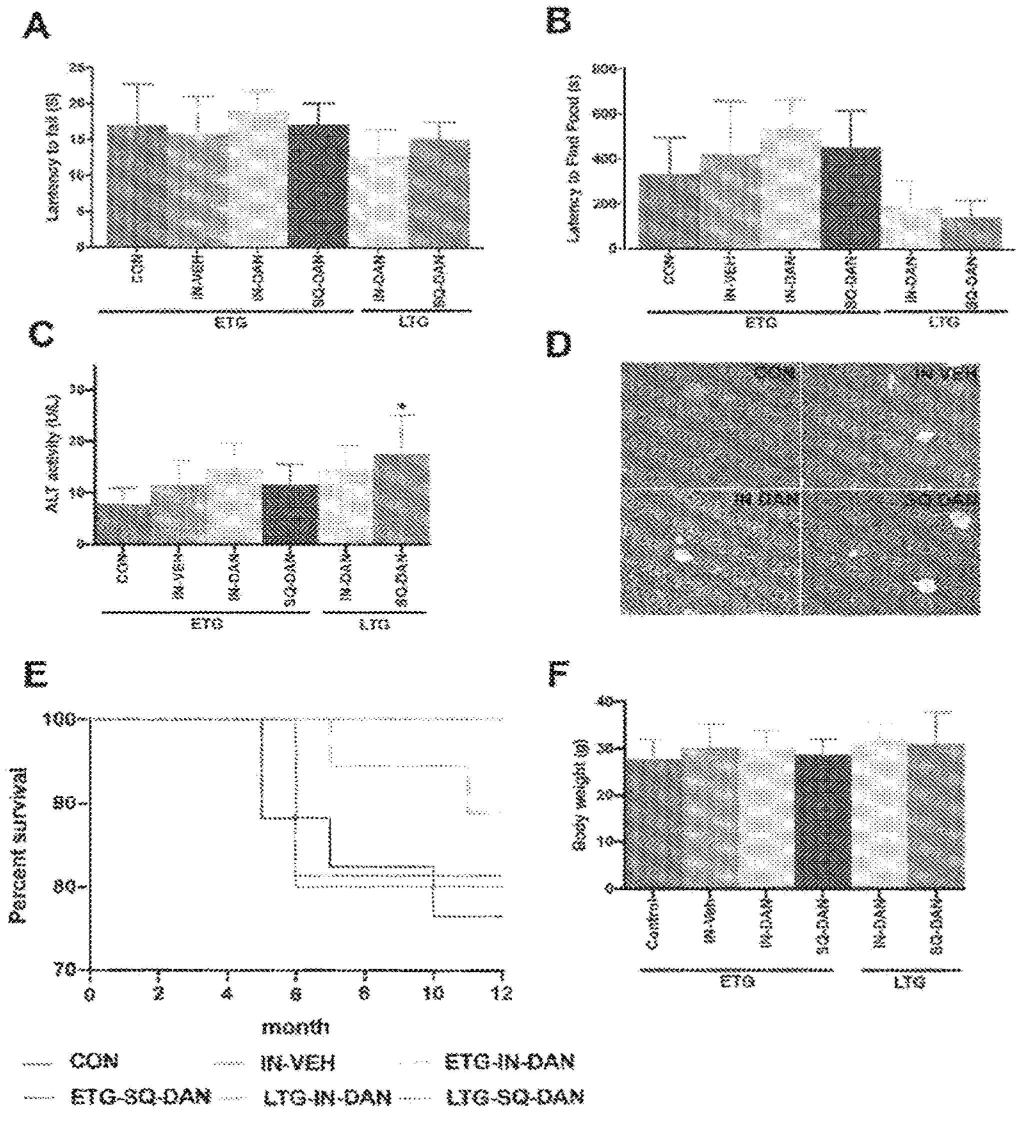
FIGS. 22A-22F show side effects after long-term dantrolene treatment in wild-type (WT) groups. Intranasal administration of dantrolene (IN-DAN) or vehicle (IN-VEH) and subcutaneous administration of dantrolene (SQ-DAN) were administered 3×/week starting at 2 months of age for the early treatment group (ETG) or at 6 months of age for the late treatment group (LTG).

In this study, there were no significant differences for the 5XFAD mice on motor function in rotarod performance after 7 months of treatment (ETG) and 3 months' treatment (LTG), compared with controls (FIG. 17A). Long-term intranasal dantrolene treatment may also damage nasal cells and impair olfaction. The present study found that the sense of smell was not significantly impaired after 6 months of intranasal treatment (ETG) or after 2 months of treatment (LTG) in the 5XFAD mice (FIG. 17B). (see also FIG. 16B, 6-7 months treatment for ETG and 2-3 months treatment for LTG, respectively.) Oral dantrolene, at a high dose for prolonged use, may impair liver function. In this study, dantrolene treatment, either intranasal or subcutaneous, for 10 months (ETG) had no significant effect on liver function or liver structure in the 5XFAD mice (FIG. 17C-17D). (see also FIG. 18C, 9-10-months treatment) and liver structure (see FIG. 18D, 9-10-months treatment). Furthermore, chronic intranasal or subcutaneous dantrolene treatment for up to 10 months did not affect mortality rates or body weight in either group of 5XFAD mice (FIG. 17E-17F). In wild type mice, there were no significant differences in olfaction, motor function, mortality, or body weight (FIGS. 22A-22C, 22E, 22F). While a significant increase in the liver enzyme, alanine aminotransferase, was detected in wild-type mice after 10 months of treatment (ETG), the values were still within the normal physiological range (FIG. 22D). Also, chronic intranasal or subcutaneous dantrolene treatments up to 10 months' duration did not affect mortality in either type of mice (Table 1).

TABLE 1

| Mortality of WT vs. 5XFAD mice | | |
|---|---|---|
| Groups | Number of WT Mice Died (Mortality %) | Number of mice 5XFAD Died (Mortality %) |
| Control | 16 (0%) | 17 (5.9%) |
| In Vec | 15 (0%) | 14 (7.1%) |
| In Dan E | 18 (11.1%) | 16 (12.5%) |
| Sub Dan E | 17 (23.5%) | 14 (14.3%) |
| In Dan L | 13 (0%) | 16 (6.3%) |
| Sub Dan L | 13 (0%) | 15 (6.7%) |

Figures 23A, 23B:
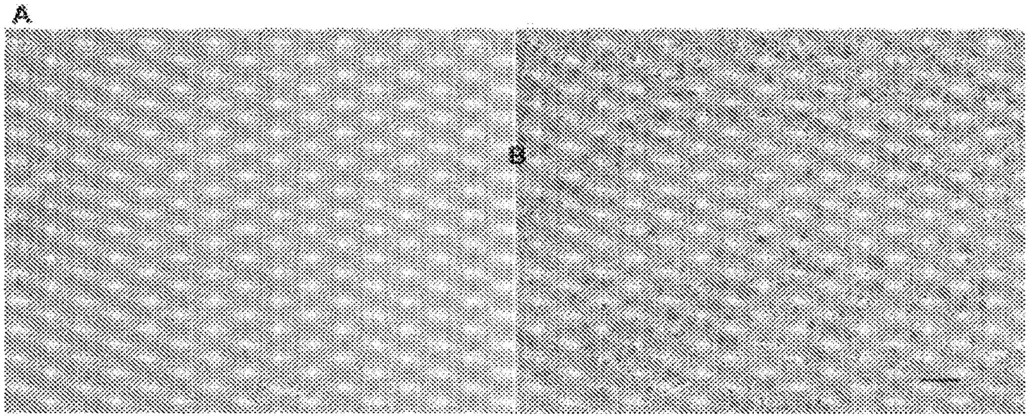
FIGS. 23A-23B show amyloid plaques levels in wild-type (WT-CON) and 5XFAD (TG-CON) mice. Representative micrographs of 6E10 immunoreactivity in hippocampus and cortex of wild type (WT) (FIG. 23A) and 5XFAD (TG) (FIG. 23B) control mice are presented (bar=100 μm).
Figures 24A, 24B, 24C, 24D:
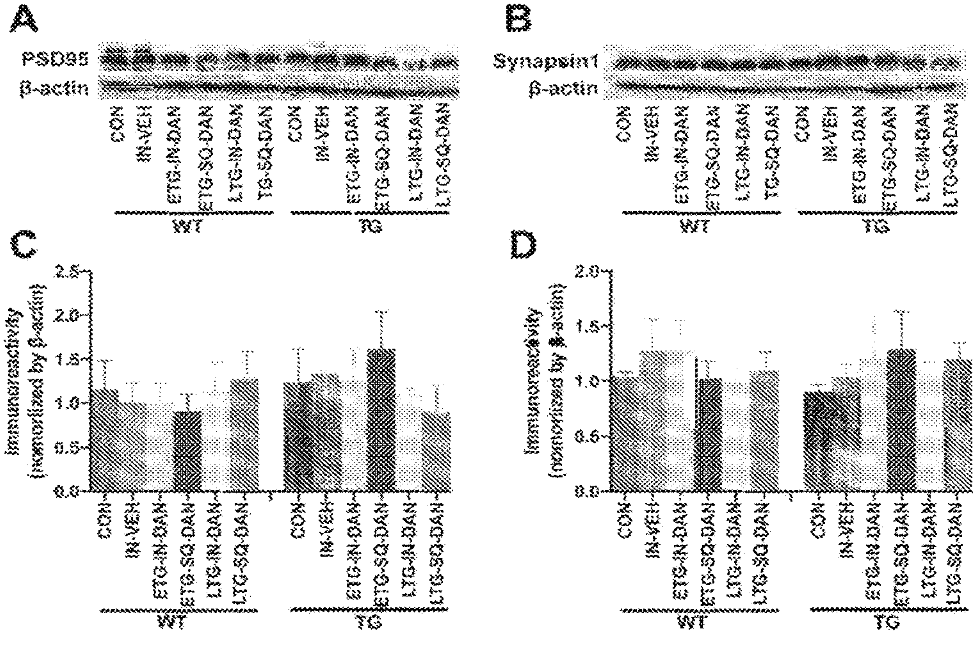
FIGS. 24A-24D show synaptic density in wild-type (WT) and 5XFAD (TG) mice.
Figure 25A:
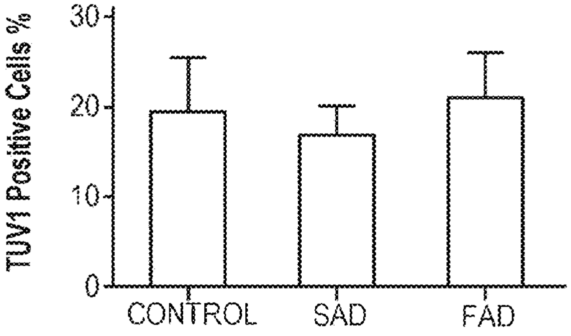
FIGS. 25A-25C show differentiation of induced pluripotent stem cells from Alzheimer's disease patients into immature neurons was significantly impaired. Induced pluripotent stem cells (iPSC) from healthy human subjects (CONTROL) or sporadic (SAD) or familial (FAD) Alzheimer's disease patients were differentiated into neurons (23 days). Immunocytochemistry was used for TUJ1 (FIG. 25A), DCX (FIG. 25B) and MAP2 (FIG. 25C) staining. All data are expressed as Mean±SD. N=3-10. *P<0.05.
Figure 25B:
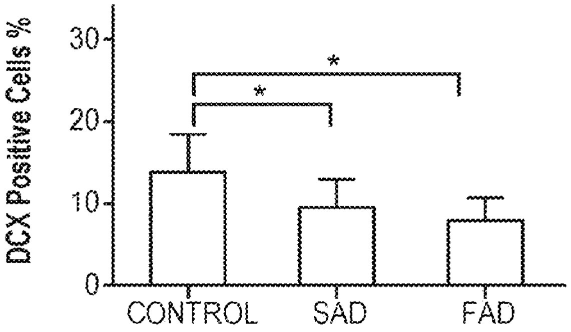
Figure 25C:
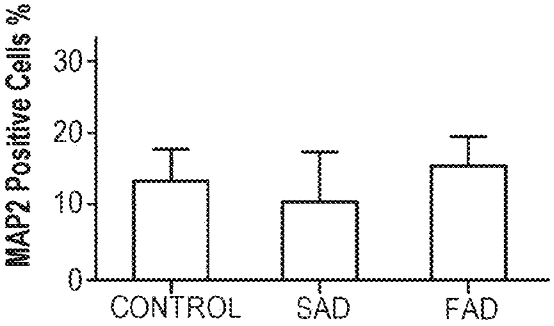
Figure 26:
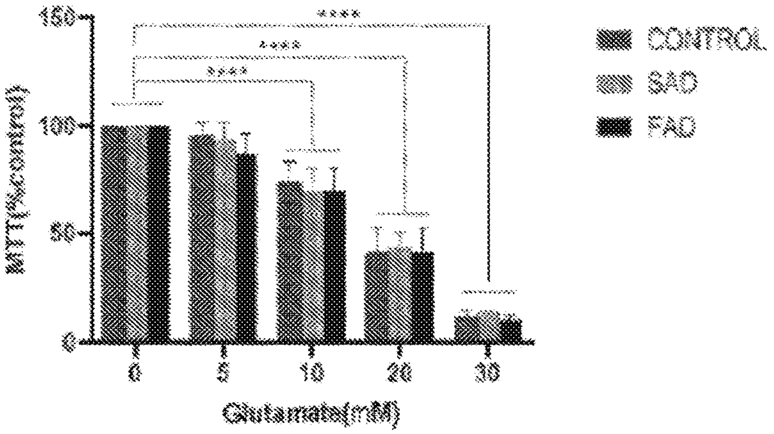
FIG. 26 shows glutamate dose-dependently decreased cell viability in iPSCs derived immature neurons from Alzheimer's disease (AD) patients. Neurons derived from induced pluripotent stem cells (iPSCs) from heathy human subjects (CONTROL), sporadic (SAD) or familial (FAD) Alzheimer's disease patients were exposed to different concentration of glutamate for 24 hours. Cell viability was measured by MTT reduction assay. Glutamate at 10 mM up to 30 mM induced significant cell damage in three types of cells dose-dependently. All data are expressed as Mean±SD. N=3-5, ****P<0.0001.
Figure 27:
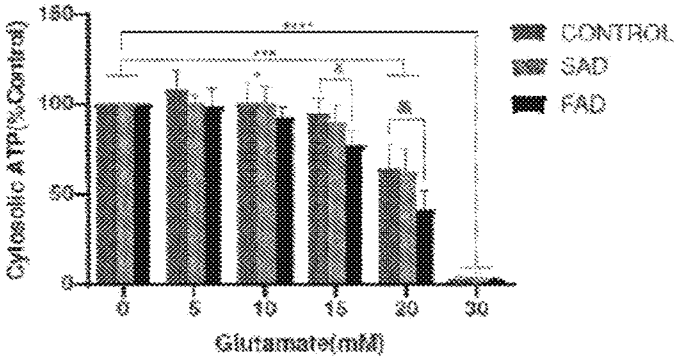
FIG. 27 shows glutamate dose-dependently decreased ATP amounts significantly more in familial Alzheimer's disease (FAD) cells. Neurons derived from induced pluripotent stem cells (iPSCs) from heathy human subjects (CONTROL), sporadic (SAD) or familial (FAD) Alzheimer's disease patients were exposed to different concentration of glutamate for 24 hours. ATP amount was evaluated using a commercially available luciferase-luciferin system. All data are expressed as Mean±SD. N=5-8, ****P<0.0001, &P<0.05, &&P<0.01.
Figure 28A:
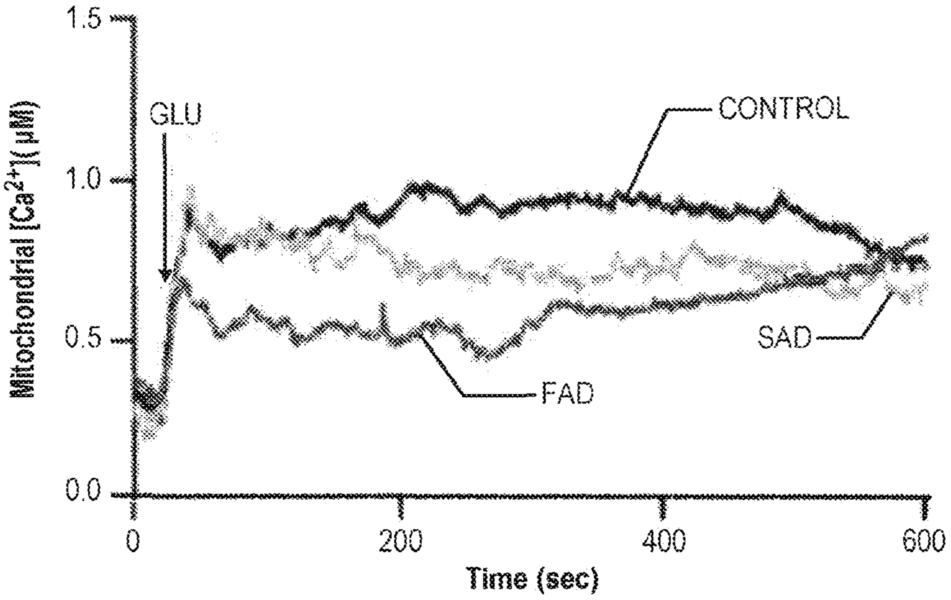
FIGS. 28A-28D show dantrolene significantly inhibited the glutamate mediated abnormal elevation of mitochondrial calcium concentration in neurons from familial Alzheimer's disease (FAD) patients. Neurons derived from induced pluripotent stem cells (iPSCs) from heathy human subjects (CONTROL), sporadic (SAD) or familial (FAD) Alzheimer's disease patients were exposed to 20 mM glutamate with or without dantrolene 20 μM pretreatment for 1 hour. Mitochondrial calcium concentration was measured using a jellyfish photoprotein aequorin-based probe. Typical curves of mitochondrial calcium concentration change exposed to glutamate without dantrolene pretreatment (FIG. 28A) or with dantrolene pretreatment (FIG. 28B) were demonstrated. Compared to CONTROL neurons, glutamate 20 mM increased peak elevation (FIG. 28C) and overall exposure (AUC (area under curve)) (FIG. 28D) of mitochondrial calcium concentrations significantly higher in FAD neurons, which was abolished by the pretreatment of dantrolene. All data are expressed as Mean±SD. N=3-9. *P<0.05, **P<0.01.
Figure 28B:
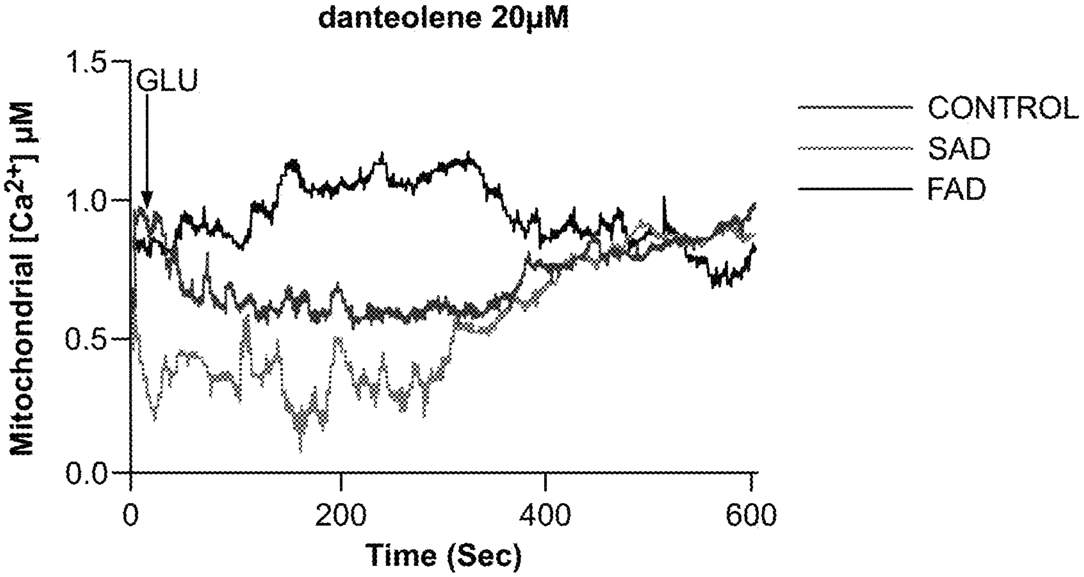
Figure 28C:
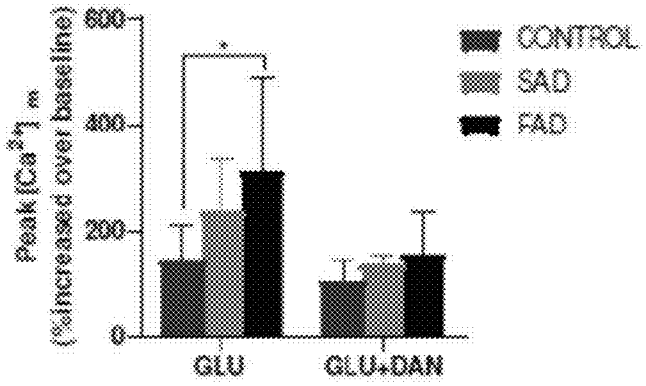
Figure 28D:
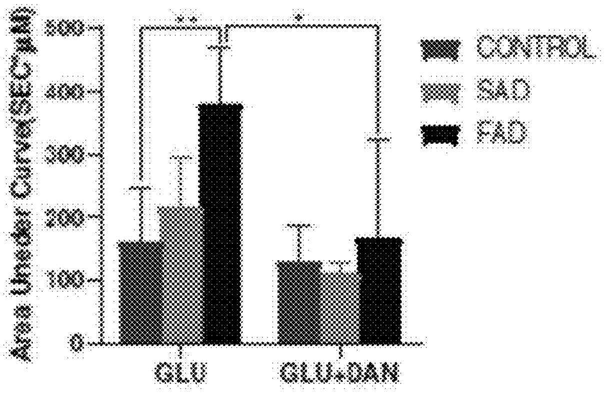

Significance among experimental groups.
In, Intranasal;
Sub, subcutaneous;
Dan, dantrolene Dantrolene Treatment Did not Reduce Amyloid Load in Hippocampus and Cortex of 5XFAD Mice The number and the area of the amyloid positive cells were determined and analyzed for both hippocampus and cortex (see FIGS. 18A-18F). Compared to WT control, there were significantly more amyloid plaques in both hippocampus (data not shown) and cortex (data not shown) of 5XFAD mice. Neither intranasal nor subcutaneous dantrolene treatment altered the amyloid load significantly in the hippocampus or cortex in 5XFAD mice (see FIGS. 18A-18F). No amyloid was detected in WT mice (FIG. 23A-23B).

No Significant Differences were Found in Synaptic Function-Related Proteins

The expression of PSD95 and synapsin1 from the whole brain were determined and analyzed for the ETG and LTG. There were no significant differences between the treatment groups and controls for either genotype (FIGS. 24A-24D).

In an aggressive animal model of AD using 5XFAD mice, the present study demonstrated that chronic intranasal dantrolene treatment, but not subcutaneous, nearly abolished memory loss, even when intranasal dantrolene treatment was started after the onset of apparent AD neuropathology and cognitive dysfunction. Intranasal dantrolene treatment showed disease-modifying properties, without obvious adverse effects on motor coordination, olfaction, liver function, and mortality in 5XFAD mice. The greater dantrolene penetration into the brain, as evidenced by the higher brain concentrations after intranasal administration, compared to the subcutaneous approach, is consistent to its better therapeutic effects on ameliorating memory impairment in 5XFAD mice. This is the first study showing improved CNS penetration and superior therapeutic effect of dantrolene on cognitive dysfunction after intranasal administration, compared to the subcutaneous approach, even as a disease modifying drug, rendering intranasal dantrolene treatment as a new drug treatment for AD.

This study elected to determine dantrolene plasma and brain concentrations at 20- and 60-minutes post-dose administration because these are the identified times to reach peak concentrations after intranasal or subcutaneous administration, respectively, in a pilot study.

This study found increased brain concentrations of dantrolene with the concomitant decrease in plasma concentrations at 20 and 60 min after intranasal administration compared to the subcutaneous approach. This suggests that intranasal delivery provides better penetration into the brain than the subcutaneous approach. The inventors have also found the intranasal dantrolene approach increased peak brain concentrations and prolonged the duration in the brain over the oral approach, but did not significantly increase its ability to pass the BBB. The benefit of the increased brain compared to plasma with the intranasal approach is the reduced therapeutic dose, thereby minimizing peripheral side effects.

In this study, MWM test also did not detect different cognitive function between WT and 5XFAD mice at 10 months old (FIGS. 21A-21F), further indicating the low sensitivity of MWM to determine learning and memory changes in aged mice (FIG. 22F). On the other hand, the fear conditioning tests demonstrated decreased hippocampus-dependent and -independent memory in 11-month old 5XFAD mice compared to WT control. Furthermore, the present study found that only intranasal administration of dantrolene but not subcutaneous administration of dantrolene at the same dose improved memory loss when the treatment was initiated after onset of AD pathology and cognitive dysfunction, as a disease-modifying drug, consistent with its relatively more efficient penetration into brain and higher brain dantrolene concentration. Dantrolene restores hippocampus-dependent memory more efficiently than hippocampus-independent memory, in 5XFAD mice. These results are clinically important because it is usually difficult and inconvenient to effectively diagnose AD before the onset of cognitive dysfunction. Thus, effective treatment even after onset of memory loss makes intranasal dantrolene treatment a promising therapeutic for AD patients. Another advantage of the intranasal administration of dantrolene in AD patients is its ease of use and convenience for patients, compared to other modes of administration.

Intranasal dantrolene treatment initiated either before or after onset of AD pathology and cognitive dysfunction did not affect extracellular plaque in 5XFAD mice, although it nearly abolished memory loss, acting as a disease-modifying drug.

This study indicated that intranasal or subcutaneous dantrolene at 5 mg/kg for up to 9-10 months did not affect mortality, liver structure and function or caused other severe side effects in 5XFAD mice, further strengthening the safety of dantrolene after chronic use. Furthermore, because the neuroprotective effect of dantrolene is clearly dose-dependent, the higher brain concentrations and lower plasma concentration after intranasal administration, relative to subcutaneous approach, make possible to further decrease intranasal dantrolene dose, while still maintaining effective therapy.

Intranasal dantrolene administration provides higher brain concentrations and better therapeutic effects to ameliorate memory loss compared to subcutaneous approach, as a disease-modifying drug, without affecting the extracellular amyloid plaques significantly or causing obvious side effects.

Example 4

Dantrolene Ameliorates Glutamate-Induced Mitochondrial Calcium Increase in Neurons from Alzheimer's Disease Patients Glutamate excitotoxicity and associated disruption of intracellular calcium homeostasis play important roles in pathology, synapse and cognitive dysfunction in Alzheimer's disease (AD). Excessive calcium release from the ER via over activation of ryanodine receptors (RyR) leads to mitochondria calcium overloading and dysfunction in AD, such as decreased oxygen consumption and ATP production. RyR calcium channels are necessary for the mitochondrial $Ca^{2+}$ increase caused by ER release, which is inhibited by dantrolene. This study investigated whether dantrolene ameliorates glutamate-induced mitochondrial calcium overloading in induced pluripotent stem cells (iPSCs) derived neurons from patients with AD, with its ability to inhibit RyR and N-methyl-D-aspartate (NMDA) receptors. This study demonstrates that dantrolene significantly inhibited glutamate-induced mitochondrial calcium increase and the associated reduction of cytosolic ATP concentration in neurons derived from AD patients.

Methods

Cell Cultures

Healthy control cells (AG02261) and iPSCs (AG11414) from sporadic Alzheimer's disease were obtained from John A. Kessler's lab. iPSCs (GM24675) from Familial Alzheimer's disease were purchased from Coriell Institute (Camden, New Jersey). Each type of iPSCs was generated from skin fibroblasts of one heathy human subject or one patient diagnosed of either sporadic Alzheimer's disease or familial Alzheimer's disease. The AG02261 cell line was derived from a 61-year-old male healthy patient. Another AG11414 cell line came from a 39-year-old male patient with early onset Alzheimer's disease who displayed an APOE3/E4 genotype. The GM24675 cell line was derived from a 60-year-old familial Alzheimer's disease patient with APOE genotype 3/3. The human induced pluripotent stem cells were maintained on Matrigel (BD Biosciences, USA)-coated plates in mTeSR™ plus medium (catalog No. 05825, Stem Cell Technologies, Canada) and were cultured in a 5% $CO_2$ humidified atmosphere at 37° C. The culture medium was changed every day.

The protocol for differentiation into immature cortical neurons from iPSCs was described previously by Shi, Y., et al., Nat Protoc, 2012; 7:1836, which is incorporated by reference in its entirety. Briefly, feeder-free culture was induced to neural progenitors via dual-SMAD inhibition. The cells were cultured in chemical defined condition with 2 μM SB431542 and 2 μM DMH1 (both from Tocris, USA) for 7 days. The medium was changed to neural maintenance medium (this is a 1:1 mixture of N-2 and B-27-containing media; N-2 medium consists of Dulbecco's modified Eagle's medium/F-12 GlutaMAX, 1×N-22, 5 μg/ml insulin, 1 mM 1-glutamine, 100 μM nonessential amino acids, 100 μM 2-mercaptoethanol, 50 units/ml penicillin, and 50 mg/ml streptomycin; B-27 medium consists of Neurobasal, 1×B-27, 200 mM 1-glutamine, 50 U/ml penicillins, and 50 mg/ml streptomycin) from day 12. Neural rosette structures should be obvious when cultures are viewed with an inverted microscope around days 12-17. From this point, medium was changed every other day.

Immunocytochemistry

The cells were plated and treated on 24 wells plate with glass coverslips. After treatment, cells were rinsed briefly in PBS and fixed in 4% paraformaldehyde for 15 min at room temperature followed by three times PBS washes for 5 minutes each. They were then blocked by 5% normal goat serum in PBS containing 0.1% Triton X-100 at room temperature for 1 h. The primary antibody was diluted in PBS containing 1% bovine serum albumin and 0.3% Triton X-100. After three times washes with PBS, cells were then incubated in secondary antibody (1:1000) diluted with PBS for 1 to 2 hours at room temperature in the dark. Lastly, the coverslips were rinsed with PBS once and stained with Hoechst 33342 (1:1000) in PBS for 2-5 minutes. After being washed with PBS three times for 5 minutes, the cells were mounted with Gold antifade reagent, cured on a flat surface in the dark overnight and sealed with nail polish and imaged. Primary antibodies concentrations were listed as following: TUJ1 (1:1000), DCX (1:500), MAP2 (1:500). Image acquisition and analysis are performed by people blinded to experiment treatment. Five sets of images were acquired at random locations on the cover glass and were subsequently merged using Image J 1.49v software (National Institutes of Health). The percentage of positive cells over the total number of cells was calculated and compared across different groups from at least three different cultures.

Cell Viability

The cell viability was determined using the 3-(4,5-dimethylthiazol-2yl)-2,5-diphenyltetrazolium bromide (MTT) reduction assay, as described previously. The day before treatment, 50,000 cells per well were seeded in a 96-well plate and incubated for 24 hours. Each treatment was repeated at least three times during each experiment. At the end of the treatments, 10 μl/well of 0.25% MTT solution was added to 96 well plates and incubated at 37° C. for 4 hours in dark until intracellular purple formazan crystals were visible under a microscope. The medium was then removed, and the formazan crystals were solubilized with 150 μl dimethyl sulfoxide (DMSO) per well, incubated at room temperature and covered with foil on a shaker for 30 minutes, until the purple crystals dissolved. The absorbance was measured at 540 nm on a plate reader (Synergy™ H1 microplate reader, BioTek, Winooski, VT, USA).

Cytosolic ATP Production

The cytosolic ATP production was evaluated by using a commercially available luciferase-luciferin system (ATPlite; PerkinElmer, Waltham, MA), as described previously. The day before treatment, 50,000 cells per well were seeded in a 96-well plate with 100 L medium and incubated for 24 hours. Each treatment was repeated at least three times during each experiment. 50 μL of mammalian cell lysis solution was added per well of a 96-well plate. The plate was shaken and then 50 μL substrate solution was added to the wells. The luminescence was measured with a BioTech Synergy H1 plate reader.

Cytosolic and Mitochondrial $Ca^{2+}$ Concentrations Measurements

The changes of cytosolic $Ca^{2+}$ concentration ($[Ca^{2+}]_c$) and mitochondrial $Ca^{2+}$ concentration ($[Ca^{2+}]_m$) of iPSCs derived neurons after glutamate exposure were measured using jellyfish photoprotein aequorin-based probe, as described by Bonora, M., et al., Nat Protoc 2013; 8:2105, which is incorporated by reference in its entirety. 12-15×$10^4$ cells were plated on 12-mm coverslips on a 24 wells plate, grown to 60-70% confluence, and then transfected with the cyt-Aeq or mit-Aeq plasmid using Lipofectamine 3000 transfection reagent (Thermo Fisher Scientific, USA) according to the manufacturer's instructions. The next day, the transfected cells were incubated with 5 μM coelenterazine for 1 hour with or without dantrolene 20 μM in modified Krebs-Ringer buffer (in mM: 135 NaCl, 5 KCl, 1 $MgCl_2$, 20 Hepes, 0.4 $KH_2PO_4$, pH 7.4) supplemented with 1 mM $CaCl_2$ and 5 mM glucose, and then were transferred to the perfusion chamber. All aequorin measurements were carried out in Krebs-Ringer buffer, and glutamate 20 mM with or without dantrolene 20 μM were added to the same medium. The experiments were performed in a custom-built aequorin recording system. The experiments were terminated by lysing the cells with 100 μM digitonin in a hypotonic $Ca^{2+}$-rich solution (10 mM $CaCl_2$ in $H_2O$), thus discharging the remaining aequorin pool. The light signal was collected and calibrated into $[Ca^{2+}]_c$ or $[Ca^{2+}]_m$ values by an algorithm based on the $Ca^{2+}$ response curve of aequorin at physiologic conditions of pH, [$Mg^{2+}$], and ionic strength, as previously described.

Data Analysis and Statistics

The statistical analyses were performed using GraphPad Prism 8 software (GraphPad Software, Inc., USA). All the values are expressed as means±SD. The data was analyzed with one-way ANOVA and two-way ANOVA using glutamate concentration and dantrolene as the between-group factors. $P<0.05$ was considered to indicate a statistically significant result. Each experiment was repeated at least three times. The experimental units (n) and statistical analyses used are indicated in the figures and legends.

Results

Differentiation from Induced Pluripotent Stem Cells (iPSCs) of Alzheimer Disease Patients into Immature Neurons was Significantly Impaired Induced pluripotent stem cells (iPSC) from healthy human subjects (Control) and sporadic (SAD) or familial (FAD) Alzheimer's disease patients were induced and differentiated into immature neurons (23 days) and characterized by specific antibodies targeting different types of cells. There was no significant difference among three types of cells in neuroprogenitors (TJU1 staining, FIG. 19A) and mature neurons (MAP2, FIG. 19C) positive cells. However, compared with CONTROL, immature neurons (DCX, FIG. 19B) positive cells derived from SAD and FAD patients were significantly decreased.

Glutamate Decreased iPSCs Derived Immature Neurons Cell Viability and ATP Production Dose Dependently A dose response study on the effects of glutamate on iPSCs derived immature neurons cell survival was performed using the MTT reduction assay. Glutamate from 10 to 30 mM dose dependently induced significant cell damage in three types of cells (FIG. 20). ATP production was evaluated by using a commercially available luciferase-luciferin system. Cytosolic ATP production was also dose dependently decreased when cells were exposed to glutamate (20-30 mM). Compared with healthy control, immature neurons from FAD patients iPSCs tended to have significant impaired ATP production when exposed to 15 mM and 20 mM glutamate (FIG. 21).

Dantrolene Ameliorated Glutamate Mediated Mitochondrial Calcium Increase in iPSCs Derived Immature Neurons.

The possible mechanisms by which ATP production were impaired in FAD patient iPSCs derived neurons was investigated further. Mitochondrial calcium concentration was measured using jellyfish photoprotein aequorin-based probe (FIGS. 22A, 22B). The glutamate-mediated peak elevation and overall exposure (AUC (Area Under Curve)) of mitochondrial calcium concentrations in FAD patient derived neurons were significantly higher than healthy control, which was ameliorated by the pretreatment of dantrolene (FIGS. 22C, 22D).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for improving and/or slowing the decline of cognitive function after onset of cognitive dysfunction, the method comprising intranasally administering to a subject suspected of having Alzheimer's Disease (AD) a pharmaceutical composition comprising dantrolene.

2. The method of claim 1, wherein the cognitive function is memory, learning, thinking, attention, perception, language use, reasoning, decision making, problem solving or a combination thereof.

3. The method of claim 1, wherein the AD is familial Alzheimer's disease (FAD).

4. The method of claim 1, wherein the pharmaceutical composition comprising dantrolene is administered three times per week.

5. The method of claim 1, wherein the pharmaceutical composition comprising dantrolene is administered for four months to one year.

6. The method of claim 1, wherein the pharmaceutical composition comprising dantrolene is administered for up to two years.

7. The method of claim 1, wherein the pharmaceutical composition comprising dantrolene is administered for more than two years.

8. The method of claim 1, wherein the cognitive dysfunction is short-term or long-term memory loss, learning difficulty, thinking difficulty, attention/concentration difficulty, perception difficulty, difficulty in language use, reasoning difficulty, difficulty in making decisions/impaired judgment, problem solving difficulty, confusion, or poor motor coordination, or a combination thereof.

9. The method of claim 8, wherein the short-term or long-term memory loss is hippocampal-dependent or hippocampal-independent memory loss.

10. The method of claim 1, further comprising administering a therapeutically effective amount of a glutamate receptor antagonist to the subject.

11. The method of claim 10, wherein the glutamate receptor antagonist is an agent that blocks the NMDA receptor by competitive antagonism at a glutamate-binding site or is an agent that blocks the NMDA receptor by noncompetitive antagonism at a glycine, phencyclidine, magnesium and/or MK-801 (dizocilpine) binding site.

12. The method of claim 11, wherein the agent that blocks the NMDA receptor by competitive antagonism at a glutamate-binding site is selected from selfotel (CGS 19755) aptiganel (CNS 1102), CGP 37849, APV or AP-5 (R-2-amino-5-phosphonopentanoate), 2-amino-7-phosphonoheptanoic acid (AP-7), 3-[(R)-2-carboxypiperazin-4-yl]-prop-2-enyl-1-phosphonic acid (CPPene) and/or aspartame.

13. The method of claim 11, wherein the agent that blocks the NMDA receptor by noncompetitive antagonism at a phencyclidine (PCP), magnesium, and/or MK-801 (dizocilpine) binding site is selected from memantine, ketamine, phencyclidine, 3-MEO-PCP, 8A-PDHQ, arnantadine, atomoxetine, AZD6765, agmatine, delucemine, dextrallorphan, dextromethorphan, dextrorphan, diphenidine, ethanol, eticylidine, gacyclidine, methoxetamine (MXE), minocycline, nitromemantine, nitrous oxide, PD-137889, rolicyclidine, tenocyclidine, methoxydine, tiletamine, neramexane, eliprodil, etoxadrol, dexoxadrol, WMS-2539, NEFA, remacemide, magnesium sulfate, aptiganel, HU-211, huperzine A, Dipeptide D-Phe-L-Tyr, Ibogaine, Apocynaceae, Rhynchophylline, gabapentin, or dizocilpine (MK-801).

14. The method of claim 11, wherein the agent that blocks the NMDA receptor by noncompetitive antagonism at a glycine binding site is selected from (GLYX-13), NRX-1074, 7-Chlorokynurenic acid, 4-Chlorokynurenine (AV-101), 5,7-Dichlorokynurenic acid, Kynurenic acid, TK-40

(competitive antagonist at the GluN1 glycine binding site), 1-aminocyclopropanecarboxylic acid (ACPC), L-Phenylalanine, or Xenon.

15. The method of claim 1, wherein the AD is sporadic Alzheimer's disease (SAD).

16. The method of claim 1, wherein the amount of the pharmaceutical composition comprising dantrolene administered to the subject is effective to inhibit over-activation of NMDA receptor and/or ryanodine receptor (RyR).

17. The method of claim 16, wherein the RyR is selected from the group consisting of Type 1 RyR (RyR-1), Type 2 RyR (RyR-2), Type 3 RyR (RyR-3) and combinations thereof.

* * * * *